(12) United States Patent
Hashash et al.

(10) Patent No.: US 8,324,389 B2
(45) Date of Patent: Dec. 4, 2012

(54) SOLID FORMS OF A RAF KINASE INHIBITOR

(75) Inventors: Ahmad Hashash, Pleasant Hill, CA (US); Kangwen L. Lin, Fremont, CA (US); Augustus O. Okhamafe, Concord, CA (US)

(73) Assignee: Novartis AG, Basel (CH)

( * ) Notice: Subject to any disclaimer, the term of this patent is extended or adjusted under 35 U.S.C. 154(b) by 476 days.

(21) Appl. No.: 12/529,258

(22) PCT Filed: Feb. 28, 2008

(86) PCT No.: PCT/US2008/055227
§ 371 (c)(1),
(2), (4) Date: Sep. 14, 2009

(87) PCT Pub. No.: WO2008/140850
PCT Pub. Date: Nov. 20, 2008

(65) Prior Publication Data
US 2010/0209418 A1    Aug. 19, 2010

Related U.S. Application Data

(60) Provisional application No. 60/904,455, filed on Mar. 2, 2007.

(51) Int. Cl.
*C07D 401/14* (2006.01)
(52) U.S. Cl. .................................................. 546/273.4
(58) Field of Classification Search ............... 546/273.4; 514/338
See application file for complete search history.

(56) References Cited

U.S. PATENT DOCUMENTS

| 6,627,646 B2 * | 9/2003 | Bakale et al. ................ 514/322 |
| 7,482,367 B2 * | 1/2009 | Aikawa et al. ................ 514/338 |
| 2007/0049622 A1 | 3/2007 | Dimitroff | |

FOREIGN PATENT DOCUMENTS

| WO | 2008/011154 A | 1/2008 |
| WO | 2008/027523 | 3/2008 |

OTHER PUBLICATIONS

Chemical & Engineering News, Feb. 2003, 32-35.*
Guillory (in Brittain ed.) "Polymorphism, etc.," NY: Marcel Dekker, Inc., 1999, 1-2, 125-181, 183-226, 235-239.*
US Pharmacopia #23, Nationa Formulary #18, 1995, 1843-1844.*
Jain et al., "Polymorphism in Pharmacy", Indian Drugs, 1986, 23(6) 315-329.*
Vippagunta et al., "Crystalline solids", Advanced Drug Delivery Reviews 48 (2001) 3-26.*
Rowland and Tozer. "Clinical Pharmacokinetics, etc.," 1995, p. 123.*
Silverman, The Organic Chemistry of Drug Design and Drug Action, NY: Academic Press, Inc. 1993, 72-76.*
Ulicky et al., Comprehensive Dictionary of Physical Chemistry, NY Ellis Horwood PTR Prentice Hall, 1992, p. 21.*
Doelker, english translation of S.T.P. Pharma Pratiques (1999), 9(5), 399-409, pp. 1-33.*
Muzaffar et al., "Polymorphism, etc.," Journal of Pharmacy (Lahore) 1979, 1(1), 59-66.*
Caira, "Crystalline Polymorphism, etc.," Topics in Current Chemistry, 198, Berline Heidelberg: Springer Vertag, 1998, pp. 164-208.*
Singhal et al., "Drug polymorphism, etc., "Advanced drug delivery reviews 56, 335-347 (2004).*
CMU Pharmaceutical polymorphism, intenet p. 1-3 (2002) (printout Apr. 3, 2008).*
Dean "Analytical Chemistry Handbook" p. 10.24-10.26 (1995).*

* cited by examiner

*Primary Examiner* — Patricia Morris
(74) *Attorney, Agent, or Firm* — Foley & Lardner LLP

(57) ABSTRACT

The present invention is directed to solid forms of the Raf kinase inhibitor 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine, as well as compositions thereof and uses of the same.

9 Claims, 48 Drawing Sheets

Form A

Form B

Form C

Form D

Form E

Form F

Form G

Form H

Form I

Form J

Form K

Form L

Form M

Form N

Form O

Form P

Form A

Form B

Form C

Form D

Form E

Form F

Form G

Form H

Form I

Form J

Form K

Form L

Form M

Form N

Form O

Form P

From A

Form B

Form C

Form D

Form E

Form F

Form G

Form H

Form I

Form J

Form K

Form L

Form M

Form N

Form O

Form P

SOLID FORMS OF A RAF KINASE INHIBITOR

This is a National Stage of International Application No. PCT/US/2008/055227 filed on Feb. 28, 2008, which claims the benefit of U.S. Provisional Application No.: 60/904,455 filed Mar. 2, 2007 which in its entirety are herein incorporated by reference.

FIELD OF THE INVENTION

The present invention is directed to solid forms of the Raf kinase inhibitor 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine, as well as compositions thereof and uses of the same.

BACKGROUND OF THE INVENTION

Kinases known to be associated with tumorigenesis include the Raf serine/threonine kinases and the receptor tyrosine kinases (RTKs).

The Raf serine/threonine kinases are essential components of the Ras/Mitogen-Activated Protein Kinase (MAPK) signaling module that controls a complex transcriptional program in response to external cellular stimuli. Raf genes code for highly conserved serine-threonine-specific protein kinases which are known to bind to the ras oncogene. They are part of a signal transduction pathway believed to consist of receptor tyrosine kinases, p21 ras, Raf protein kinases, Mek1 (ERK activator or MAPKK) kinases and ERK (MAPK) kinases, which ultimately phosphorylate transcription factors. In this pathway Raf kinases are activated by Ras and phosphorylate and activate two isoforms of Mitogen-Activated Protein Kinase Kinase (called Mek1 and Mek2), that are dual specificity threonine/tyrosine kinases. Both Mek isoforms activate Mitogen Activated Kinases 1 and 2 (MAPK, also called Extracellular Ligand Regulated Kinase 1 and 2 or Erk1 and Erk2). The MAPKs phosphorylate many substrates including transcription factors and in so doing set up their transcriptional program. Raf kinase participation in the Ras/MAPK pathway influences and regulates many cellular functions such as proliferation, differentiation, survival, oncogenic transformation and apoptosis.

Both the essential role and the position of Raf in many signaling pathways have been demonstrated from studies using deregulated and dominant inhibitory Raf mutants in mammalian cells as well as from studies employing biochemical and genetic techniques of model organisms. In many cases, the activation of Raf by receptors that stimulate cellular tyrosine phosphorylation is dependent on the activity of Ras, indicating that Ras functions upstream of Raf. Upon activation, Raf-1 then phosphorylates and activates Mek1, resulting in the propagation of the signal to downstream effectors, such as MAPK (mitogen-activated protein kinase; Crews et al., 1993, *Cell* 74:215). The Raf serine/threonine kinases are considered to be the primary Ras effectors involved in the proliferation of animal cells (Avruch et al., 1994, *Trends Biochem. Sci.* 19:279).

Raf kinase has three distinct isoforms, Raf-1 (c-Raf), A-Raf, and B-Raf, distinguished by their ability to interact with Ras, to activate MAPK kinase pathway, tissue distribution and sub-cellular localization (Marias et al., *Biochem. J.* 351:289-305, 2000; Weber et al., *Oncogene* 19:169-176, 2000; Pritchard et al., *Mol. Cell. Biol.* 15:6430-6442, 1995). Activating mutation of one of the Ras genes can be seen in about 20% of all tumors and the Ras/Raf/MEK/ERK pathway is activated in about 30% of all tumors (Bos et al., *Cancer Res.* 49:4682-4689, 1989; Hoshino et al., *Oncogene* 18:813-822, 1999). Recent studies have shown that B-Raf mutation in the skin nevi is a critical step in the initiation of melanocytic neoplasia (Pollock et al., *Nature Genetics* 25: 1-2, 2002). Furthermore, most recent studies have disclosed that activating mutation in the kinase domain of B-Raf occurs in about 66% of melanomas, 12% of colon carcinoma and 14% of liver cancer (Davies et al., *Nature* 417:949-954, 2002; Yuen et al., *Cancer Research* 62:6451-6455, 2002; Brose et al., *Cancer Research* 62:6997-7000, 2002).

Melanoma, which continues to represent a significant unmet medical need, is a complex multigenic disease with a poor prognosis, especially in the advanced metastatic state. Activating somatic mutations in the B-Raf proto-oncogene have recently been discovered in a variety of malignancies, and most frequently in melanoma. Approximately 70% of melanoma express a mutated and activated form of B-Raf (V600E), making it an excellent target for drug development. Furthermore, another 10-15% of melanomas express mutant N-Ras, further demonstrating the importance of the MAPK pathway in the growth and survival of melanoma cells.

Inhibitors of the Ras/Raf/MEK/ERK pathway at the level of Raf kinases can potentially be effective as therapeutic agents against tumors with over-expressed or mutated receptor tyrosine kinases, activated intracellular tyrosine kinases, tumors with aberrantly expressed Grb2 (an adapter protein that allows stimulation of Ras by the Sos exchange factor) as well as tumors harboring activating mutations of Raf itself. In the early clinical trials inhibitors of Raf-1 kinase that also inhibit B-Raf have shown promise as therapeutic agents in cancer therapy (Crump, *Current Pharmaceutical Design* 8:2243-2248, 2002; Sebastien et al., *Current Pharmaceutical Design* 8: 2249-2253, 2002).

Disruption of Raf expression in cell lines through the application of RNA antisense technology has been shown to suppress both Ras and Raf-mediated tumorigenicity (Kolch et al., *Nature* 349:416-428, 1991; Monia et al., *Nature Medicine* 2(6):668-675, 1996). It has also been shown that the administration of deactivating antibodies against Raf kinase or the co-expression of dominant negative Raf kinase or dominant negative MEK, the substrate of Raf kinase, leads to the reversion of transformed cells to the normal growth phenotype (see Daum et al., *Trends Biochem. Sci* 1994, 19:474-80; Fridman et al. *J. Biol. Chem.* 1994, 269:30105-8).

Several Raf kinase inhibitors have been described as exhibiting efficacy in inhibiting tumor cell proliferation in vitro and/or in vivo assays (see, e.g., U.S. Pat. Nos. 6,391,636, 6,358,932, 6,037,136, 5,717,100, 6,458,813, 6,204,467, and 6,268,391). Other patents and patent applications suggest the use of Raf kinase inhibitors for treating leukemia (see, e.g., U.S. Pat. Nos. 6,268,391, and 6,204,467, and published U.S. Patent Application Nos. 20020137774; 20020082192; 20010016194; and 20010006975), or for treating breast cancer (see, e.g., U.S. Pat. Nos. 6,358,932, 5,717,100, 6,458,813, 6,268,391, and 6,204,467, and published U.S. Patent Application No. 20010014679).

Angiogenesis also plays an important role in the growth of cancer cells. It is known that once a nest of cancer cells reaches a certain size, roughly 1 to 2 mm in diameter, the cancer cells must develop a blood supply in order for the tumor to grow larger as diffusion will not be sufficient to supply the cancer cells with enough oxygen and nutrients. Thus, inhibition of angiogenesis is expected to inhibit the growth of cancer cells.

Receptor tyrosine kinases (RTKs) are transmembrane polypeptides that regulate developmental cell growth and differentiation, remodeling and regeneration of adult tissues (Mustonen, T. et al., *J. Cell Biology* 129:895-898, 1995; van der Geer, P. et al., *Ann Rev. Cell Biol.* 10:251-337, 1994). Polypeptide ligands, known as growth factors or cytokines, are known to activate RTKs. Signaling RTKs involves ligand binding and a shift in conformation in the external domain of the receptor resulting in its dimerization (Lymboussaki, A. "Vascular Endothelial Growth Factors and their Receptors in Embryos, Adults, and in Tumors" Academic Dissertation, University of Helsinki, Molecular/Cancer Biology Laboratory and Department of Pathology, Haartman Institute, 1999; Ullrich, A. et al., *Cell* 61:203-212, 1990). Binding of the ligand to the RTK results in receptor trans-phosphorylation at specific tyrosine residues and subsequent activation of the catalytic domains for the phosphorylation of cytoplasmic substrates (Id).

Two subfamilies of RTKs are specific to the vascular endothelium. These include the vascular endothelial growth factor (VEGF) subfamily and the Tie receptor subfamily. Class V RTKs include VEGFR1 (FLT-1), VEGFR2 (KDR (human), Flk-1 (mouse)), and VEGFR3 (FLT-4) (Shibuya, M. et al., *Oncogene* 5:519-525, 1990; Terman, B. et al., *Oncogene* 6:1677-1683, 1991; Aprelikova, O. et al., *Cancer Res.* 52:746-748, 1992). Members of the VEGF subfamily have been described as being able to induce vascular permeability and endothelial cell proliferation and further identified as a major inducer of angiogenesis and vasculogenesis (Ferrara, N. et al., *Endocrinol. Rev.* 18:4-25, 1997).

VEGF is known to specifically bind to RTKs including FLT-1 and Flk-1 (DeVries, C. et al., *Science* 255:989-991, 1992; Quinn, T. et al., *Proc. Natl. Acad. Sci.* 90:7533-7537, 1993). VEGF stimulates the migration and proliferation of endothelial cells and induces angiogenesis both in vitro and in vivo (Connolly, D. et al., *J. Biol. Chem.* 264:20017-20024, 1989; Connolly, D. et al., *J. Clin. Invest.* 84:1470-1478, 1989; Ferrara, N. et al., *Endocrinol. Rev.* 18:4-25, 1997; Leung, D. et al., *Science* 246:1306-1309, 1989; Plouet, J. et al., *EMBO J.* 8:3801-3806, 1989).

Studies in various cultured endothelial cell systems have established that VEGFR2 mediates the majority of downstream effects of VEGF in angiogenesis (Wey S. et al., *Clinical Advances in Hematology and Oncology*, 2:37-45, 2004). VEGFR2 mediated proliferation of endothelial cells is believed to involve activation of the Ras/Raf/Mek/Erk pathway (Veikkola T. et al., *Cancer Res* 60:203-212, 2000). VEGFR2 expression has been observed in melanoma, breast cancer, bladder cancer, lung cancer, thyroid cancer, prostate cancer, and ovarian cancer (see Wey et al., supra). Neutralizing monoclonal antibodies to VEGFR2 (KDR) have been shown to be efficacious in blocking tumor angiogenesis (see Kim et al., *Nature* 362:841, 1993; Rockwell et al., *Mol. Cell. Differ.* 3:315, 1995). Because angiogenesis is known to be critical to the growth of cancer and to be controlled by VEGF and VEGF-RTK, substantial efforts have been undertaken to develop compounds which inhibit or retard angiogenesis and inhibit VEGF-RTK.

Platelet derived growth factor receptor kinase (PDGFR) is another type of RTK. PDGF expression has been shown in a number of different solid tumors, from glioblastomas and osteosarcoma to prostate carcinomas. In these various tumor types, the biological role of PDGF signaling can vary from autocrine stimulation of cancer cell growth to more subtle paracrine interactions involving adjacent stroma and angiogenesis. PDGF interacts with tyrosine kinases receptors PDGFRα and PDGFRβ. Therefore, inhibiting the PDGFR kinase activity with small molecules is expected to interfere with tumor growth and angiogenesis.

The fibroblast growth factor receptor kinases (FGFRs) represent another type of RTKs. The fibroblast growth factors are a family of polypeptide growth factors involved in a variety of activities, including mitogenesis, angiogenesis, and wound healing. They comprise a family of related but individually distinct tyrosine kinase receptors containing an extracellular domain with either 2 or 3 immunoglobulin (Ig)-like domains, a transmembrane domain, and a cytoplasmic tyrosine kinase domain. The fibroblast growth factor receptors that have been identified include FGFR1 (Ruta, M et al, *Oncogene* 3:9-15, 1988); FGFR2 (Dionne, C et al., *Cytogenet. Cell Genet.* 60:34-36, 1992); FGFR3 (Keegan, K et al., *Proc. Nat. Acad. Sci.* 88:1095-1099, 1991); and FGFR4 (Partanen, J et al., *EMBO J.* 10:1347-1354, 1991).

The role of the fibroblast growth factor receptors, particularly FGFR3, in cancer has been illuminated. Dysregulation of oncogenes by translocation to the immunoglobulin heavy chain (IgH) locus on 14q32 is a seminal event in the pathogenesis of B-cell tumors. In multiple myeloma, translocations to the IgH locus occur in 20 to 60% of cases. For most translocations, the partner chromosome is unknown; for the others, a diverse array of chromosomal partners have been identified, with 11q13, the only chromosome that is frequently involved. Bergsagel et al. identified illegitimate switch recombination fragments (defined as containing sequences from only 1 switch region) as potential markers of translocation events into IgH switch regions in 15 of 21 myeloma cell lines, including 7 of 8 karyotyped lines that had no detectable 14q32 translocation. These translocation breakpoints involved 6 chromosomal loci: 4p16.3; 6; 8q24.13; 11q13.3; 16q23.1; and 21q22.1 (Bergsagel et al., *Proc. Nat. Acad. Sci.* 93:13931-13936, 1996). Chesi et al. (*Nature Genet.* 16:260-264 1997) found the karyotypically silent translocation t(4;14) (p16.3;q32.3) in 5 myeloma cells lines and in at least 3 of 10 primary tumors associated with multiple myeloma to exhibit increased expression and activation of mutations of FGFR3. The chromosome-4 breakpoints were clustered in a 70-kb region centromeric to FGFR3, which was thought to be the dysregulated oncogene. Two lines and 1 primary tumor with this translocation selectively expressed an FGFR3 allele containing activating mutations identified previously in thanatophoric dwarfism: tyr373 to cys, lys650 to glu, and lys650 to met. For K650E, the constitutive activation of FGFR3 in the absence of ligand had been proved by transfection experiments. Chesi et al. (1997) proposed that after the t(4;14) translocation, somatic mutation during tumor progression frequently generates an FGFR3 protein that is active in the absence of ligand.

Rasmussen, T et al. cited a frequency of 3 to 24% for the t(4;14) translocation in multiple myeloma (Rasmussen, T et al., *Br. J. Haematol.* 117:626-628, 2002). The translocation was observed at a significantly lower frequency in patients with monoclonal gammopathy of undetermined significance (MGUS), suggesting a role in the transition from MGUS to multiple myeloma. The t(4;14) translocation affects 2 potential oncogenes: FGFR3 and multiple myeloma set domain (MMSET). Rasmussen et al. (2002) investigated the frequency of FGFR3 dysregulation and its prognostic value in multiple myeloma. In 16 of 110 (14.5%) multiple myeloma bone marrow samples, they found dysregulated FGFR3 expression.

In addition, further evidence has been presented indicating an oncogenic role for FGFR3 in carcinomas (Cappellen, D. et al., (Letter) *Nature Genet.* 23:18-20, 1999). Cappellen et al. found expression of a constitutively activated FGFR3 in a large proportion of 2 common epithelial cancers, bladder and cervix. FGFR3 appeared to be the most frequently mutated oncogene in bladder cancer, being mutated in more than 30% of cases. FGFR3 seems to mediate opposite signals, acting as a negative regulator of growth in bone and as an oncogene in several tumor types. All FGFR3 missense somatic mutations identified in these cancers were identical to the germinal activating mutations that cause thanatophoric dysplasia (the authors noted that in 2 mutations, this equivalency occurred because the FGFR3b isoform expressed in epithelial cells contains 2 more amino acids than the FGFR3c isoform expressed in bone). Of the FGFR3 alterations in epithelial tumors, the S249C mutation was the most common, affecting 5 of 9 bladder cancers and 3 of 3 cervical cancers.

Evidence has also been presented indicating that activated FGFR3 is targeted for lysosomal degradation by c-Cbl-mediated ubiquitination, and that activating mutations found in patients with achondroplasia and related chondrodysplasias disturb this process, leading to recycling of activated receptors and amplification of FGFR3 signals (Cho et al., *Proc. Nat. Acad. Sci.* 101:609-614, 2004). Cho et al. suggested that this mechanism contributes to the molecular pathogenesis of achondroplasia and represents a potential target for therapeutic intervention. The lysosomal targeting defect is additive to other mechanisms proposed to explain the pathogenesis of achondroplasia.

Other results indicate that FGFR2 and FGFR3 are significant factors in tumorigenesis (Jang J H et al., "Mutations in fibroblast growth factor receptor 2 and fibroblast growth factor receptor 3 genes associated with human gastric and colorectal cancers" *Cancer Res.* 61(9):354 1-3, 2001). Due to their role in multiple myeloma, bladder cancer, and tumorigenesis, development of inhibitors of fibroblast growth factor receptor kinases, particularly inhibitors of FGFR2 and FGFR3, will play an import role in the treatment of cancers.

c-Kit is another receptor tyrosine kinase belonging to PDGF Receptor family and is normally expressed in hematopoietic progenitor, mast and germ cells. C-kit expression has been implicated in a number of cancers including mast cell leukemia, germ cell tumors, small-cell lung carcinoma, gastrointestinal stromal tumors, acute myelogenous leukemia (AML), erythroleukemia, neuroblastoma, melanoma, ovarian carcinoma, breast carcinoma (Heinrich, M. C. et al; *J. Clin. Onc.* 20, 6 1692-1703, 2002 (review article); Smolich, B. D. et al., *Blood,* 97, 5; 1413-1421).

Overexpression of CSF-1R, the receptor for colony stimulating factor-1 (CSF-1) has been implicated in a number of human carcinomas, including carcinomas of the breast, ovary, endometrium, lung, kidney, pancreas and prostate (Sapi, E., *Exp. Biol. Med.* 229:1-11, 2004). CSF-1R is tyrosine kinase receptor which, when activated by its ligand CSF-1, triggers signal transduction pathways controlling cell proliferation and differentiation. CSF-1R is expressed in the mammary gland during pregnancy and lactation. Abnormal CSF-1R expression has been correlated with 58% of all breast cancers, and with 85% of invasive breast carcinoma (see Sapi, supra).

Because improved drug formulations showing, for example, better bioavailability and/or better stability are consistently sought, there is an ongoing need for new or purer solid forms of existing drug molecules that inhibit the proliferation of capillaries, inhibit the growth of tumors, treat cancer, modulate cell cycle arrest, and the like. The solid forms of 1-methyl-5-(2-(5-(trifluoromethyl)-1H-imidazol-2-yl)pyridin-4-yloxy)-N-(4-(trifluoromethyl)phenyl)-1H-benzo[d] imidazol-2-amine, described herein, are directed toward this end.

SUMMARY OF THE INVENTION

The present invention provides solid forms A-P of 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine as characterized by, for example, the XRPD, DSC, and TGA data provided herein.

The present invention further provides processes of preparing the solid forms described herein, and products resulting from the processes.

The present invention further provides compositions, such as pharmaceutical compositions, that comprise a solid form described herein and at least one pharmaceutically acceptable carrier.

The present invention further provides methods for treating cancer in a human or animal subject, comprising administering to the human or animal subject a solid form of the invention, or pharmaceutical composition comprising the same.

The present invention further provides methods of inhibiting at least one serine/threonine kinase in the MAPK signaling pathway in a subject, or treating a biological condition mediated by a serine/threonine kinase in the MAPK signaling pathway in a subject, comprising: administering to the subject a solid form of the invention or a pharmaceutical composition thereof.

The present invention further provides method of inhibiting a receptor tyrosine kinase in a subject or treating a biological condition mediated by the receptor tyrosine kinase in a subject, comprising administering to the subject a solid form of the invention, or a pharmaceutical composition thereof.

The present invention further provides a solid form herein for use in therapy, such as according to any one or more of the therapeutic methods described herein.

The present invention further provides a solid form here for use in the preparation of a medicament for use in therapy, such as according to any one or more of the therapeutic methods described herein.

DETAILED DESCRIPTION

Figure 1:
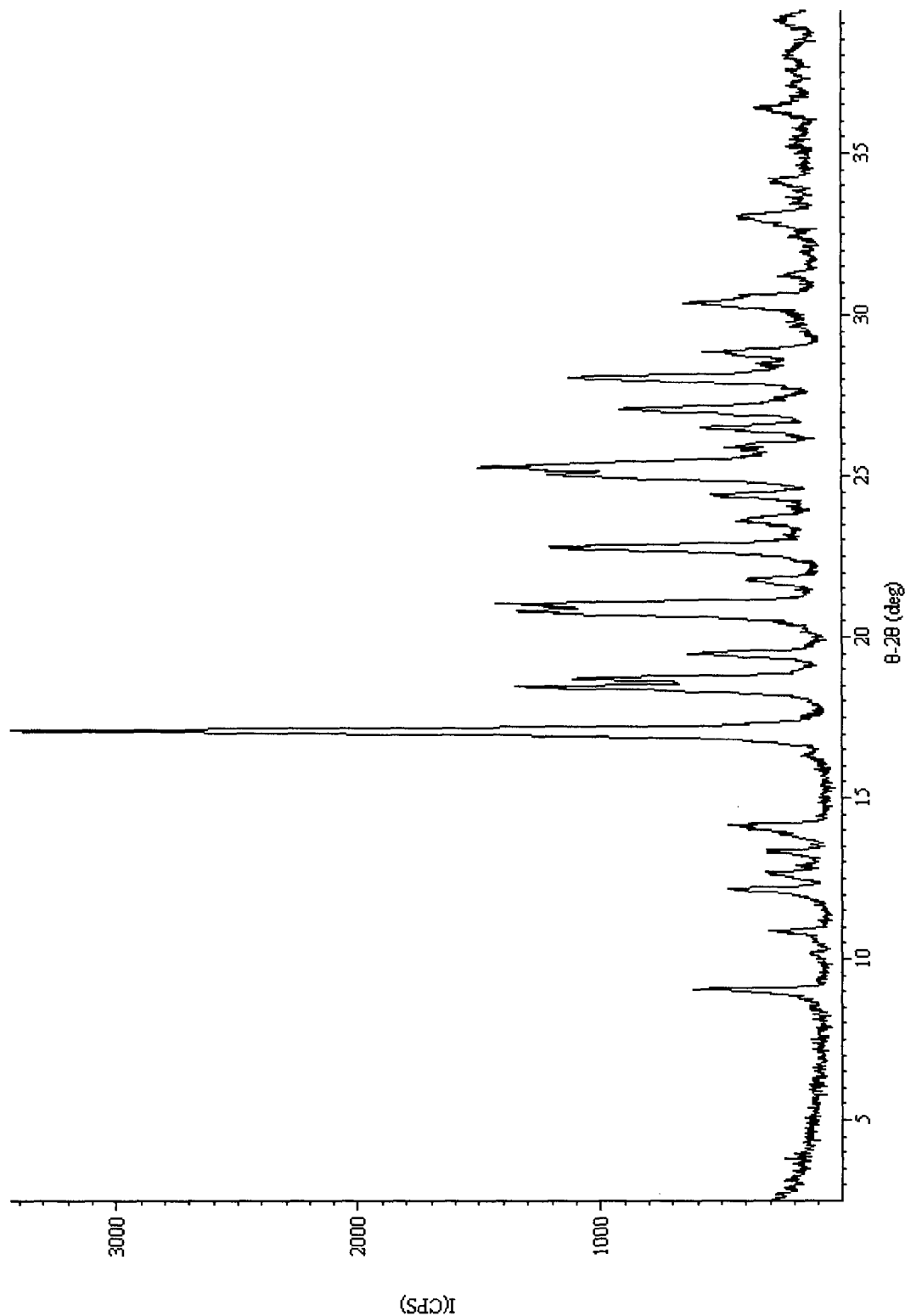
FIG. 1 depicts an XRPD spectrum consistent with Form A.

The present invention provides, inter alia, solid forms (Forms A-P) of the Raf kinase inhibitor 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine (see Example 17 for a general preparation of this compound). Each of the solid forms can be identified by one or more solid state analytical methods such as X-ray powder diffraction (XRPD), optionally in combination with thermal analysis by differential scanning calorimetry (DSC) and/or thermogravimetric analysis (TGA).

As used herein, the term "solid form" is meant to include any solid phase embodiment of the compound 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine, including both amorphous and crystalline solid forms. The term "solid form" is further meant to encompass both anhydrous and unsolvated solids as well as various hydrated and solvated forms.

Each of the solid forms described herein is characterized by an XRPD pattern. XRPD collection parameters are provided in Example 18. Generally, the relative intensities of the XRPD peaks can vary depending on, inter alia, the sample preparation technique, crystal size distribution, various filters used, the sample mounting procedure, and the particular instrument employed. Moreover, instrument variation and other factors can affect the 2-theta values. Accordingly, the term "substantially" in the context of XRPD is meant to encompass that peak assignments can vary by plus or minus about 0.2°. Moreover, new peaks may be observed or existing peaks may disappear, depending on the type of the machine or the settings used.

Representative XRPD patterns for each of Forms A-P are provided in the Figures and corresponding lists of 2-theta peaks, with intensities, are provided in Tables A-P. In some embodiments, the solid forms are characterized as having "substantially no peak" over a designated 2-theta region. In this context, the phrase "substantially no peak" is meant that there is no detectable peak in the designated region having an intensity of more than about 2% of the intensity of the strongest peak in the entire pattern.

The solid forms described herein are further characterized by DSC and TGA. Parameters for thermal data collection are provided in Example 19. The thermal value of DSC or TGA events can vary depending on, inter alia, the particle size distribution, the presence of impurities, the heating rate, and the type of instrument used. Accordingly, the temperature reading for DSC and TGA thermograms can vary about ±4° C., and thus a solid form having a DSC or TGA thermogram "substantially" as shown in a specified Figure is understood to accommodate such variation.

The solid forms can be prepared according to standard methods including, for example, precipitation from a solution containing 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine. Precipitation can be induced by any of many routine methods including temperature reduction (cooling), solvent evaporation, addition of antisolvent (e.g., directly, by layer diffusion or vapor diffusion), or combinations of these techniques. Alternatively, the solid forms can be made by slurrying solid 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine in organic or aqueous solvents.

Typically, different solid forms of the same substance have different bulk properties relating to, for example, hygroscopicity, solubility, stability, and the like. Forms with high melting points often have good thermodynamic stability which is advantageous in prolonging shelf-life drug formulations containing the solid form. Forms with lower melting points often are less thermodynamically stable, but are advantageous in that they have increased water solubility, translating to increased drug bioavailability. Forms that are weakly hygroscopic are desirable for their stability to heat and humidity and are resistant to degradation during long storage. Anhydrous forms are often desirable because they can be consistently made without concern for variation in weight or composition due to varying solvent or water content. On the other hand, hydrated or solvated forms can be advantageous in that they are less likely to be hygroscopic and may show improved stability to humidity under storage conditions.

The 16 solid forms of the invention are described in more detail below.

Solid Form A of 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine is a crystalline form characterized by an X-ray powder diffraction pattern comprising characteristic peaks, in terms of 2θ, at about 9.0°, about 17.0°, about 18.4°, and about 25.3°, wherein the pattern comprises no substantial peak at 2θ values below the peak at about 9.0°. In some embodiments, the pattern further comprises no substantial peak at 2θ values from about 14.5° to about 16.0°. In some embodiments, the pattern further comprises at least one characteristic peak, in terms of 2θ, at about 12.1°, about 14.1°, or about 18.7°. In some embodiments, pattern further comprises at least one characteristic peak, in terms of 2θ, at about 19.5°, about 21.8°, about 21.0°, about 22.7°, about 27.0°, or about 28.0°. In some embodiments, the solid form has an XRPD pattern substantially as shown in FIG. 1 (peaks are listed in Table A).

Figure 17:
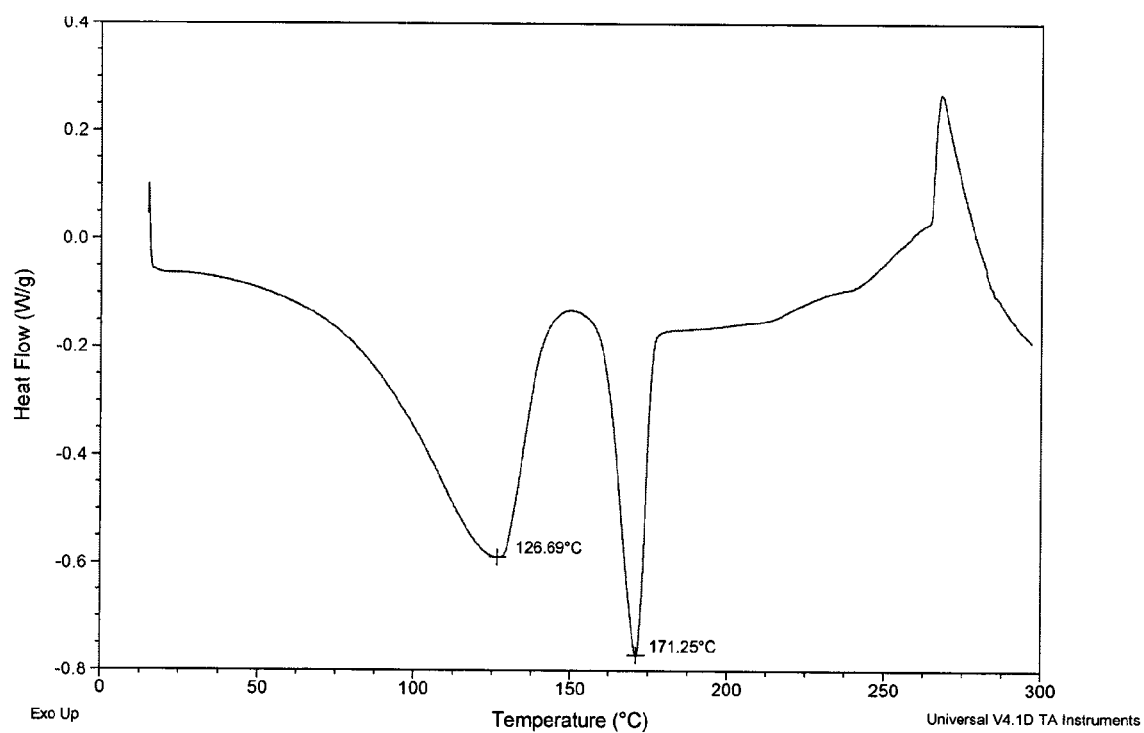
FIG. 17 depicts a DSC thermogram consistent with Form A.

In further embodiments, Form A is characterized by a DSC thermogram comprising endotherms at about 130 and about 170° C. In yet further embodiments, Form A is characterized by a DSC thermogram substantially as shown in FIG. 17.

TGA data related to Form A evidenced a hydrate or solvate. Typically, TGA revealed a 3-3.5% mass loss which is consistent with a monohydrate. Accordingly, the present invention includes hydrates of 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine, including the monohydrate form.

Form A can be prepared by precipitation of the form from a solution comprising an organic solvent and 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine. Suitable organic solvents include any organic solvent that is miscible with water and in which 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine is at least slightly soluble. Example organic solvents include nitriles (acetonitrile, propionitrile, etc.), alcohols (methanol, ethanol, etc.), acetic acid, ketones (acetone, methylethyl ketone, etc.), esters (ethyl acetate, etc.), halogenated hydrocarbons (methylene chloride, chlorobenzene, etc.), and mixtures thereof. In some embodiments, the precipitation is carried out in the presence of water. For example, the organic solvent can contain water or the precipitation can be carried out exposed to humid air.

Form A has numerous advantages that are readily apparent to the skilled artisan. For example, Form A can be obtained by precipitation from a variety of solvent conditions, indicating that it is a relatively stable form that would likely enjoy a relatively long shelf life. Additionally, because Form A is a hydrate, use of rigorously dry solvents, which can increase production costs, would not be required in the preparation, and exposure to humidity during storage would likely not be as much as a concern as for anhydrous or other forms.

Figure 2:
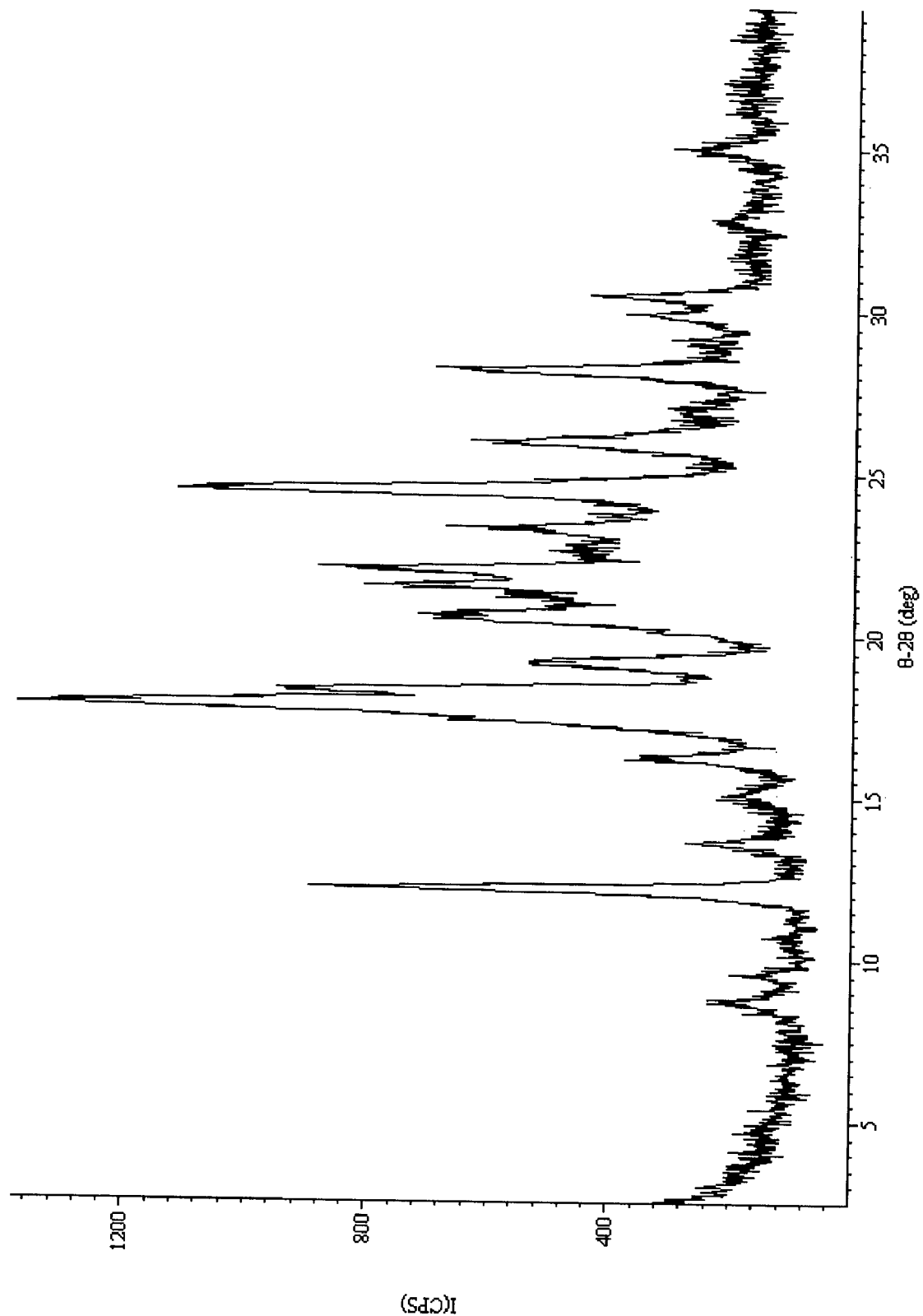
FIG. 2 depicts an XRPD spectrum consistent with Form B.

Form B of 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine is characterized as a crystalline form having an X-ray powder diffraction pattern comprising characteristic peaks, in terms of 2θ, at about 8.7°, about 12.2°, about 13.6°, about 17.9° and about 24.5°, wherein the pattern comprises no substantial peak at 2θ values below the peak at about 8.7°. In some embodiments, the pattern further comprises at least one characteristic peak, in terms of 2θ, at about 16.3°, about 19.2°, or about 20.6°. In some embodiments, the pattern further comprises at least one characteristic peak, in terms of 2θ, at about 21.8°, about 26.0°, about 28.2°, or about 30.2°. In some embodiments, the solid form has an XRPD pattern substantially as shown in FIG. 2 (peaks are listed in Table B).

Figure 18:
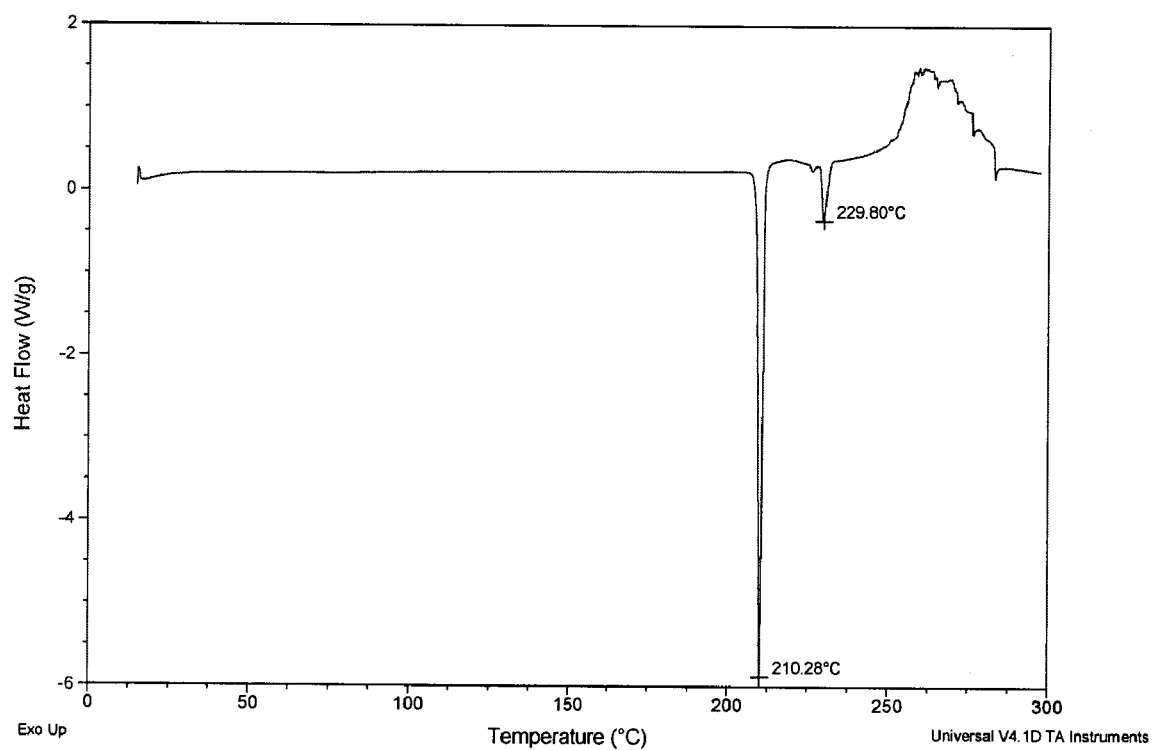
FIG. 18 depicts a DSC thermogram consistent with Form B.

In further embodiments, Form B is characterized by a DSC thermogram comprising an endotherm at about 210° C. In yet further embodiments, Form B is characterized by a DSC thermogram substantially as shown in FIG. 18.

Figure 34:
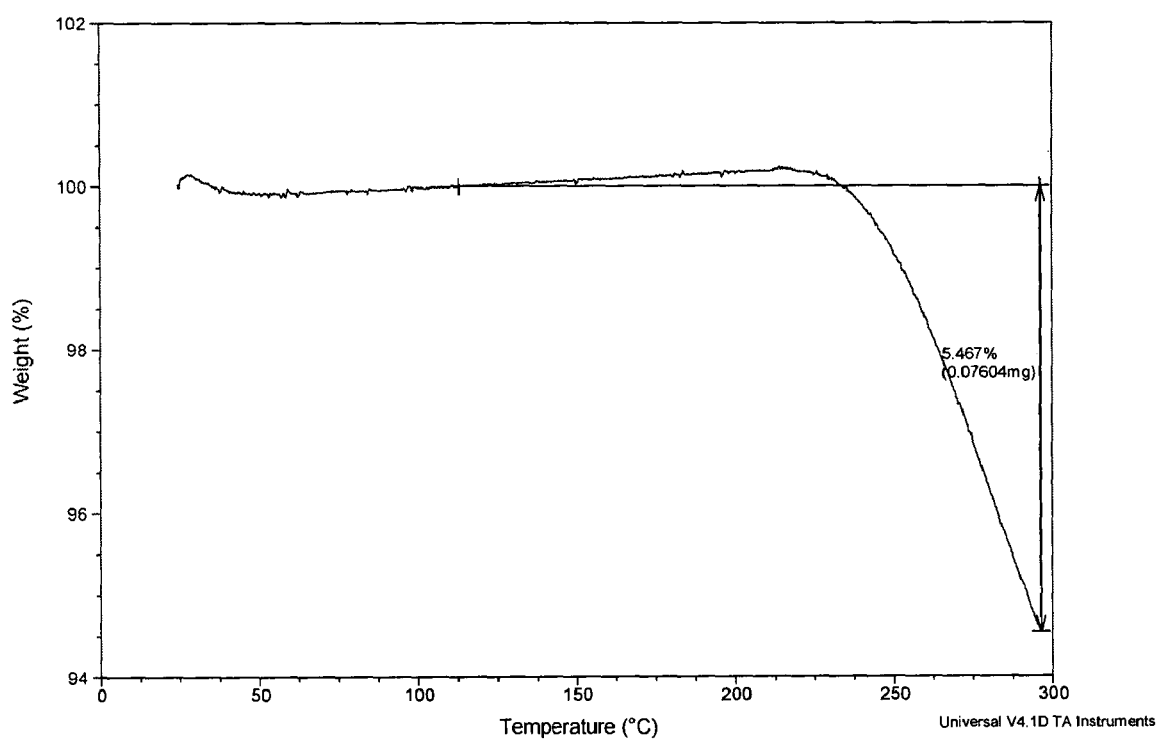
FIG. 34 depicts a TGA thermogram consistent with Form B.

Thermal analysis by TGA and DSC suggests that Form B is largely anhydrous and unsolvated. See FIG. 34 for TGA data characterizing Form B.

Form B can be prepared by any of numerous methods including precipitation of the solid form from a solution comprising an organic solvent and 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine. The organic solvent can include, for example, ketones (acetone, 2-butanone, methylethyl ketone, etc.), esters (ethyl acetate, etc.), ethers (diethyl ether, tetrahydrofuran, etc.) and mixtures thereof. In some embodiments, the organic solvent is substantially free of water.

The numerous advantages of Form B are readily apparent to the art skilled. For example, anhydrous and unsolvated solids are advantageous in that can be reproducibly formed without concern for variation in weight or composition due to varying solvent/water content.

Figure 3:
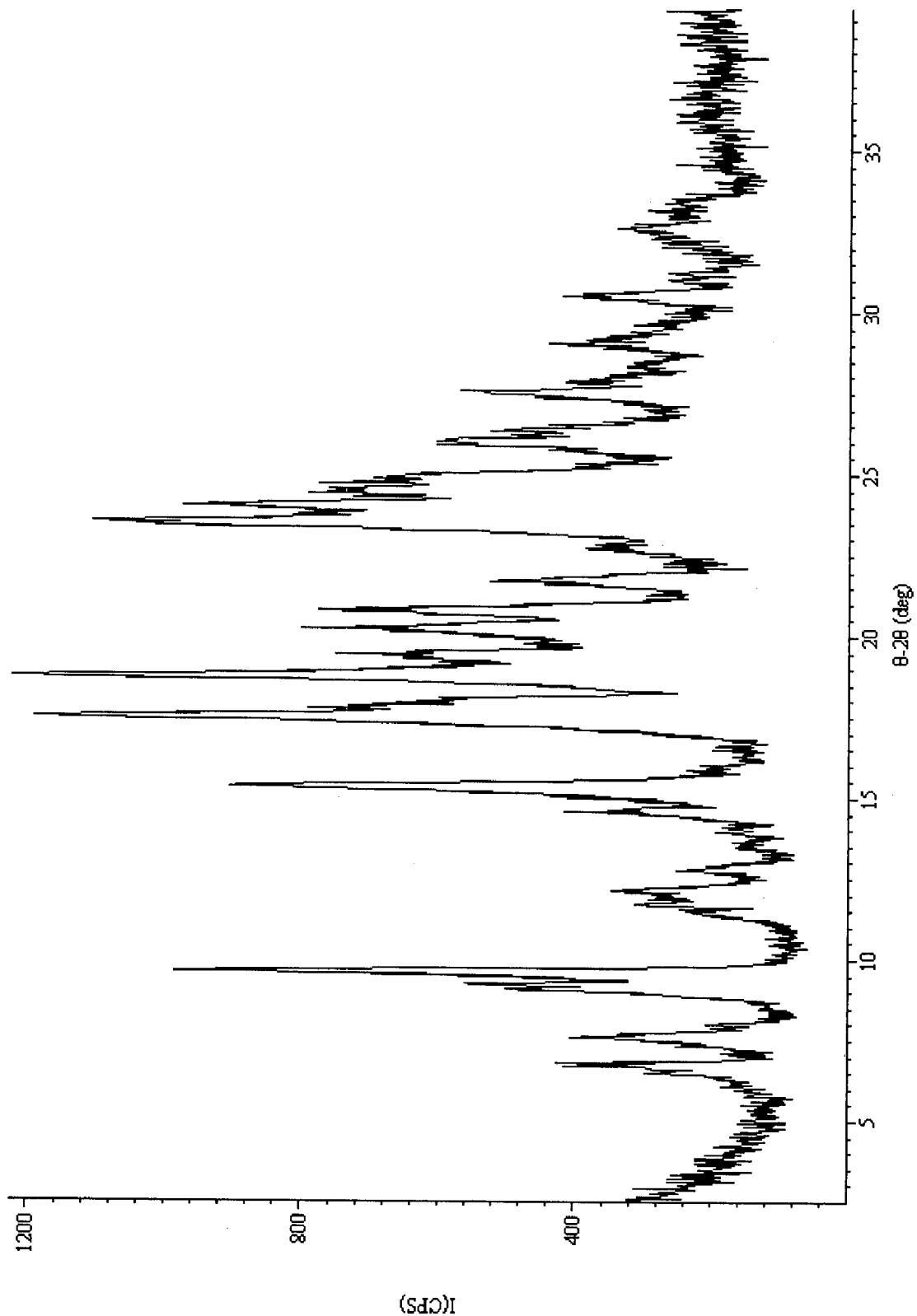
FIG. 3 depicts an XRPD spectrum consistent with Form C.

Form C is characterized as a crystalline form having an X-ray powder diffraction pattern comprising characteristic peaks, in terms of 2θ, at about 6.7°, about 7.6°, about 9.2°, about 9.6°, and about 15.3°, wherein the pattern comprises no substantial peak at 2θ values from about 9.8° to about 11.0°. In some embodiments, the pattern further comprises at least one characteristic peak, in terms of 2θ, at about 14.6°, about 17.6°, about 18.8°, about 19.4°, or about 20.2°. In further embodiments, the pattern further comprises at least one characteristic peak, in terms of 2θ, at about 20.8°, about 21.7°, about 23.5°, about 24.0°, about 26.1°, about 27.5°, about 29.1°, or about 30.5°. In yet further embodiments, the XRPD pattern is as substantially shown in FIG. 3 (peaks are listed in Table C).

Figure 19:
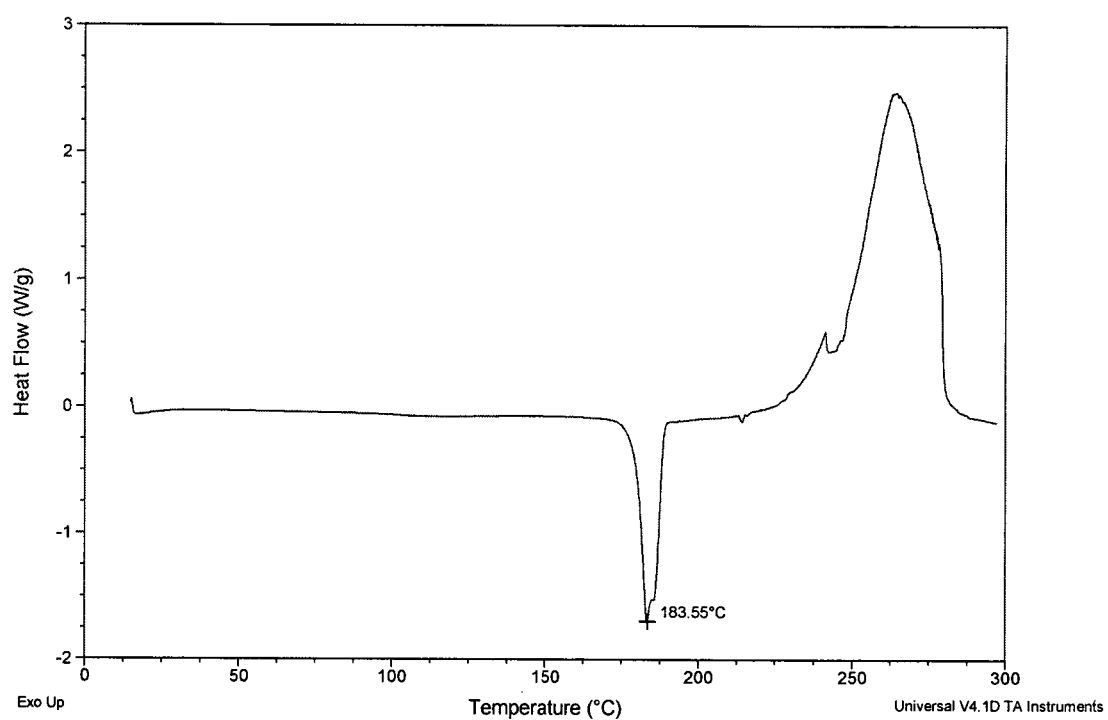
FIG. 19 depicts a DSC thermogram consistent with Form C.

In further embodiments, Form C is characterized by a DSC thermogram comprising an endotherm at about 183° C. In yet further embodiments, Form C is characterized by a DSC thermogram substantially as shown in FIG. 19.

Figure 35:
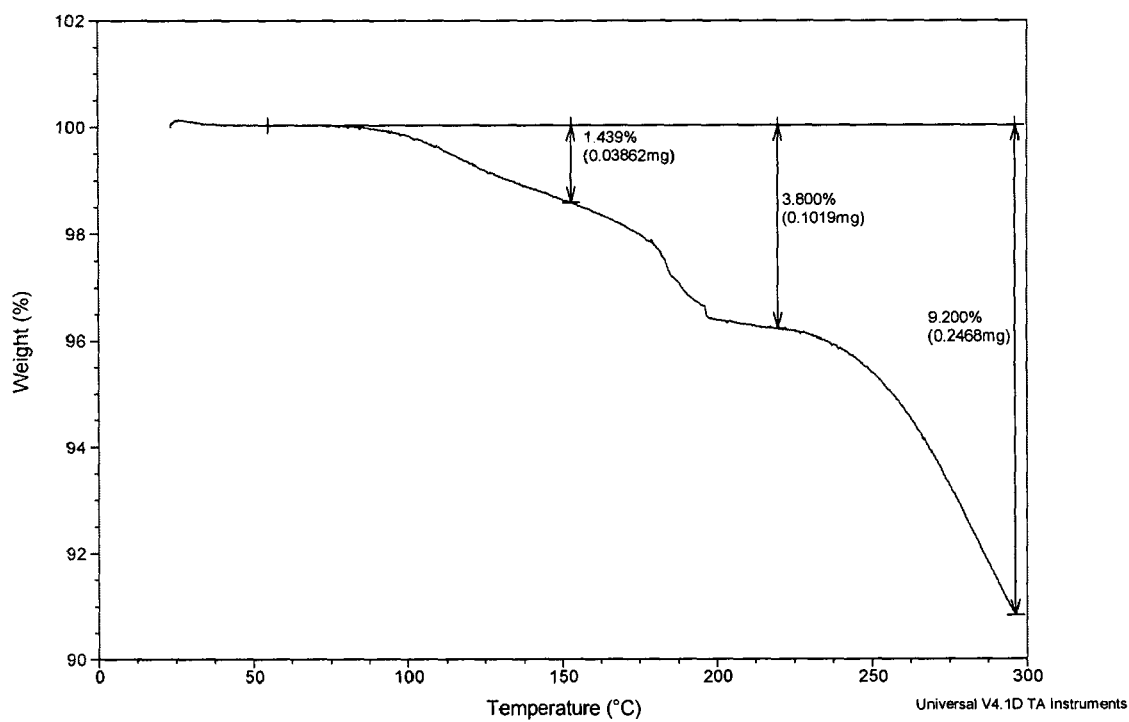
FIG. 35 depicts a TGA thermogram consistent with Form C.

Thermal analysis by DSC and TGA suggested that Form C is hydrated or solvated. Based on the TGA data (see FIG. 35), the sample lost about 3.8% of its original mass in what appeared to be three different steps.

Form C can be prepared by a plurality of methods including suspending 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine in an aliphatic hydrocarbon solvent (alkanes, alkenes, alkynes, etc.) or precipitating the solid form from a solution comprising an aliphatic hydrocarbon solvent (hexane, etc.) and 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine.

Figure 4:
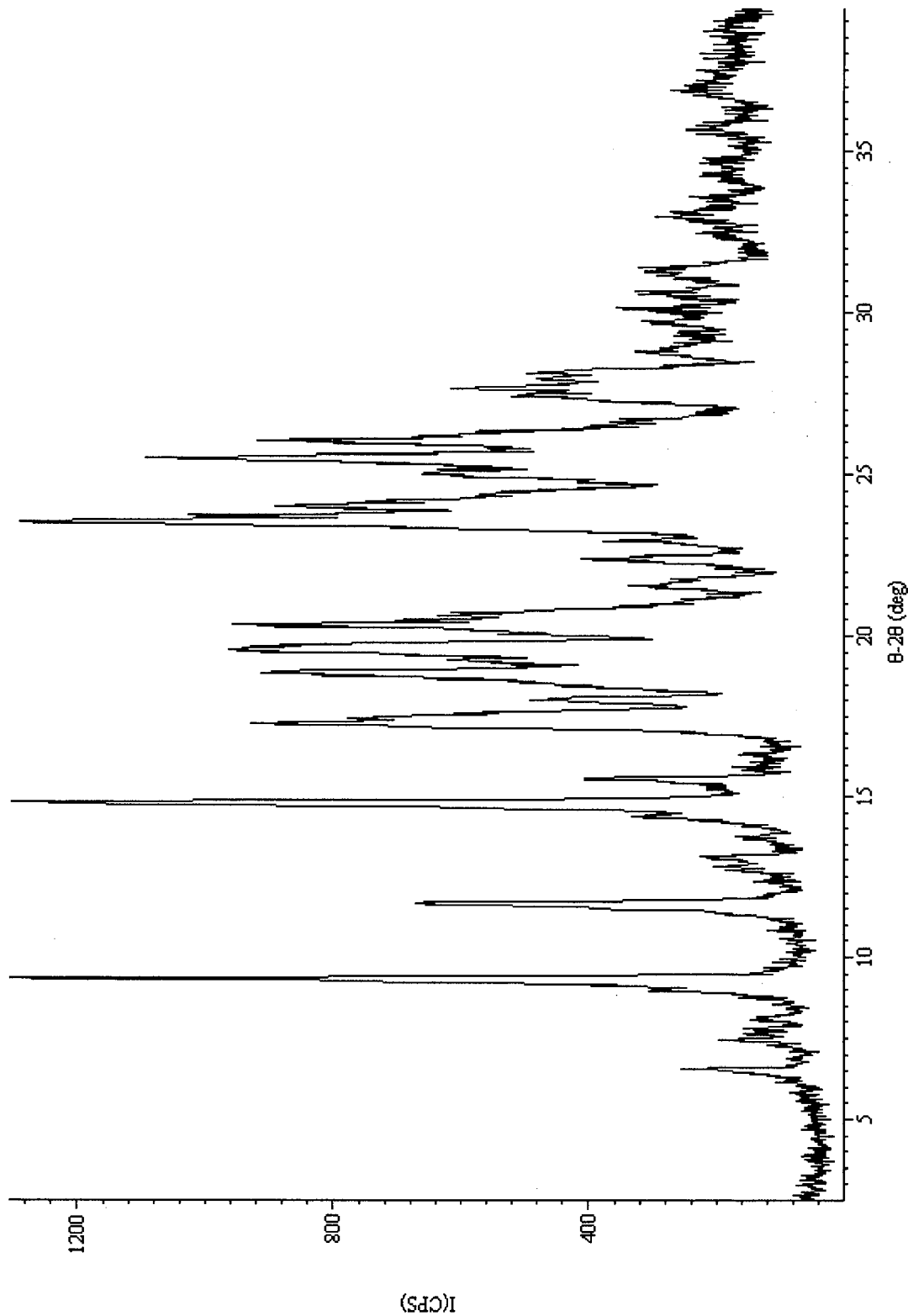
FIG. 4 depicts an XRPD spectrum consistent with Form D.

Form D is characterized as a crystalline form having an X-ray powder diffraction pattern comprising characteristic peaks, in terms of 2θ, at about 6.5° and about 11.6°. In some embodiments, the pattern further comprises at least one characteristic peak, in terms of 2θ, at about 7.5°, about 9.3°, about 14.8°, about 15.5°, about 17.4°. or about 18.0°. In further embodiments, the pattern further comprises at least one characteristic peak, in terms of 2θ, at about 18.8°, about 19.6°, about 20.3°, about 22.3°, about 23.5°, about 24.4°, about 25.4°, about 26.0°, or about 27.7°. In some embodiments, the XRPD pattern is as substantially shown in FIG. 4 (peaks are listed in Table D).

Figure 20:
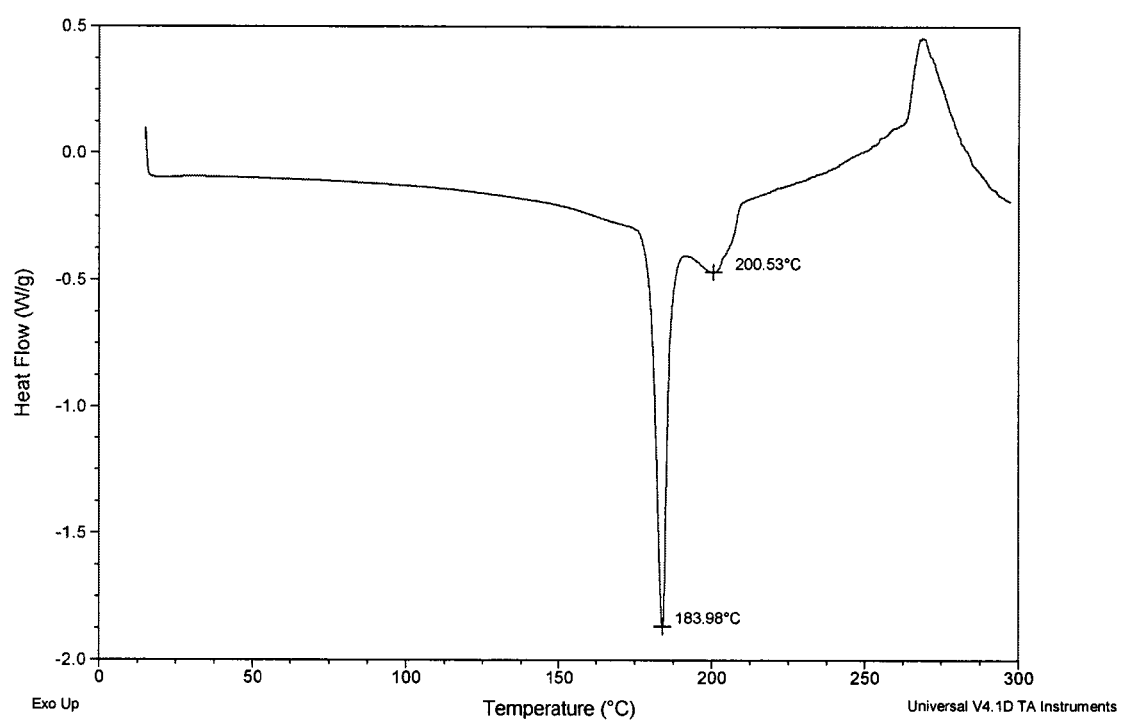
FIG. 20 depicts a DSC thermogram consistent with Form D.

In further embodiments, Form D is characterized by a DSC thermogram comprising an endotherm at about 184° C. In yet further embodiments, Form D is characterized by a DSC thermogram substantially as shown in FIG. 20.

Figure 36:
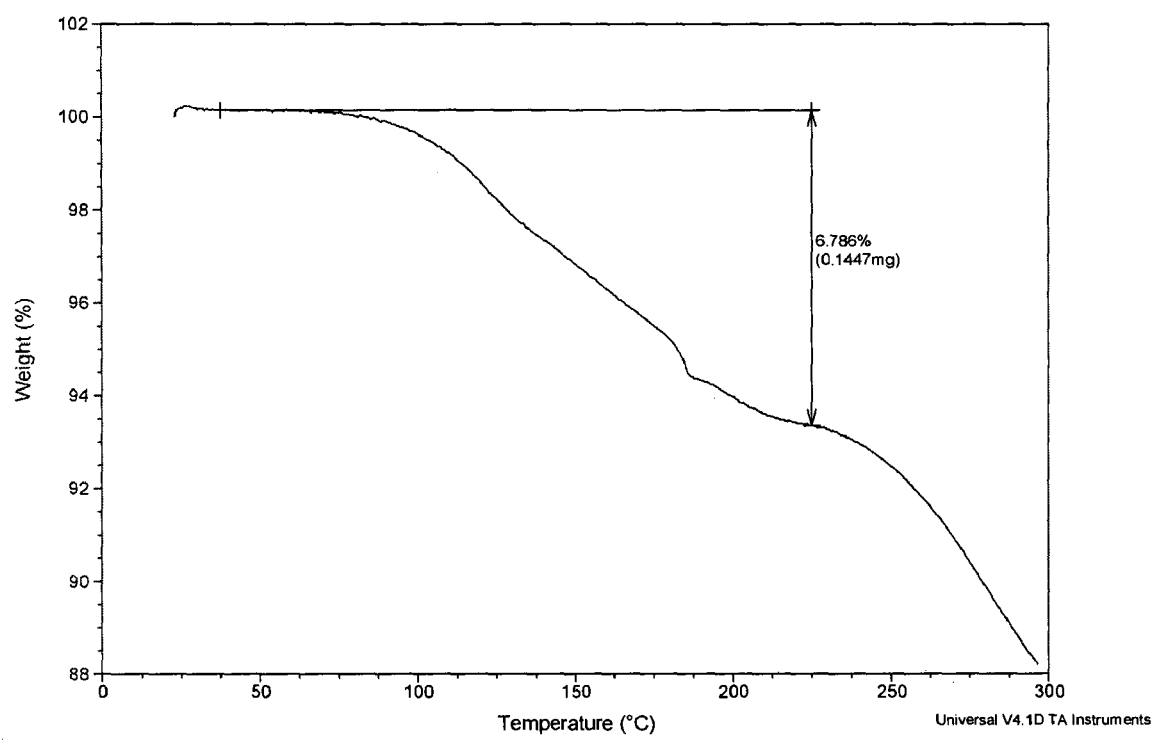
FIG. 36 depicts a TGA thermogram consistent with Form D.

Thermal analysis by TGA and DSC suggest that Form D is hydrated or solvated. Based on the TGA data (see FIG. 36), the sample lost a total about 6.79% of its original mass between ambient temperature and 225° C.

Form D can be prepared by any of the various methods comprising suspending 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine in an aromatic hydrocarbon solvent (toluene, etc.) or precipitating the solid form from a solution comprising an aromatic hydrocarbon solvent (toluene, etc.) and 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine.

Figure 5:
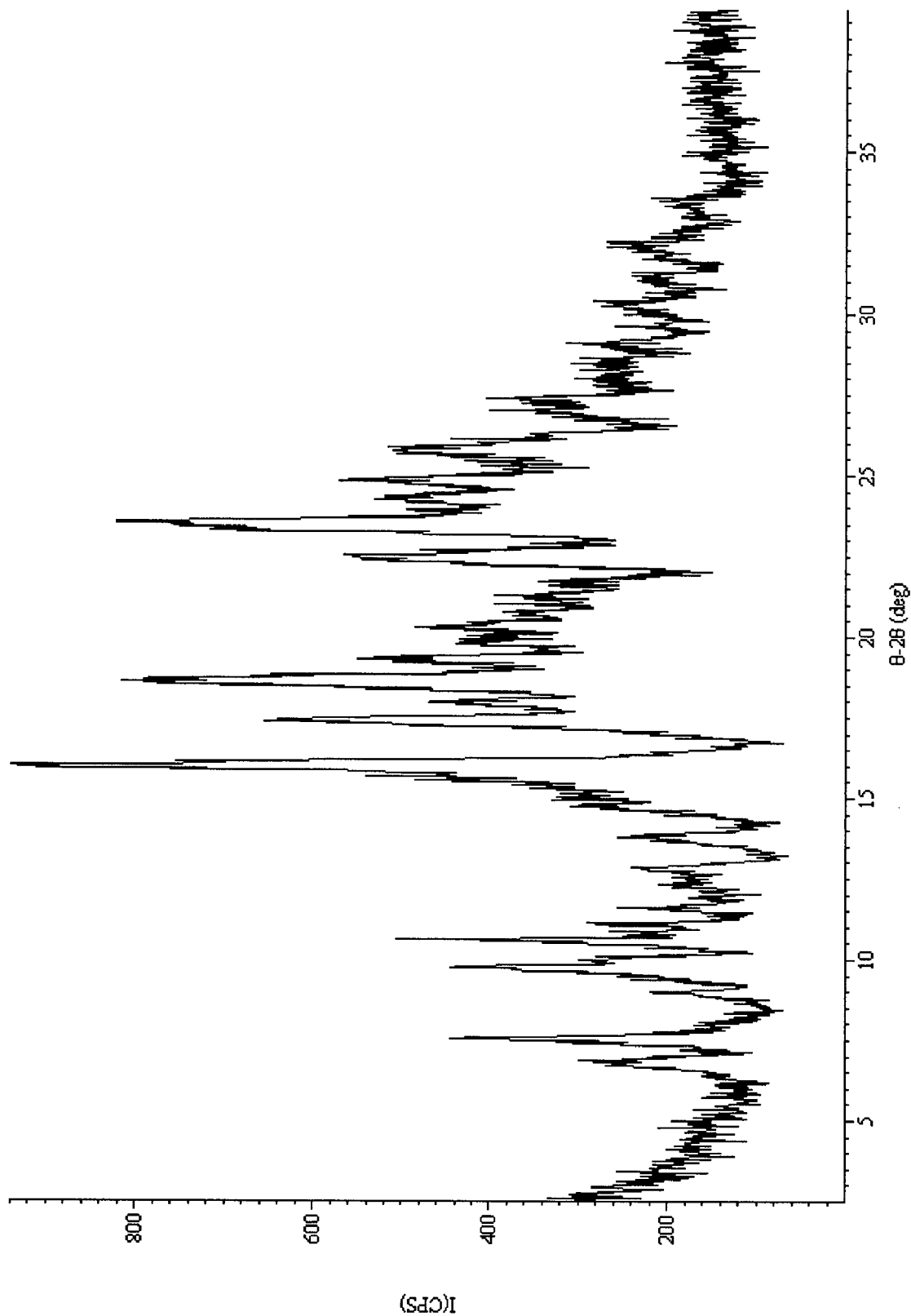
FIG. 5 depicts an XRPD spectrum consistent with Form E.

Form E is characterized as a crystalline form having an X-ray powder diffraction pattern comprising characteristic peaks, in terms of 2θ, at about 7.5° and about 10.6°. In some embodiments, the pattern further comprises at least one characteristic peak, in terms of 2θ, at about 6.8°, about 9.8°, about 10.6°, or about 16.0°. In further embodiments, the pattern further comprises at least one characteristic peak, in terms of 2θ, at about 17.4°, about 18.6°, about 19.3°, about 22.5°, about 23.5°, about 24.8°, or about 25.8°. In yet further embodiments, Form E has an XRPD pattern substantially as shown in FIG. 5 (peaks are listed in Table E).

Figure 21:
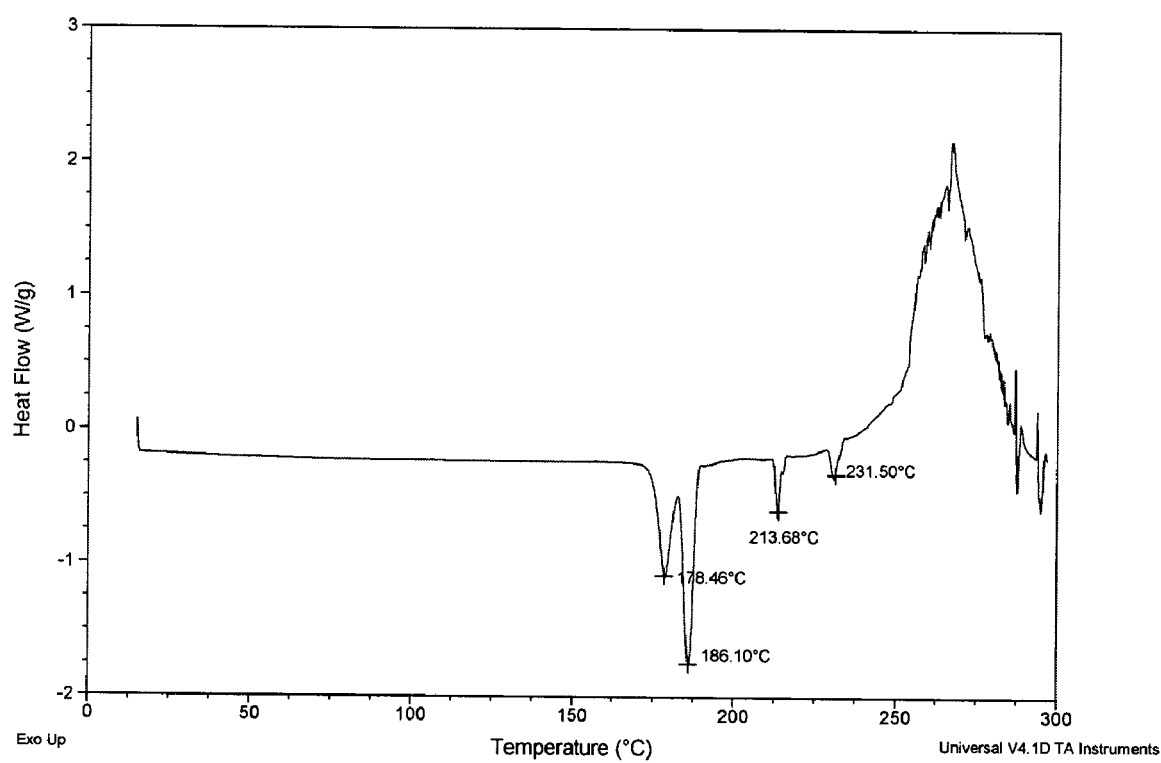
FIG. 21 depicts a DSC thermogram consistent with Form E.

In further embodiments, Form E is characterized by a DSC thermogram comprising endotherms at about 179 and about 186° C. In yet further embodiments, Form E is characterized by a DSC thermogram substantially as shown in FIG. 21.

Thermal analysis by TGA and DSC suggest that Form E is an anhydrate or is unsolvated. See FIG. 37 for TGA data characterizing Form E.

Form E can be prepared by various methods. For example, 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine can be dissolved in an alcohol, such as ethanol, optionally under reflux, to achieve a homogeneous solution. Then the alcohol can be removed by, for example, distillation resulting in a slurry that can be treated with water and cooled. The solid product can be isolated, washed, and dried under vacuum until constant weight.

Figure 6:
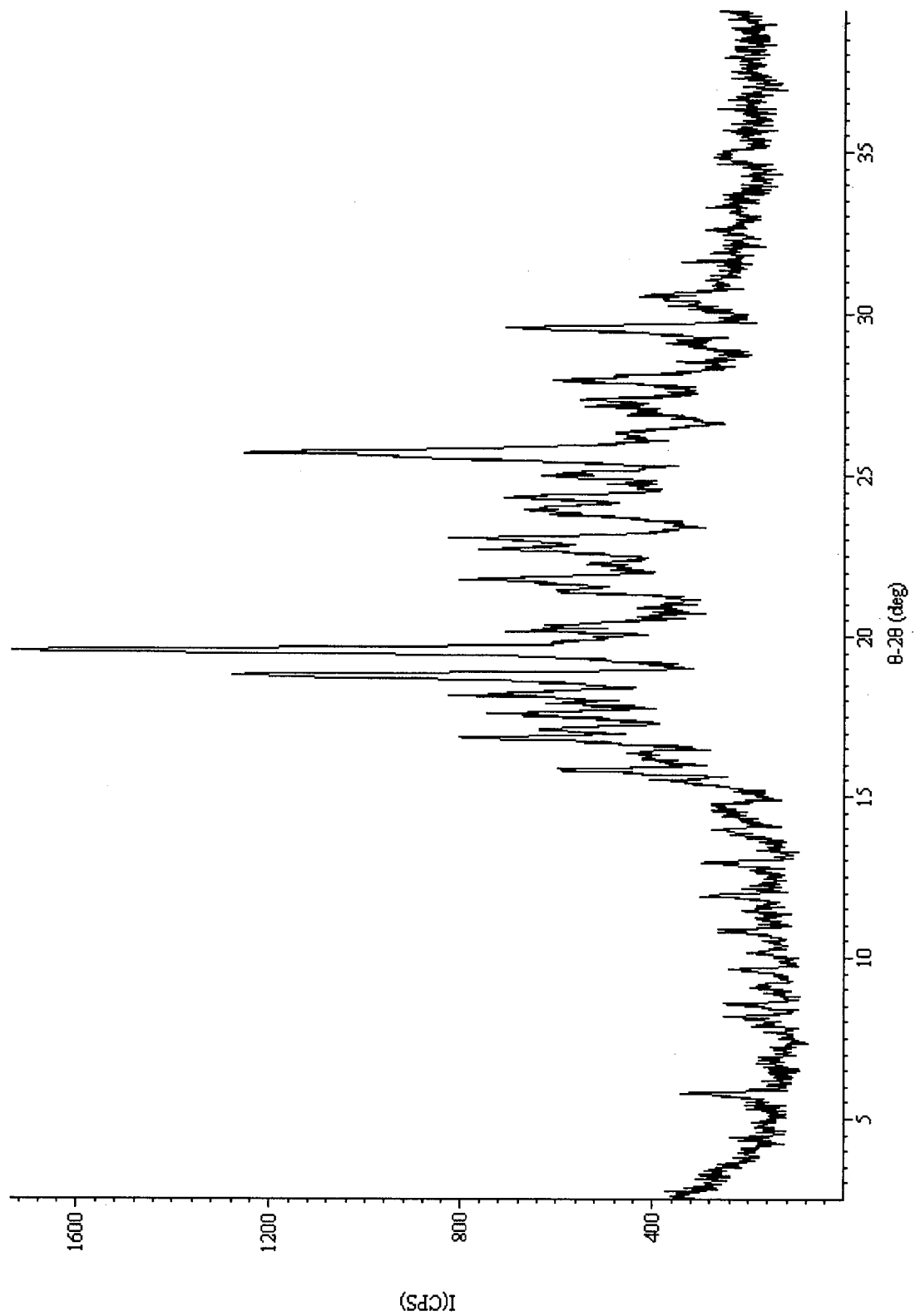
FIG. 6 depicts an XRPD spectrum consistent with Form F.

Form F of 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine is characterized as a crystalline form having an X-ray powder diffraction pattern comprising characteristic peaks, in terms of 2θ, at about 5.8° and about 19.6°. In some embodiments, the pattern further comprises at least one characteristic peak, in terms of 2θ, at about 15.8°, about 16.8°, about 17.5°, about 18.2°, or about 18.8°. In some embodiments, the pattern further comprises at least one characteristic peak, in terms of 2θ, at about 20.3°, about 21.7°, about 22.7°, about 23.0°, about 24.3°, about 25.7°, about 27.9°, or about 29.5°. In further embodiments, the XRPD pattern is as substantially shown in FIG. 6 (peaks are listed in Table F).

Figure 22:
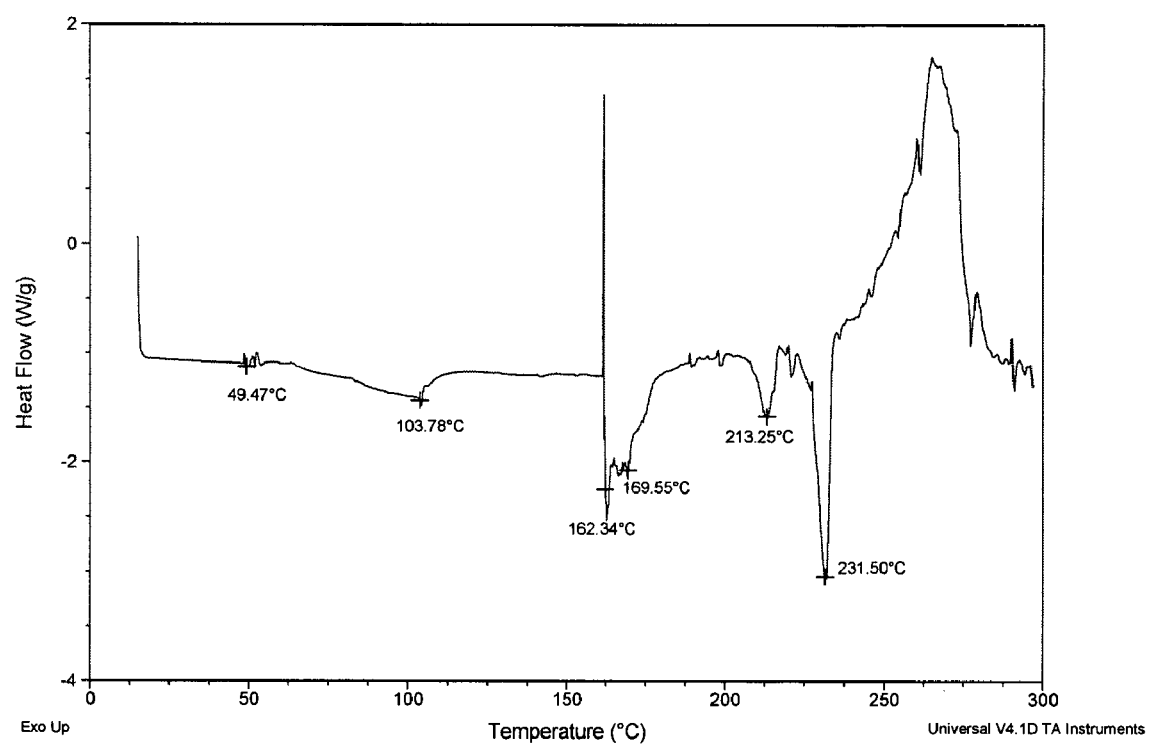
FIG. 22 depicts a DSC thermogram consistent with Form F.

In further embodiments, Form F is characterized by a DSC thermogram substantially as shown in FIG. 22.

Figure 38:
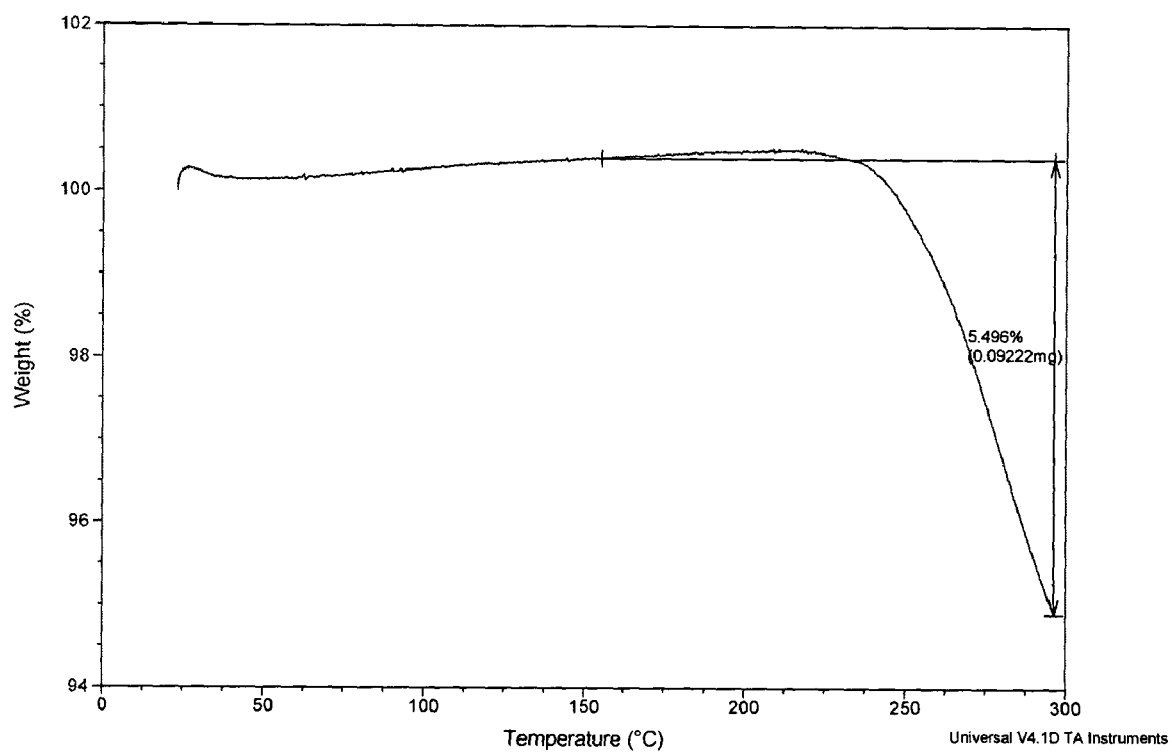
FIG. 38 depicts a TGA thermogram consistent with Form F.

Thermal analysis by TGA and DSC suggest that Form F is an anhydrate or is unsolvated. See FIG. 38 for TGA data characterizing Form F.

Form F can be prepared by numerous methods comprising heating 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine to a temperature of about 200 to 230° C. followed by cooling or suspending the product of the above process in an organic solvent followed by cooling and precipitation. The organic solvent can comprise ethyl acetate or other organic ester.

Figure 7:
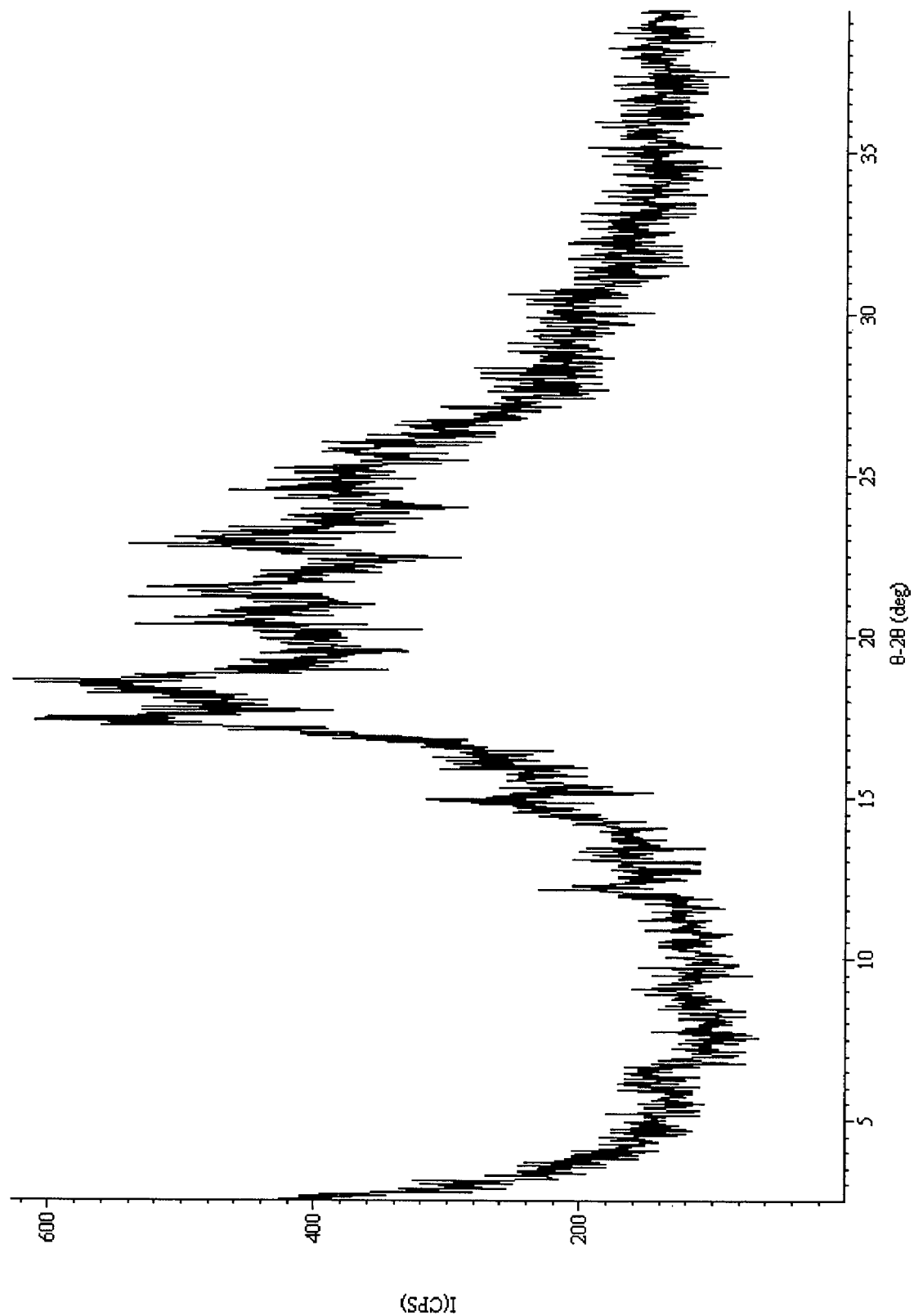
FIG. 7 depicts an XRPD spectrum consistent with Form G.
Figure 23:
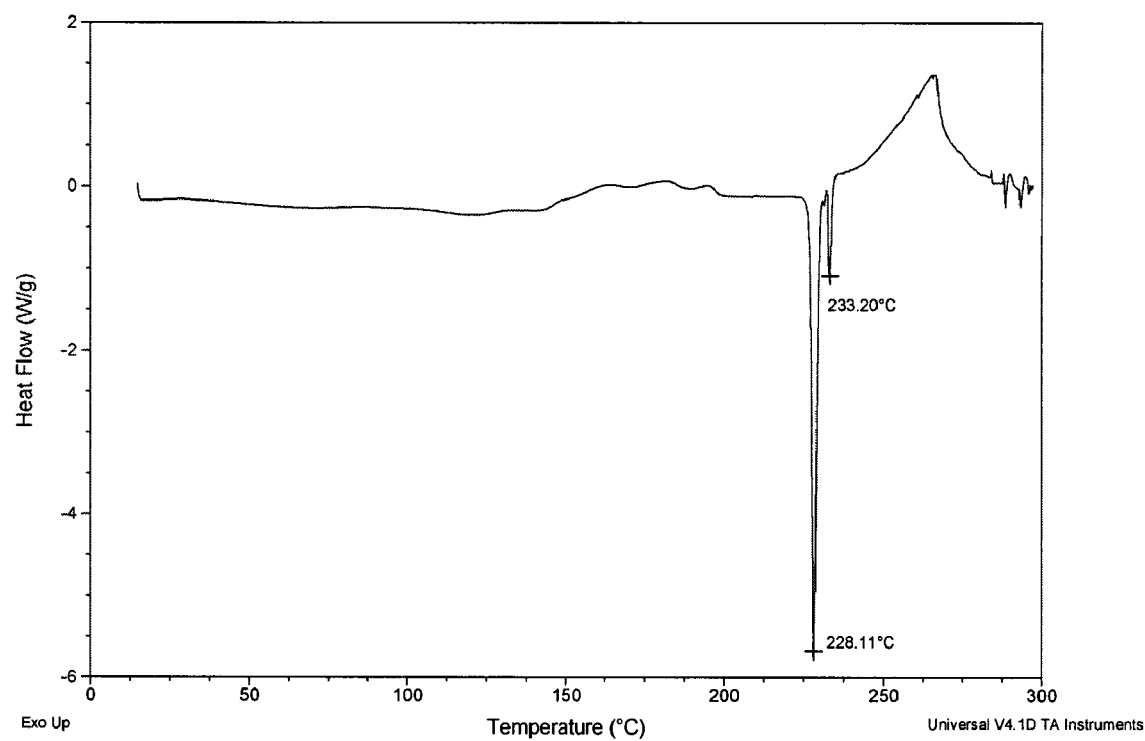
FIG. 23 depicts a DSC thermogram consistent with Form G.

Form G of 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine is characterized as an amorphous or a nanocrystalline form having an X-ray powder diffraction pattern substantially as shown in FIG. 7 (peaks are listed in Table G). In further embodiments, Form G is characterized by a DSC thermogram comprising an endotherm at about 228° C. In yet further embodiments, Form G is characterized by a DSC thermogram substantially as shown in FIG. 23.

Figure 39:
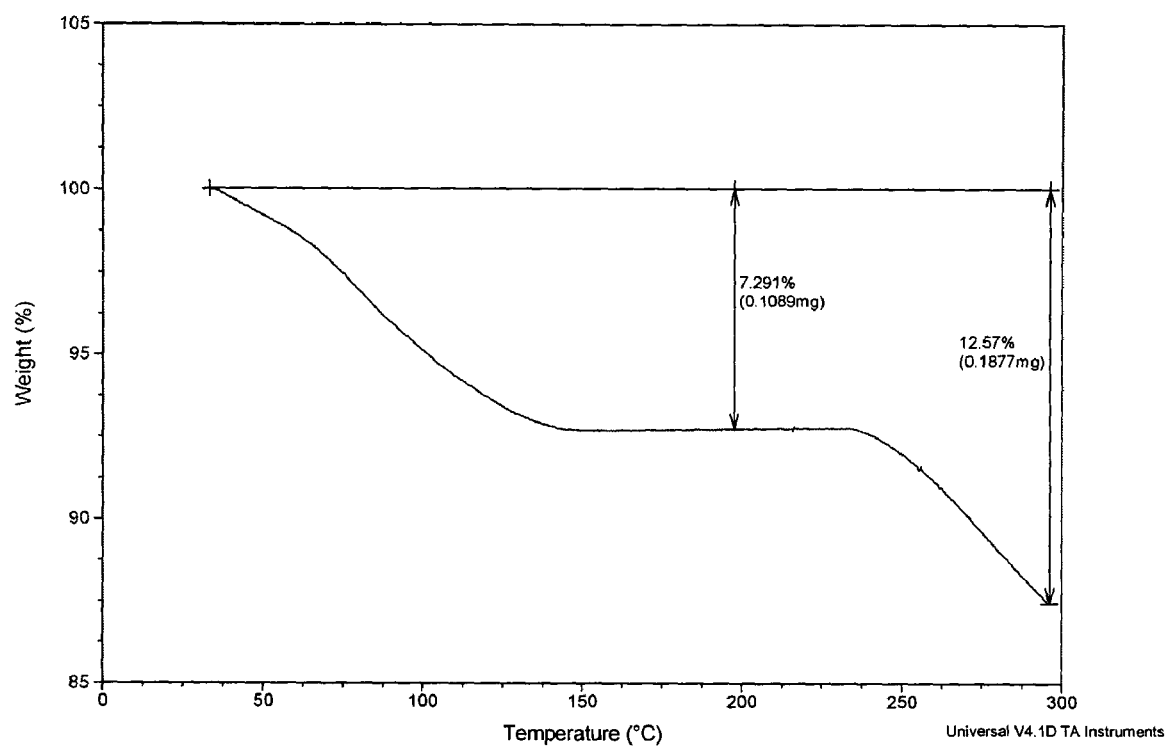
FIG. 39 depicts a TGA thermogram consistent with Form G.

In further embodiments, Form G is characterized by a TGA thermogram substantially as shown in FIG. 39.

Form G can be prepared via a process comprising precipitating the solid form from a solution comprising an organic solvent such as an ether (e.g. tetrahydrofuran) and 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine.

Figure 8:
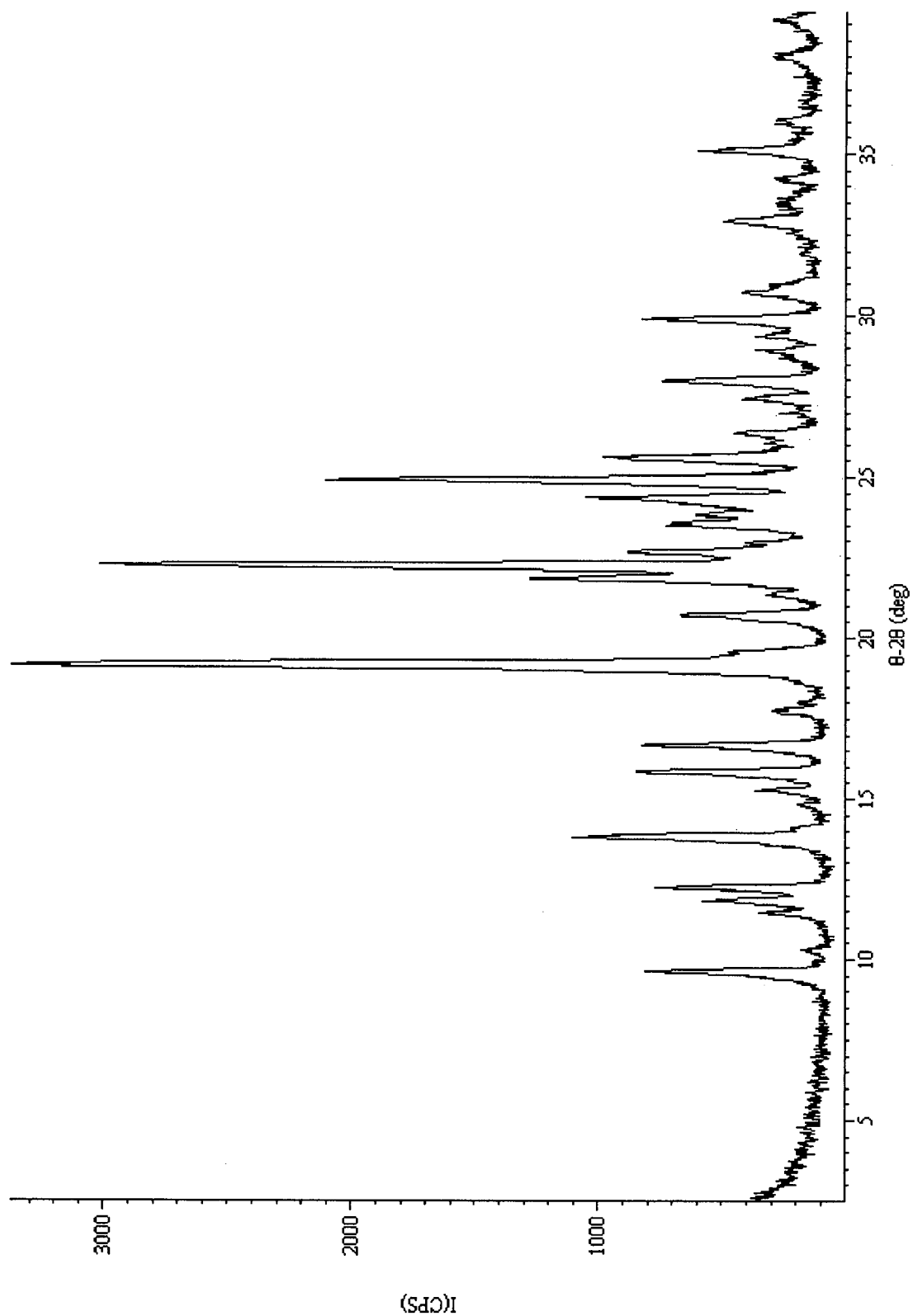
FIG. 8 depicts an XRPD spectrum consistent with Form H.

Form H is characterized as a crystalline form having an X-ray powder diffraction pattern comprising characteristic peaks, in terms of 2θ, at about 9.6°, about 13.8°, and about 12.2°, wherein the pattern comprises no substantial peak at 2θ values less than about 9.0°. In some embodiments, the pattern further comprises at least one characteristic peak, in terms of 2θ, at about 11.5°, about 11.8°, about 15.8°, about 16.7°, or about 19.2°. In some embodiments, the pattern further comprises at least one characteristic peak, in terms of 2θ, at about 20.7°, about 21.8°, about 22.2°, about 22.6°, about 24.3°, about 24.9°, about 25.6°, about 28.0°, about 29.9°, about 32.9°, or about 35.1°. In some embodiments, the solid form (Form H) has a powder X-ray diffraction pattern substantially as shown in FIG. 8 (peaks are listed in Table H).

Figure 24:
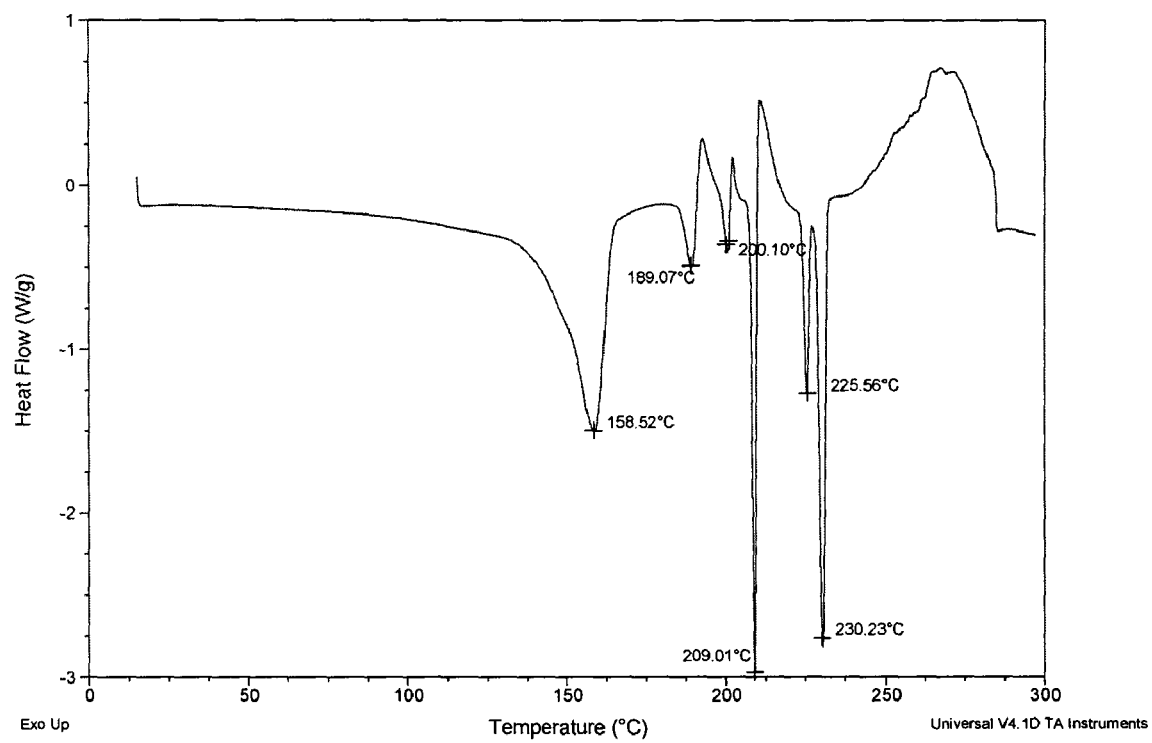
FIG. 24 depicts a DSC thermogram consistent with Form H.

In further embodiments, the solid form is characterized by a DSC thermogram comprising an endotherm at about 159° C. In yet further embodiments, the form is characterized by a DSC thermogram substantially as shown in FIG. 24.

Figure 40:
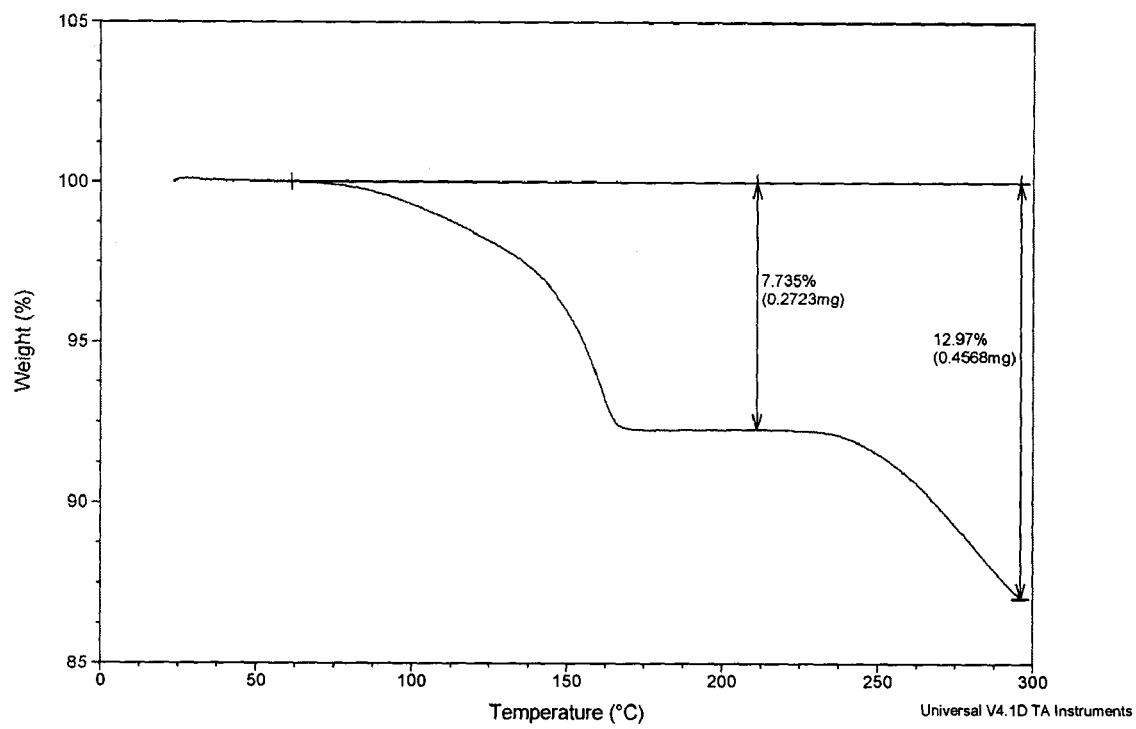
FIG. 40 depicts a TGA thermogram consistent with Form H.

TGA data of Form H evidenced a hydrate or solvate. Typically, TGA (FIG. 40) revealed a 6-8% mass loss which is consistent with an ethanol solvate consisting of about one mole of ethanol per one mole of 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine.

Form H can be prepared by cooling or evaporating a solution comprising 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine and alcohol such as ethanol.

Figure 9:
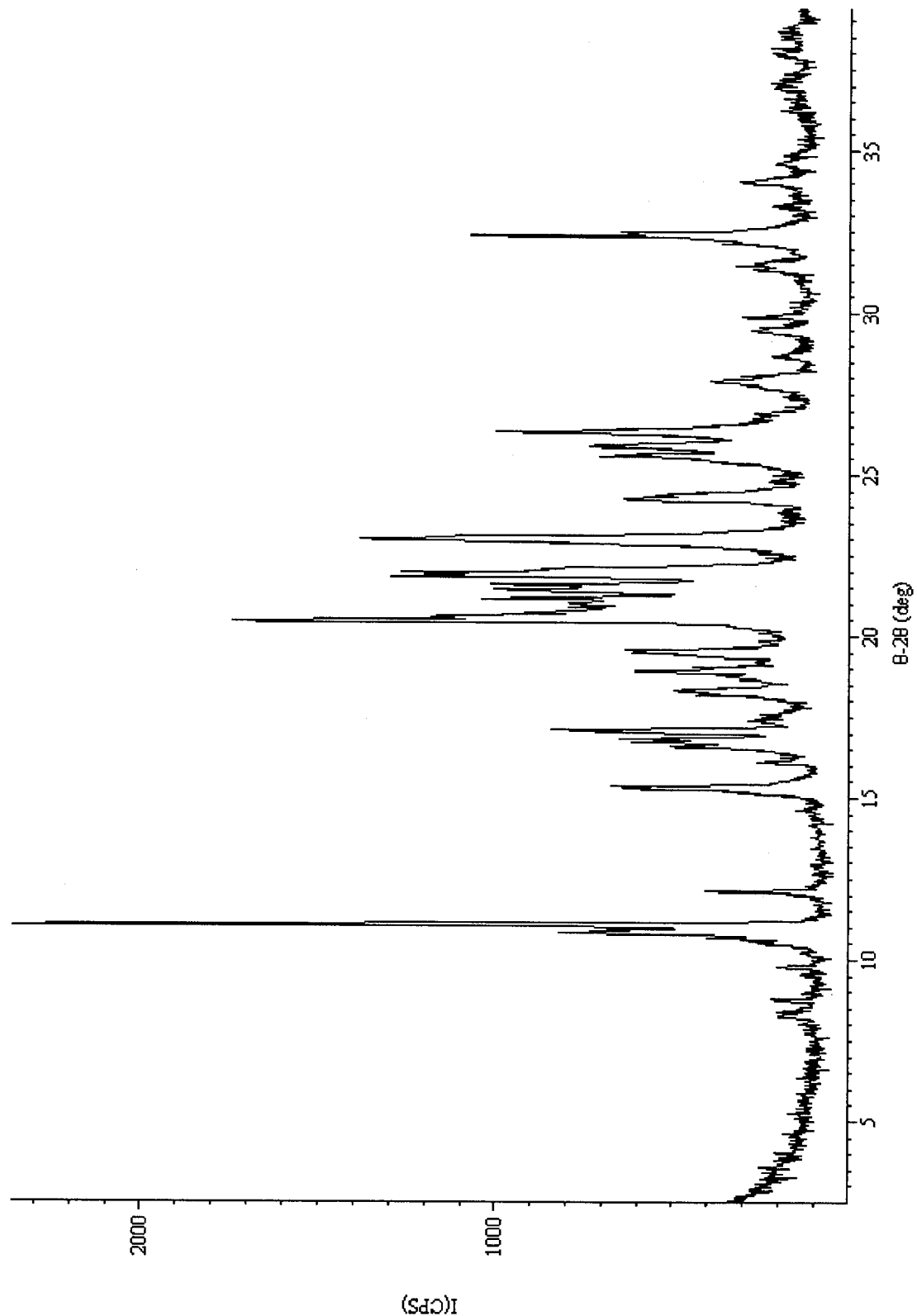
FIG. 9 depicts an XRPD spectrum consistent with Form I.

Form I is characterized as a crystalline form having an X-ray powder diffraction pattern comprising characteristic peaks, in terms of 2θ, at about 11.1° and about 32.4°, wherein the pattern comprises no substantial peak at 2θ values of about 12.5° to about 14.5°. In some embodiments, the pattern further comprises at least one characteristic peak, in terms of 2θ, at about 12.1°, about 15.3°, about 17.1°, about 18.9°, or about 19.5°. In some embodiments, the pattern further comprises at least one characteristic peak, in terms of 2θ, at about 20.5°, about 21.9°, about 22.1°, about 24.3°, about 26.3°, or about 27.9°. In some embodiments, Form I is characterized by an XRPD pattern substantially as shown in FIG. 9 (peaks are listed in Table I).

Figure 25:
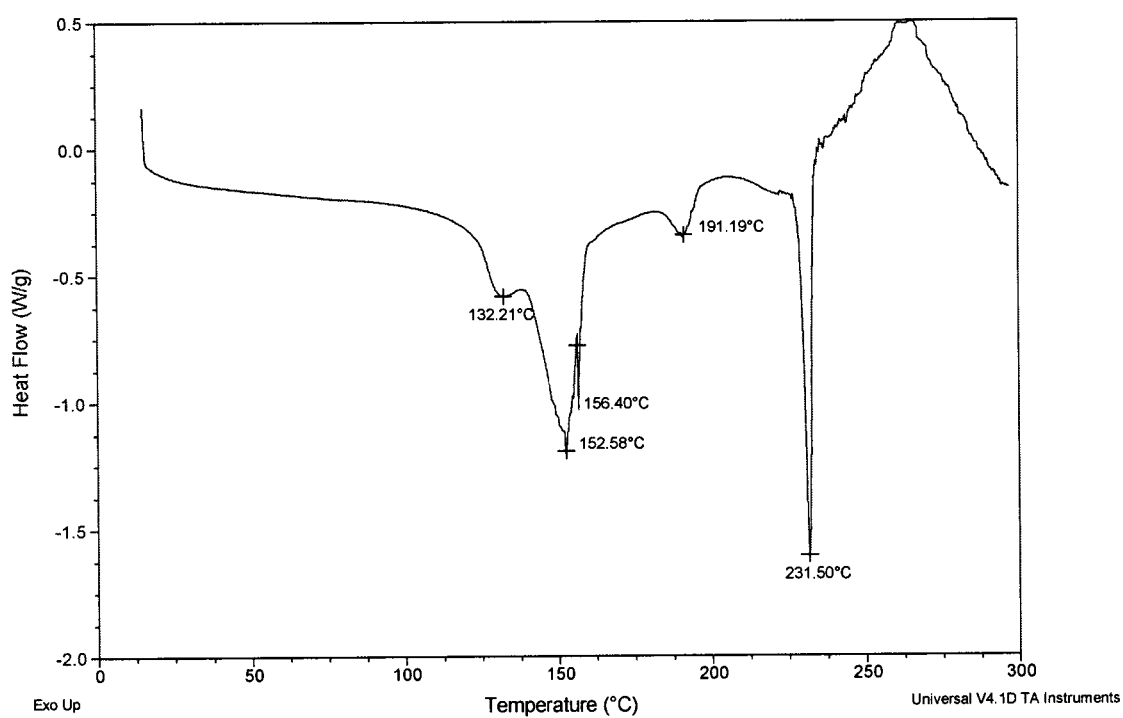
FIG. 25 depicts a DSC thermogram consistent with Form I.

In further embodiments, Form I is characterized by a DSC thermogram comprising an endotherm at about 232° C. In yet further embodiments, Form I exhibits a DSC thermogram substantially as shown in FIG. 25.

Figure 41:
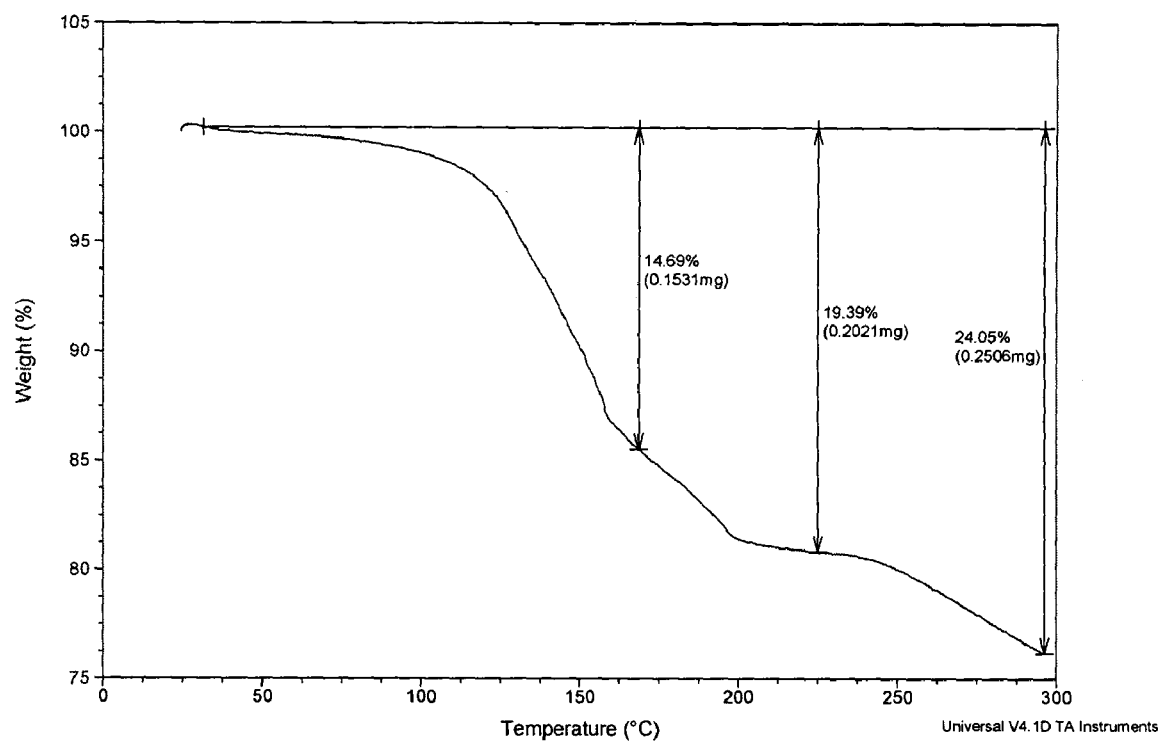
FIG. 41 depicts a TGA thermogram consistent with Form I.

Thermal analysis by TGA and DSC suggest that Form I is a hydrate or solvate. See FIG. 41 for TGA data characterizing Form I.

Form I can be prepared by precipitating the solid form from a solution comprising 1-methyl-5-(2-(5-(trifluoromethyl)-1H-imidazol-2-yl)pyridin-4-yloxy)-N-(4-(trifluoromethyl) phenyl)-1H-benzo[d]imidazol-2-amine and dioxane. Precipitation can comprise cooling and evaporation crystallization of the solid form from dioxane solution.

Figure 10:
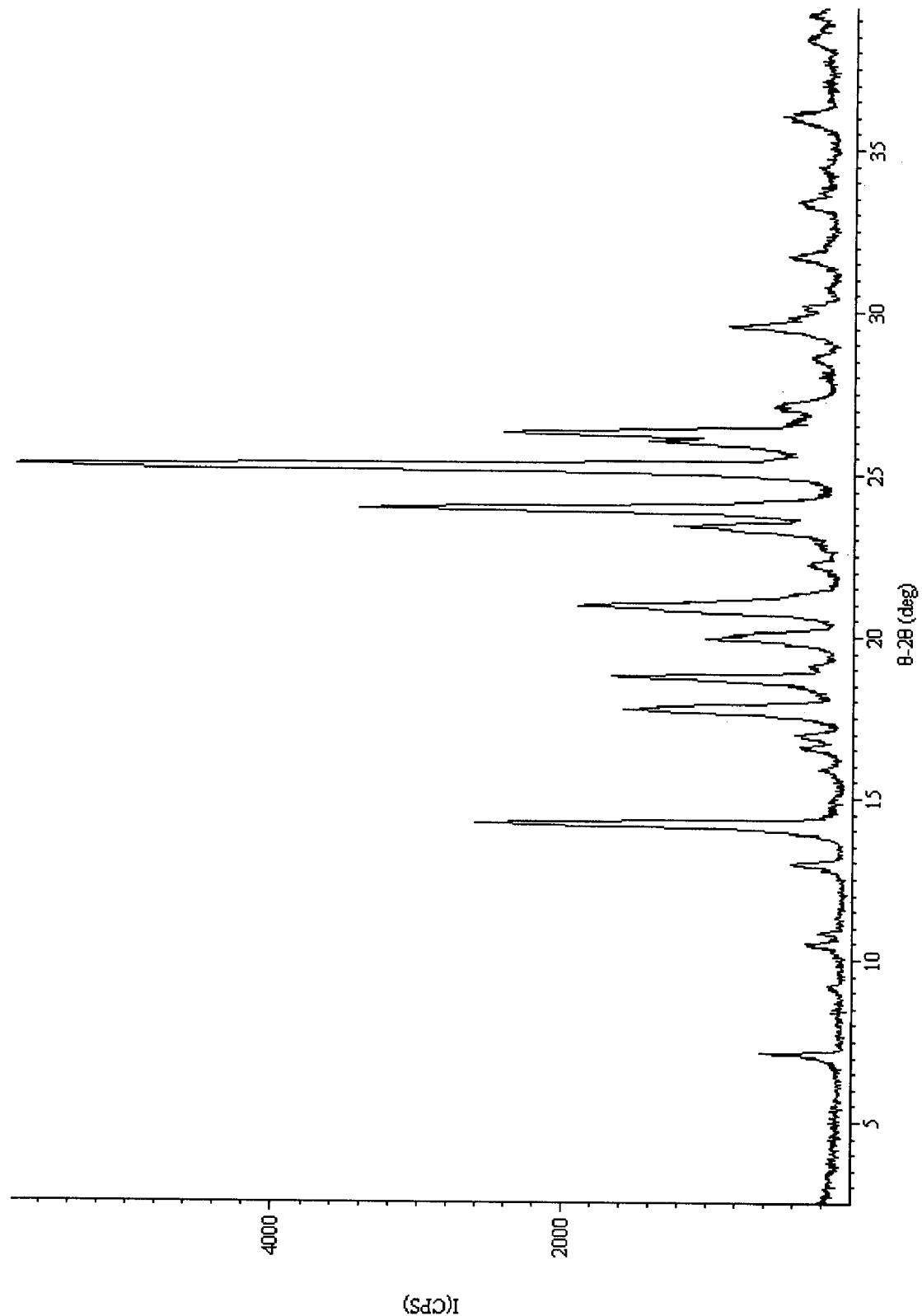
FIG. 10 depicts an XRPD spectrum consistent with Form J.

Form J is characterized as a crystalline form having an X-ray powder diffraction pattern comprising characteristic peaks, in terms of 2θ, at about 7.1°, about 14.2°, and about 29.5°, wherein the pattern comprises no substantial peak at 2θ values of about 11.0° to about 12.5°. In some embodiments, the pattern further comprises at least one characteristic peak, in terms of 2θ, at about 10.5°, about 12.9°, about 17.8°, about 18.7°, or about 20.0°. In further embodiments, the pattern further comprises at least one characteristic peak, in terms of 2θ, at about 20.9°, about 23.4°, about 23.9°, about 25.2°, about 26.3°, about 31.7°, about 33.3°, or about 36.0°. In yet further embodiments, Form J is characterized by a powder X-ray diffraction pattern substantially as shown in FIG. 10 (peaks are listed in Table J).

Figure 26:
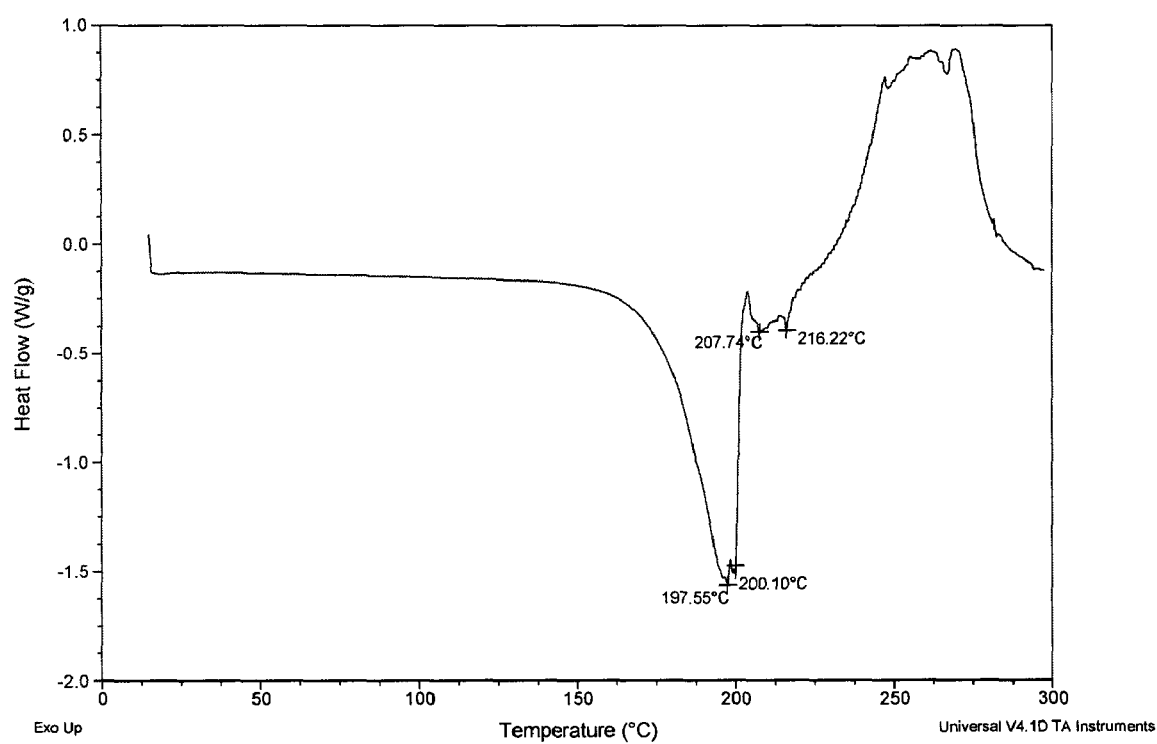
FIG. 26 depicts a DSC thermogram consistent with Form J.

In further embodiments, Form J is further characterized by a DSC thermogram comprising an endotherm at about 195 to about 205° C. In yet further embodiments, the solid form has a DSC thermogram substantially as shown in FIG. 26.

Figure 42:
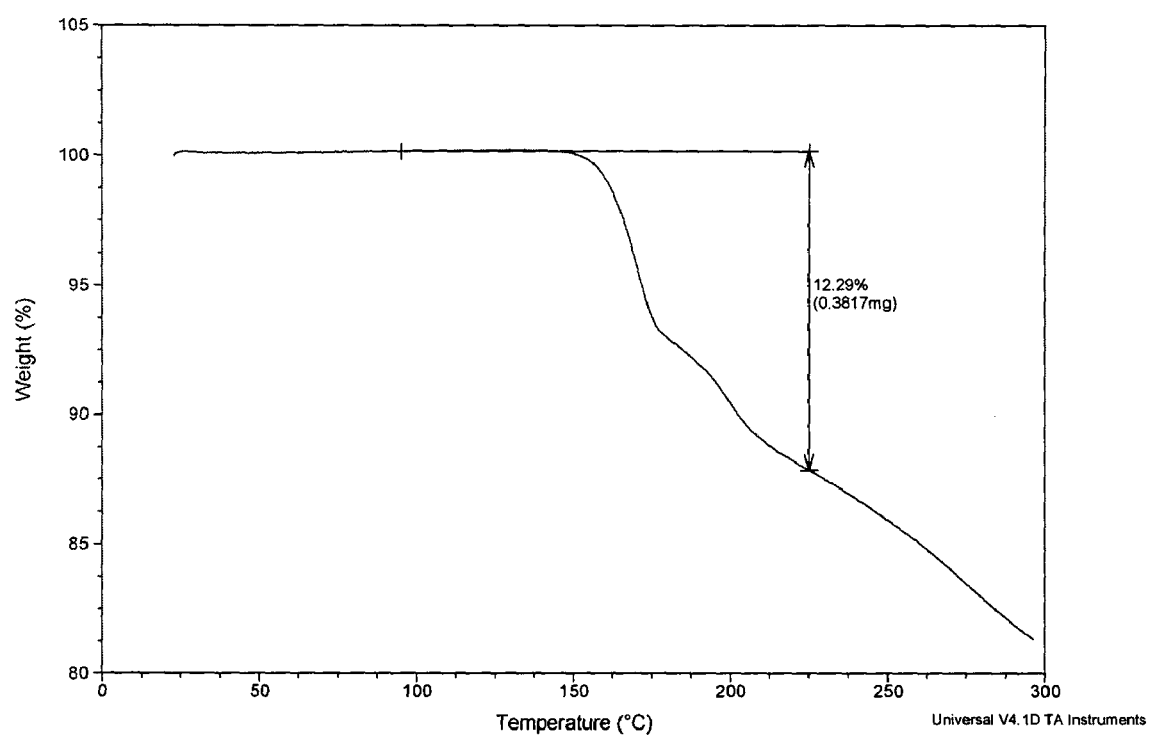
FIG. 42 depicts a TGA thermogram consistent with Form J.

Both TGA (FIG. 42) and DSC analysis suggest that Form J is a hydrate or solvate. In some embodiments, Form J is an N-methylpyrrolidinone solvate.

Form J can be prepared by precipitation of the solid form from a solution of 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine in N-methylpyrrolidinone or in dimethylacetamide.

Figure 11:
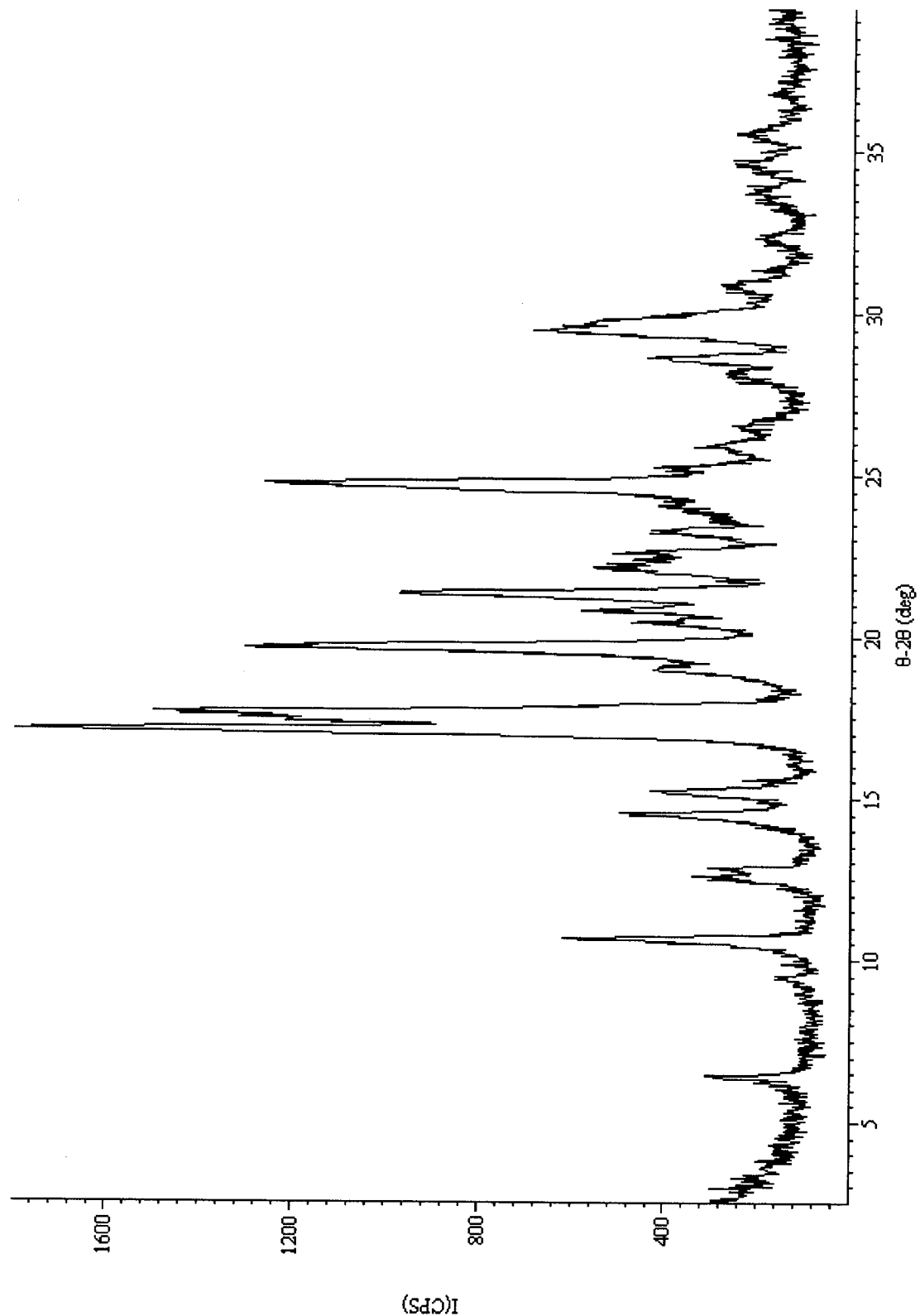
FIG. 11 depicts an XRPD spectrum consistent with Form K.

Form K is characterized as a crystalline form having an X-ray powder diffraction pattern comprising characteristic peaks, in terms of 2θ, at about 6.4°, about 10.6°, and about 19.7°, wherein the pattern further comprises at least one characteristic peak, in terms of 2θ, at about 12.7°, about 14.5°, about 15.2°, or about 17.4°. In some embodiments, the pattern further comprises at least one characteristic peak, in terms of 2θ, at about 21.3°, about 24.7°, about 28.6°, or about 29.6°. In further embodiments, the solid form exhibits a powder X-ray diffraction pattern substantially as shown in FIG. 11 (peaks are listed in Table K).

Figure 27:
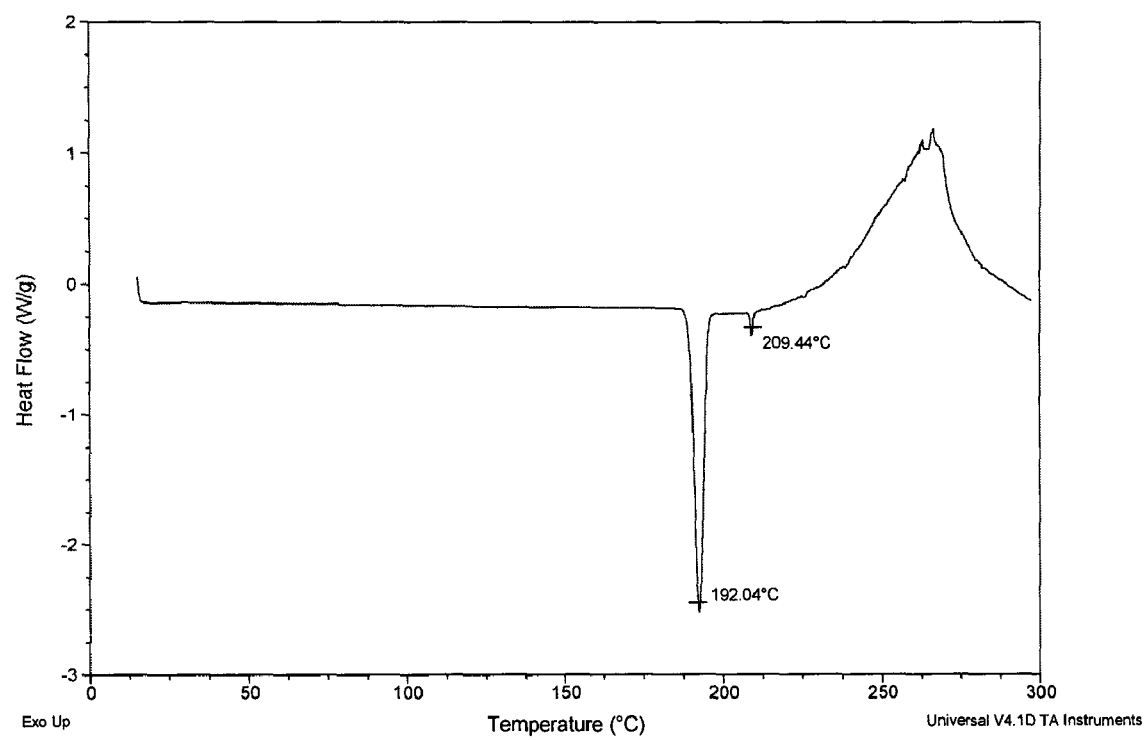
FIG. 27 depicts a DSC thermogram consistent with Form K.

In further embodiments, Form K is further characterized by a DSC thermogram comprising an endotherm at about 192° C. In yet further embodiments, Form K is characterized by a DSC thermogram substantially as shown in FIG. 27.

Figure 43:
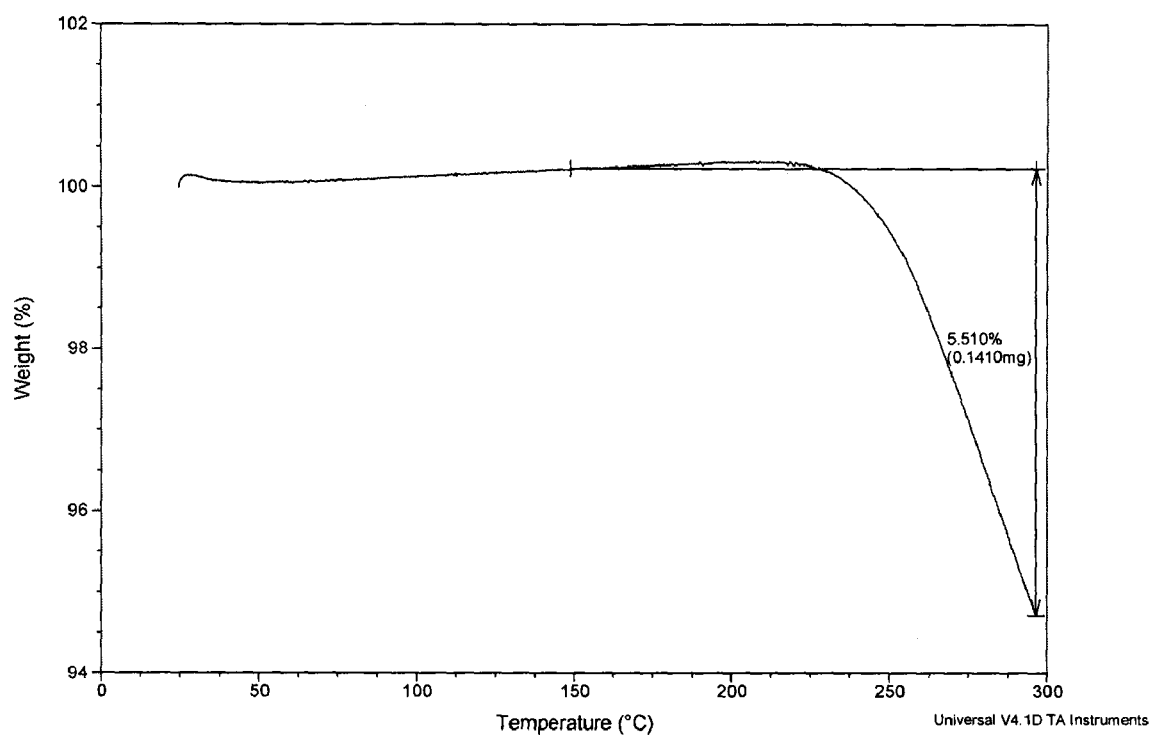
FIG. 43 depicts a TGA thermogram consistent with Form K.

TGA and DSC data suggest that Form K is an anhydrate or is unsolvated. See FIG. 43 for TGA data characterizing Form K.

Form K can be prepared by precipitating the solid form from a solution comprising 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine and methanol.

Figure 12:
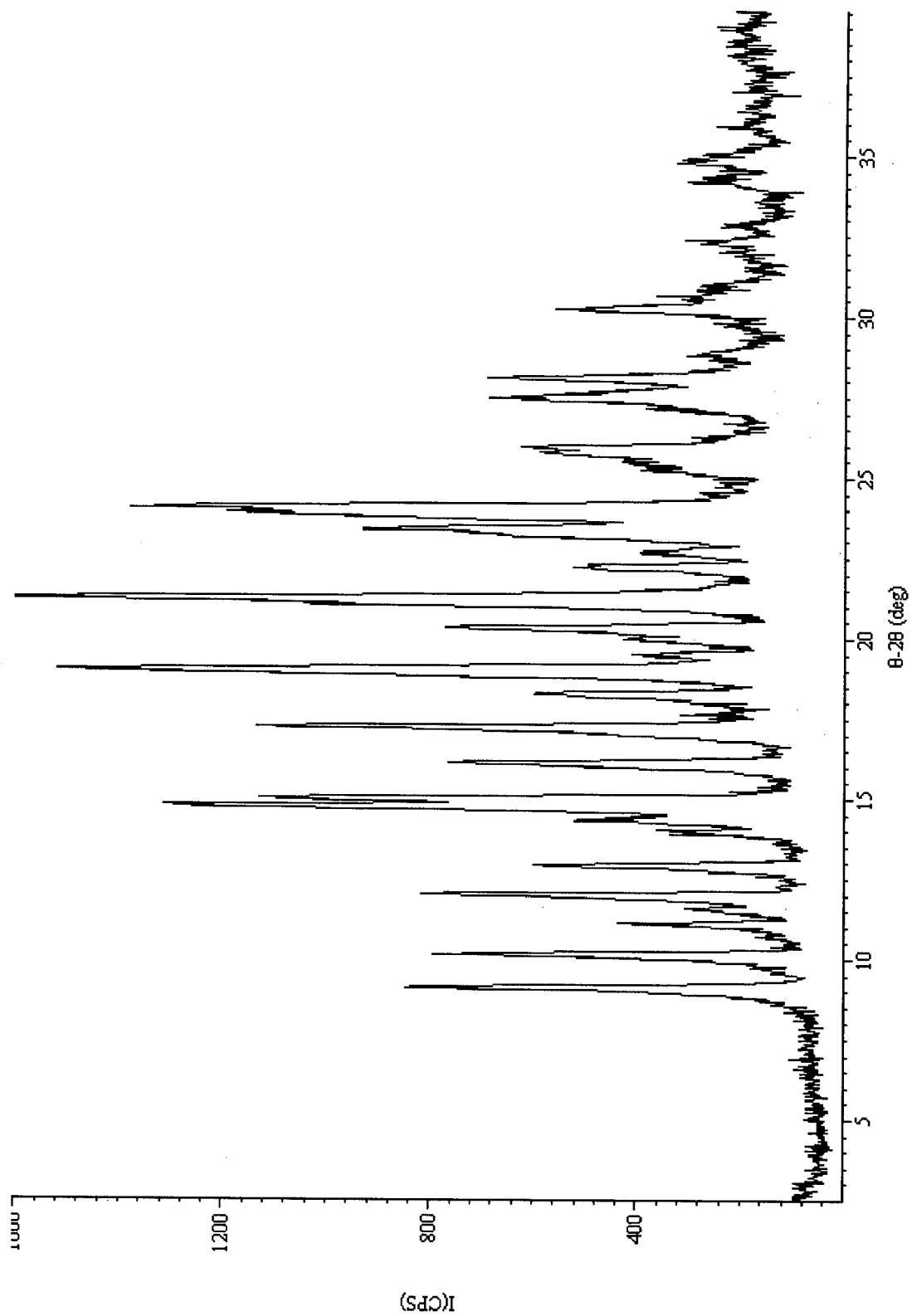
FIG. 12 depicts an XRPD spectrum consistent with Form L.

Form L is characterized as a crystalline form having an X-ray powder diffraction pattern comprising characteristic peaks, in terms of 2θ, at about 9.1°, about 10.1°, about 11.1°, and about 12.0°, wherein the pattern comprises no substantial peak at 2θ values below about 8.5°. In some embodiments, the pattern further comprises at least one characteristic peak, in terms of 2θ, at about 14.9°, about 16.1°, about 17.2°, about 18.3°, or about 19.0°. In some embodiments, the pattern further comprises at least one characteristic peak, in terms of 2θ, at about 20.3°, about 21.2°, about 22.2°, about 23.3°, about 24.0°, about 25.8°, about 27.5°, about 28.1°, or about 30.2°. In some embodiments, the solid form is characterized by an XRPD pattern substantially as shown in FIG. 12 (peaks are listed in Table L).

Figure 28:
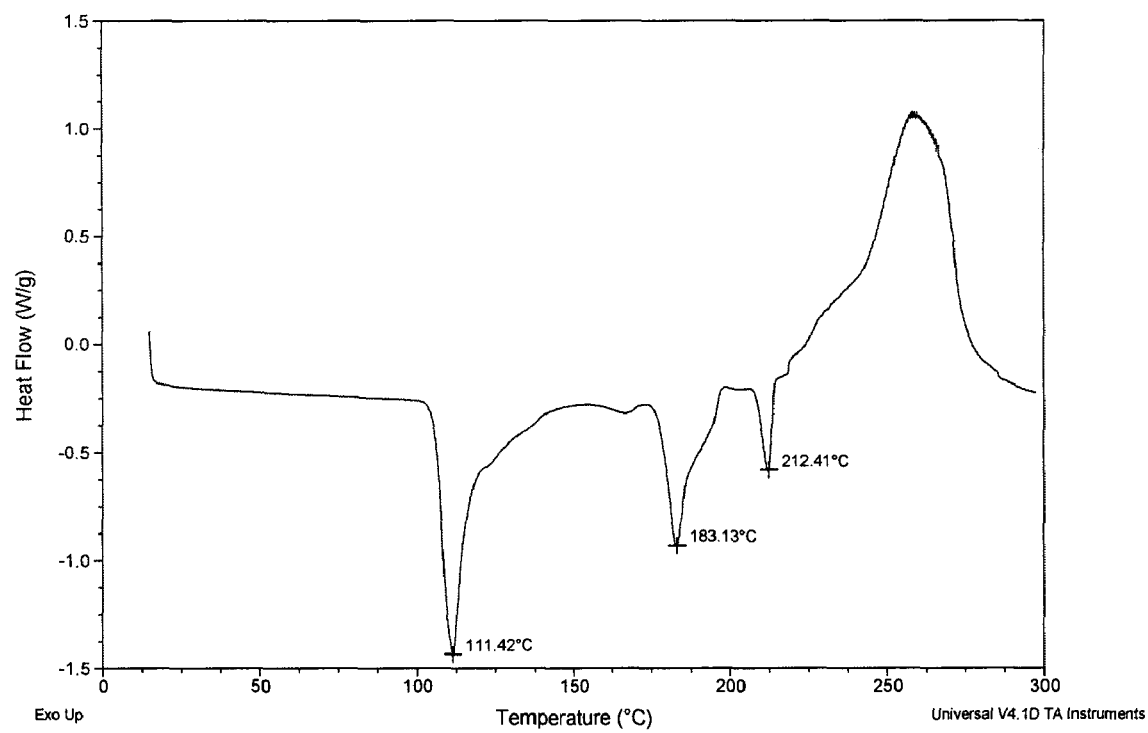
FIG. 28 depicts a DSC thermogram consistent with Form L.

Form L is further characterized by a DSC thermogram comprising an endotherm at about 212° C. In further embodiments, the solid form is characterized by a DSC thermogram substantially as shown in FIG. 28.

Figure 44:
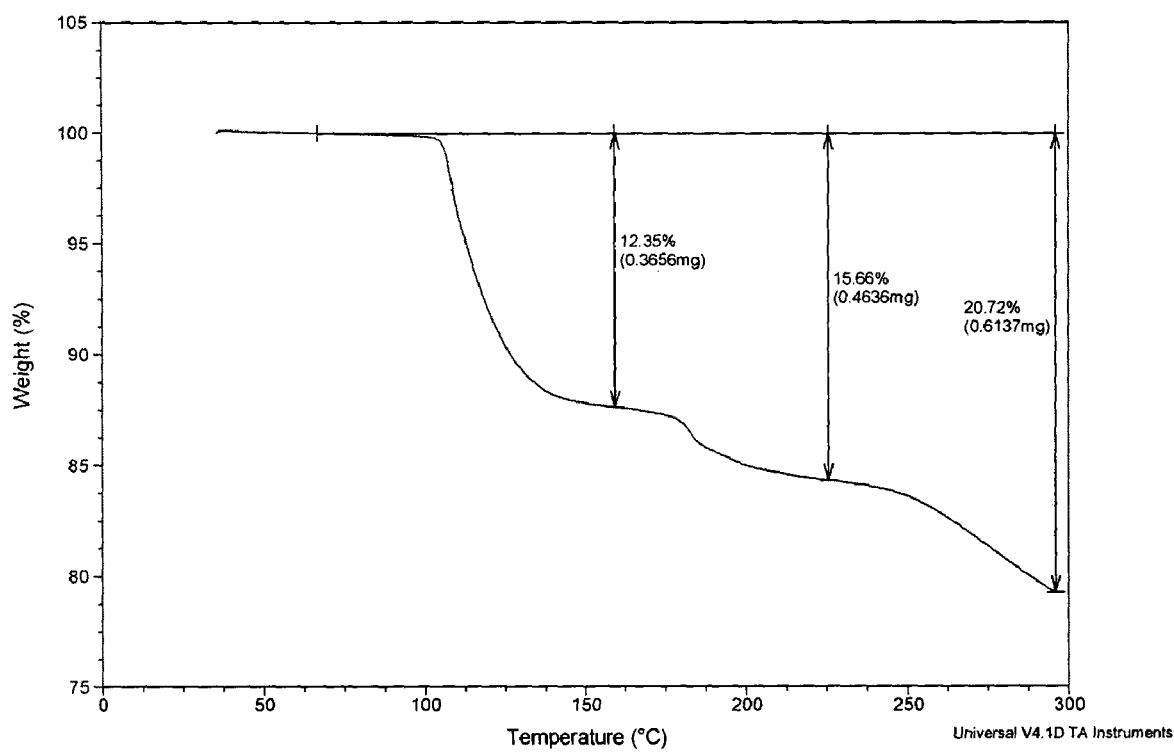
FIG. 44 depicts a TGA thermogram consistent with Form L.

Both TGA (FIG. 44) and DSC analysis suggest that Form L is hydrated or is solvated.

Form L can be prepared by precipitating the solid form from a solution comprising 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine, a trialkylamine, and tetrahydrofuran.

Figure 13:
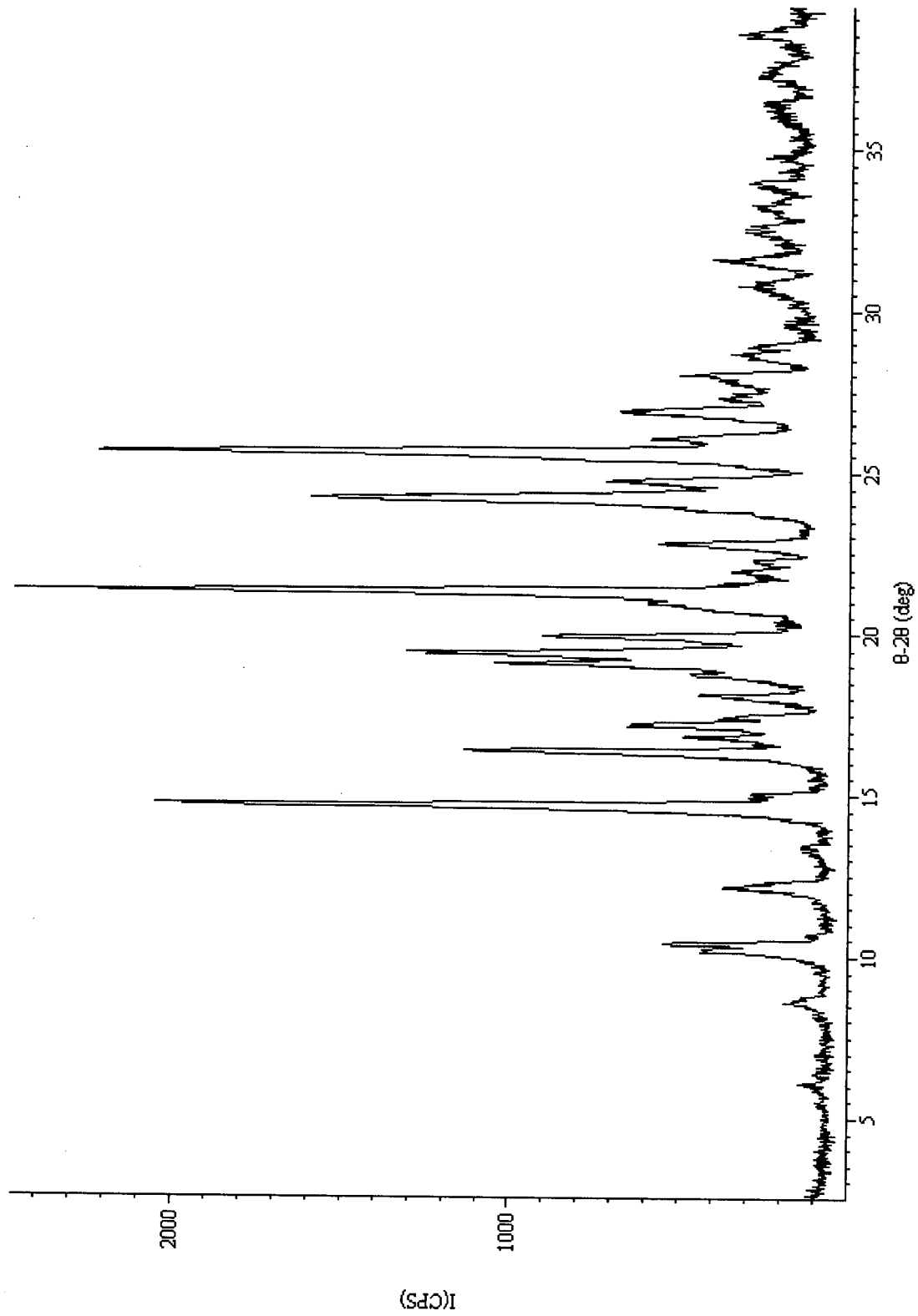
FIG. 13 depicts an XRPD spectrum consistent with Form M.

Form M is characterized as a crystalline form having an X-ray powder diffraction pattern comprising characteristic peaks, in terms of 2θ, at about 10.4°, about 14.7°, and about 16.4°. In some embodiments, the pattern further comprises at least one characteristic peak, in terms of 2θ, at about 12.2°, about 17.2°, about 19.1°, or about 19.4°. In some embodiments, the pattern further comprises at least one characteristic peak, in terms of 2θ, at about 19.9°, about 21.3°, about 22.8°, about 24.2°, about 24.7°, about 25.6°, or about 26.9°. In some embodiments, the solid form has a powder X-ray diffraction pattern substantially as shown in FIG. 13 (peaks are listed in Table M).

Figure 29:
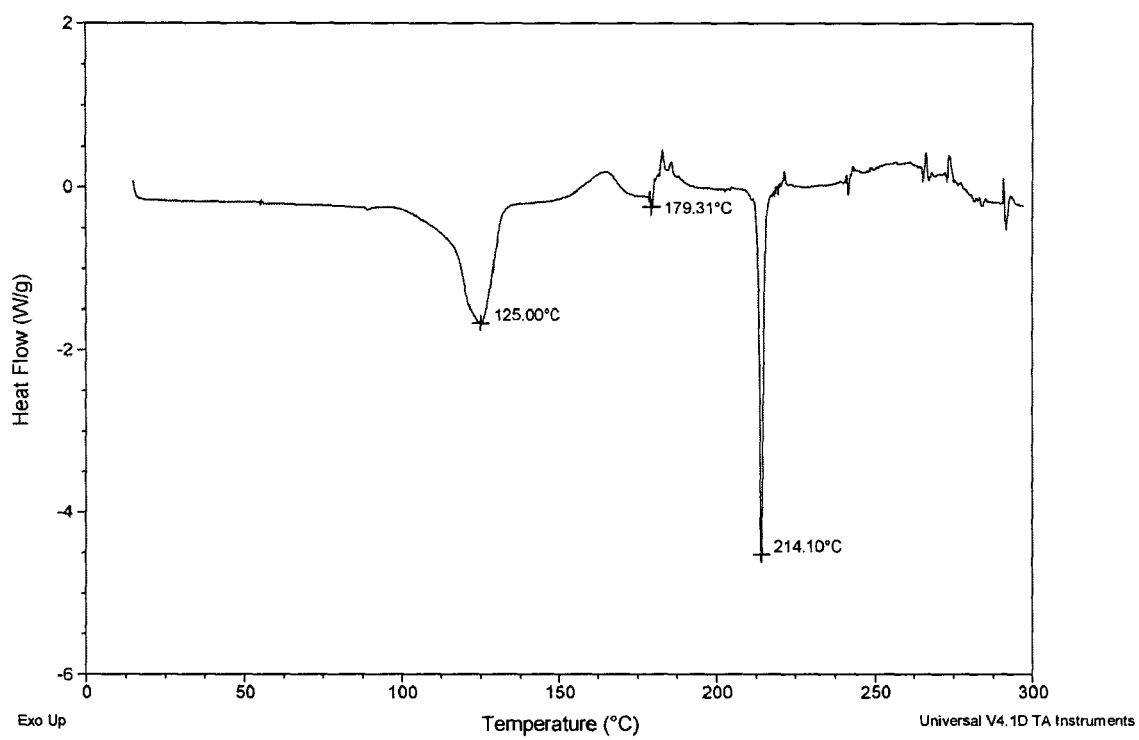
FIG. 29 depicts a DSC thermogram consistent with Form M.

In further embodiments, Form M is further characterized by a DSC thermogram comprising an endotherm at about 214° C. In yet further embodiments, the solid form has a DSC thermogram substantially as shown in FIG. 29.

Figure 45:
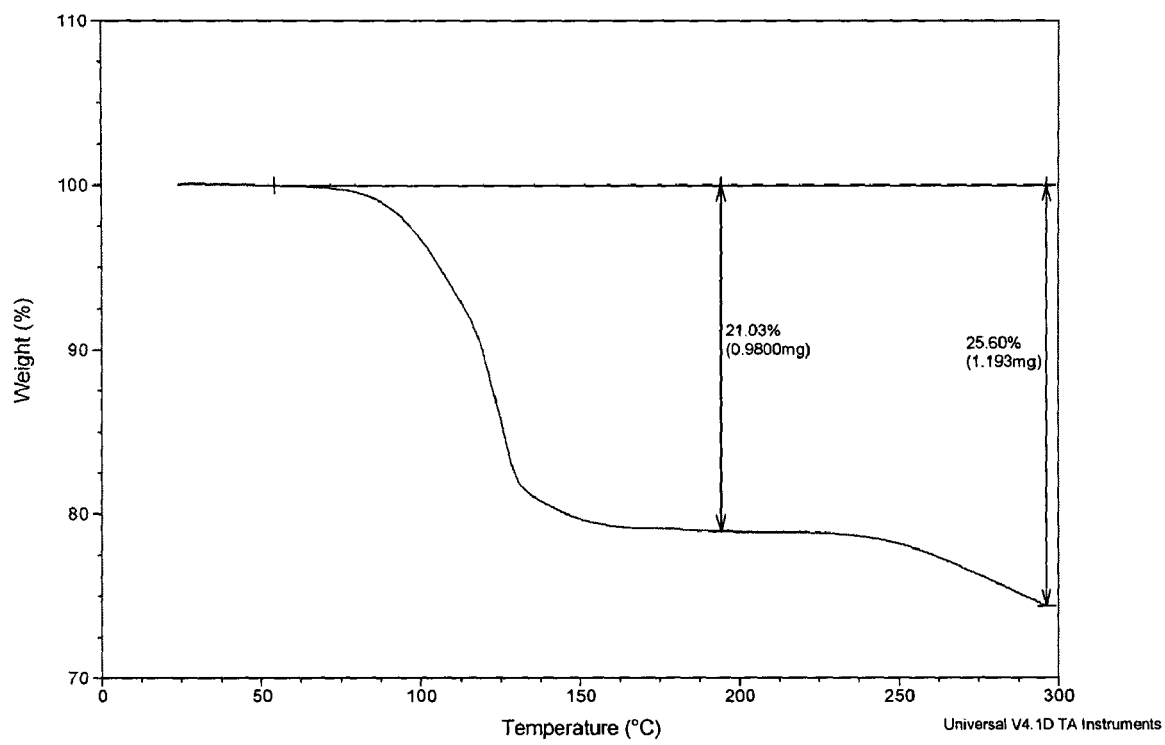
FIG. 45 depicts a TGA thermogram consistent with Form M.

Thermal analysis by TGA (FIG. 45) and DSC suggest the solid form is hydrated or solvated.

Form M can be prepared by precipitating the solid form from a solution comprising 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine, a trialkylamine, and ethyl acetate or other organic ester.

Figure 14:
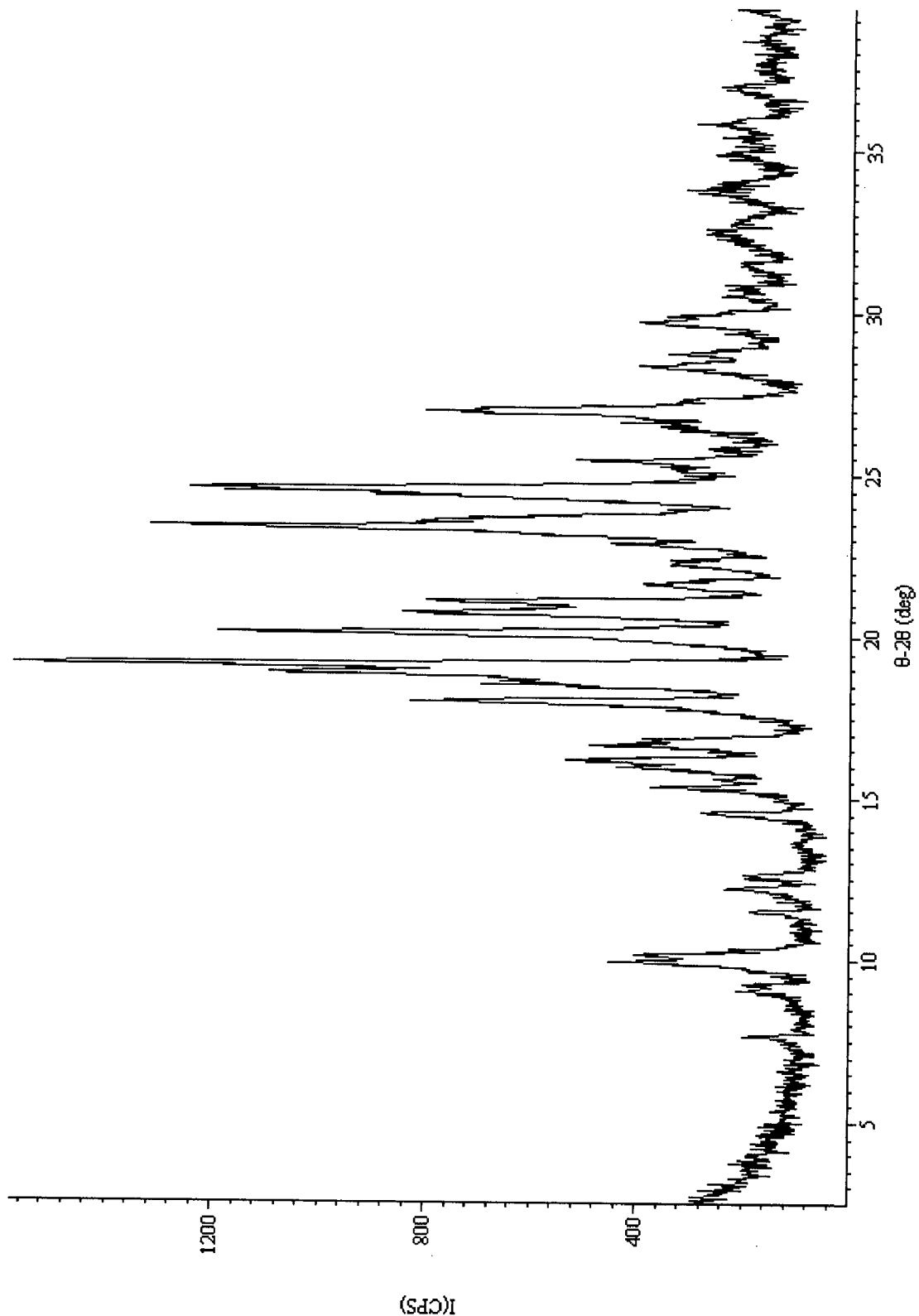
FIG. 14 depicts an XRPD spectrum consistent with Form N.

Form N of 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine having an X-ray powder diffraction pattern comprising characteristic peaks, in terms of 2θ, at about 10.0°, about 15.3°, about 16.1°, and about 20.1°, wherein the pattern comprises no substantial peak at 2θ values below about 7.0°, wherein the pattern further comprises at least one characteristic peak, in terms of 2θ, at about 14.5°, about 16.7°, about 18.0°, about 18.9°, about 19.1°, or about 20.7°. In some embodiments, the pattern further comprises at least one characteristic peak, in terms of 2θ, at about 21.1°, about 23.4°, about 24.5°, about 25.4°, about 27.0°, about 28.3°, or about 29.8°. In some embodiments, Form N has a powder X-ray diffraction pattern substantially as shown in FIG. 14 (peaks are listed in Table N).

Figure 30:
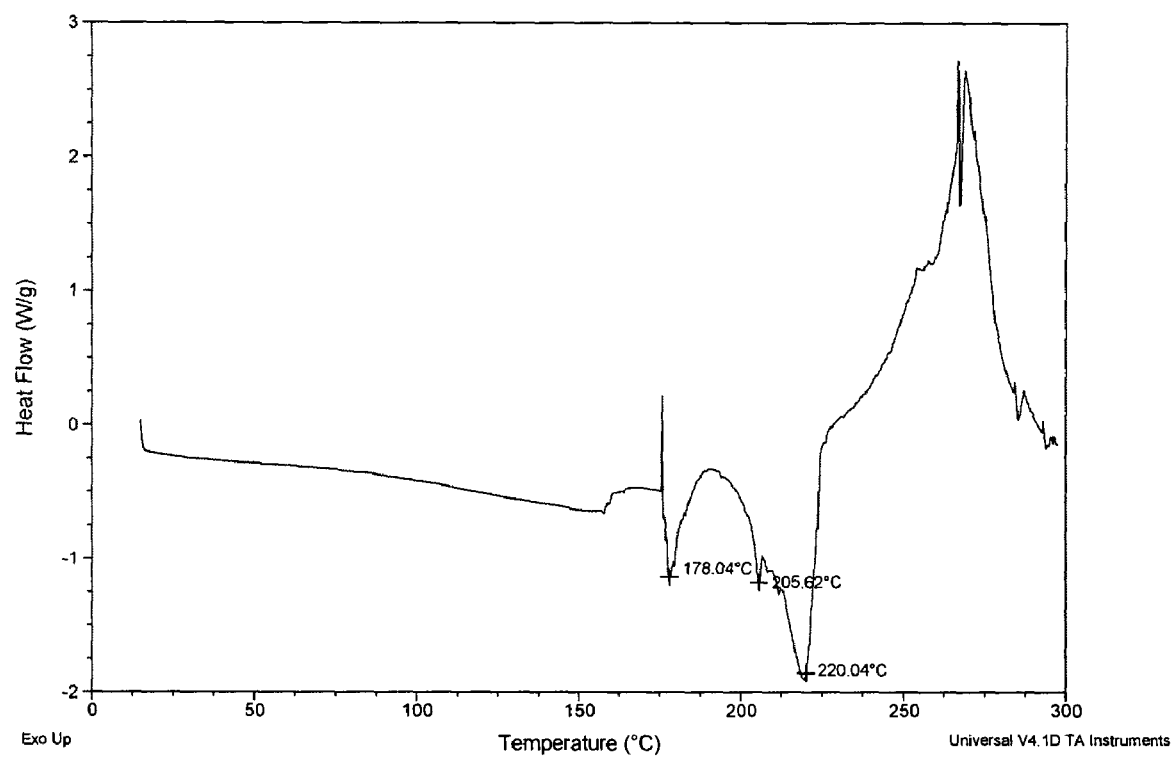
FIG. 30 depicts a DSC thermogram consistent with Form N.

In further embodiments, Form N is characterized by a DSC thermogram comprising an endotherm at about 220° C. In yet further embodiments, Form N has a DSC thermogram substantially as shown in FIG. 30.

Figure 46:
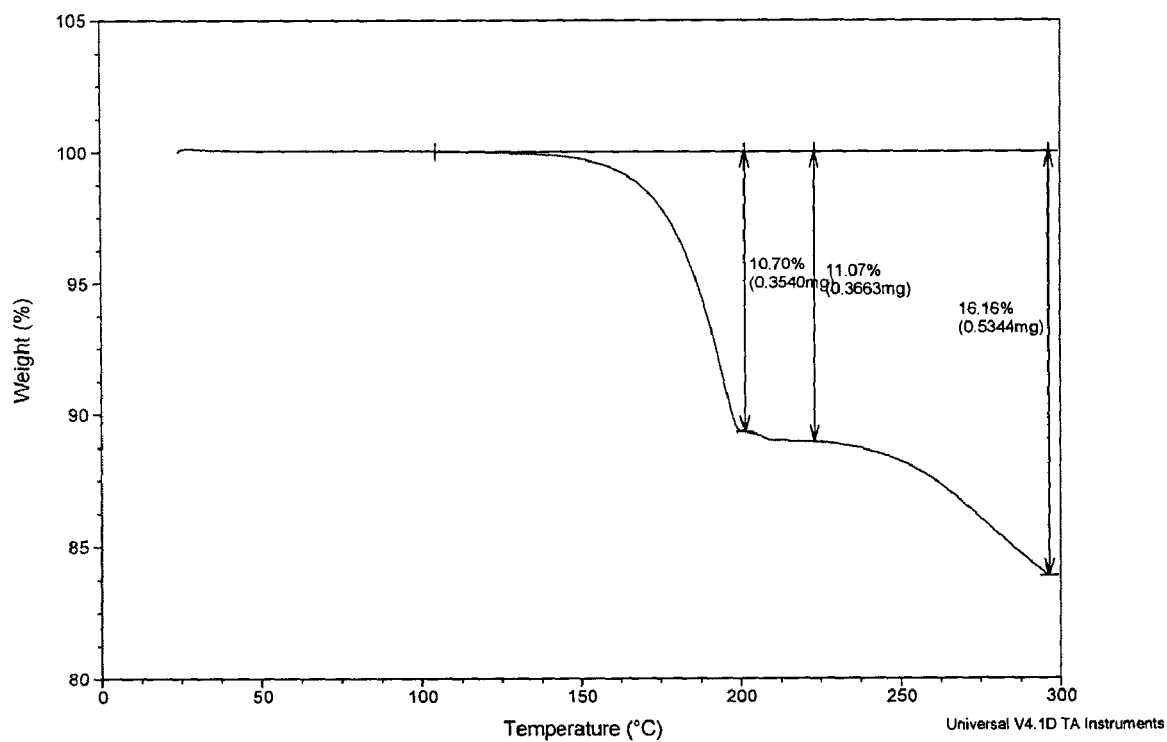
FIG. 46 depicts a TGA thermogram consistent with Form N.

Form N is suggested as a hydrate or solvate by TGA and DSC analysis. See FIG. 46 for TGA data characterizing the solid form.

Form N can be prepared by suspending 1-methyl-5-(2-(5-(trifluoromethyl)-1H-imidazol-2-yl)pyridin-4-yloxy)-N-(4-

(trifluoromethyl)phenyl)-1H-benzo[d]imidazol-2-amine in a glycol such as propylene glycol.

Figure 15:
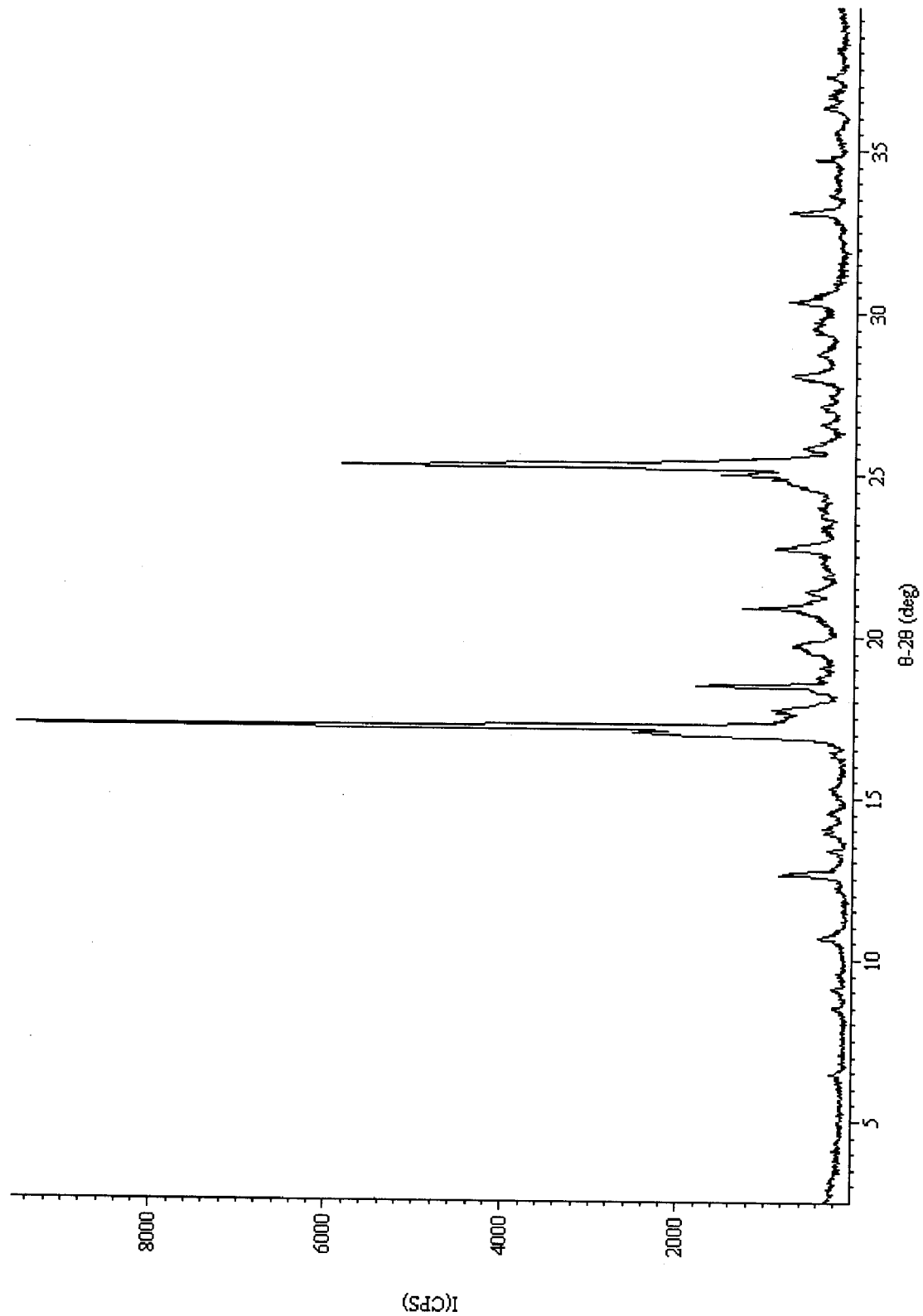
FIG. 15 depicts an XRPD spectrum consistent with Form O.

Form O is characterized as a crystalline form having an X-ray powder diffraction pattern comprising characteristic peaks, in terms of 2θ, at about 12.6°, about 17.2°, about 25.3°, and about 33.1°, wherein the pattern comprises no substantial peak at 2θ values of about 23.0° to about 24.5°. In some embodiments, the pattern further comprises at least one characteristic peak, in terms of 2θ, at about 18.5°, about 20.9°, about 22.8°, about 28.0°, or about 30.3°. In some embodiments, Form O has an XRPD pattern substantially as shown in FIG. 15 (peaks are listed in Table O).

Figure 31:
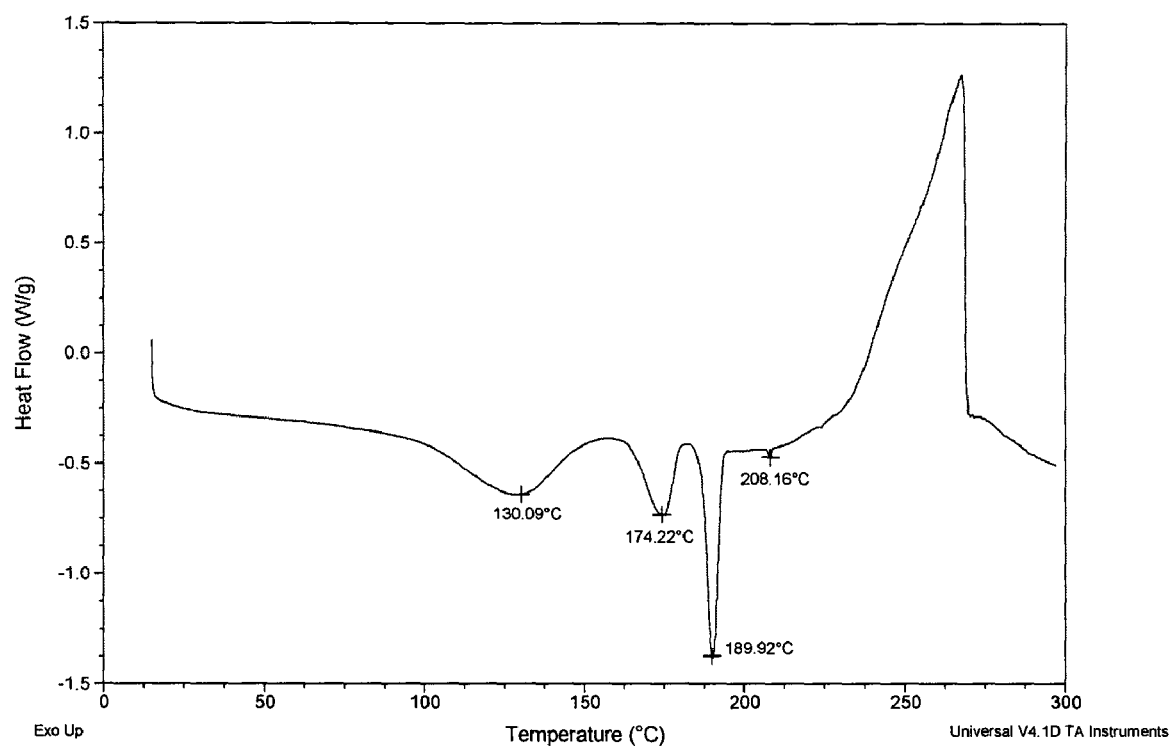
FIG. 31 depicts a DSC thermogram consistent with Form O.

In further embodiments, the solid form is characterized by a DSC thermogram comprising an endotherm at about 190° C. In yet further embodiments, Form O is characterized by a DSC thermogram substantially as shown in FIG. 31.

Figure 47:
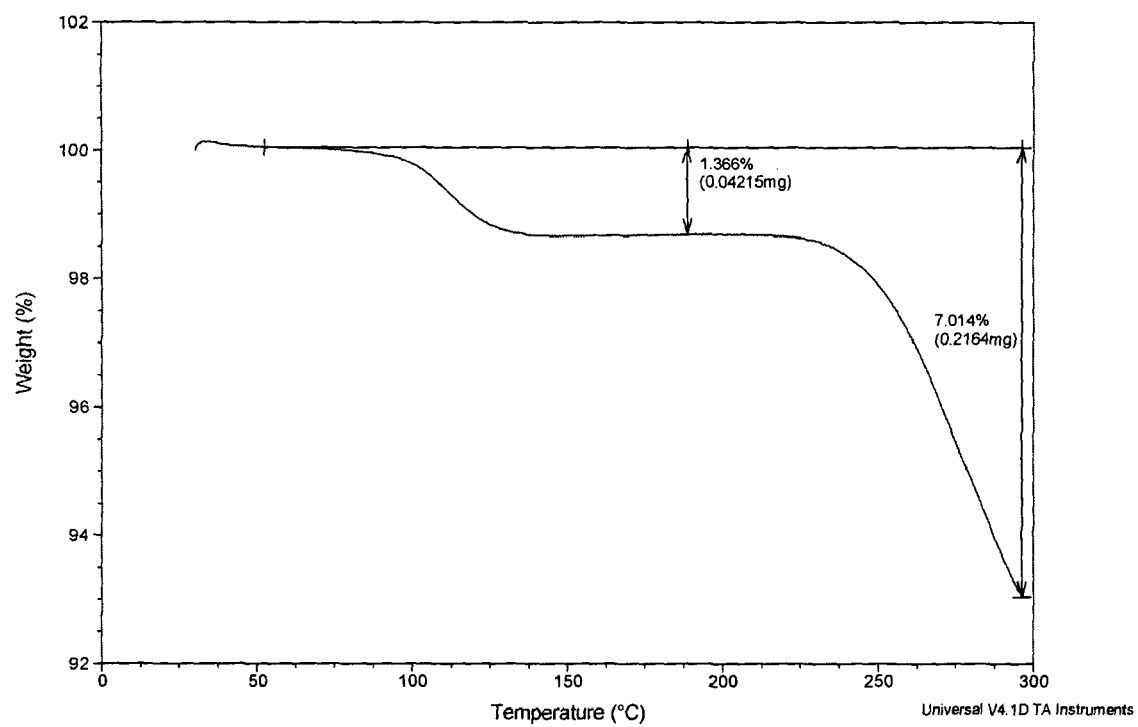
FIG. 47 depicts a TGA thermogram consistent with Form O.

TGA and DSC analysis suggest that Form O is a hydrate or solvate. See FIG. 47 for TGA data characterizing the solid form.

Form O can be prepared by precipitating the solid form from a solution comprising 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine and methanol.

Figure 16:
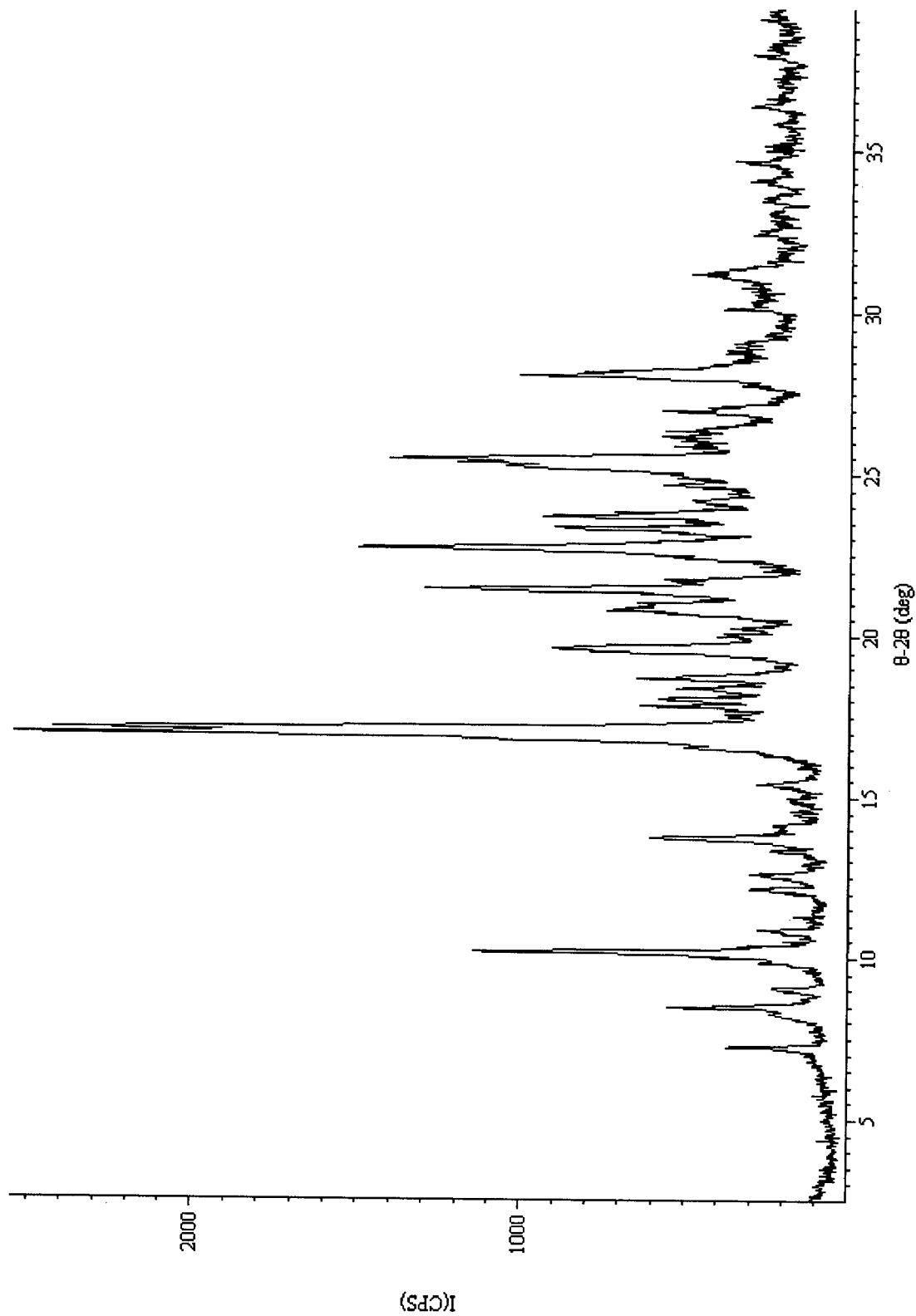
FIG. 16 depicts an XRPD spectrum consistent with Form P.

Form P is characterized as a crystalline form having an X-ray powder diffraction pattern comprising characteristic peaks, in terms of 2θ, at about 7.2° and about 10.2°. In some embodiments, the pattern further comprises at least one characteristic peak, in terms of 2θ, at about 8.4°, about 13.7°, about 17.0°, or about 19.6°. In some embodiments, the pattern further comprises at least one characteristic peak, in terms of 2θ, at about 21.4°, about 22.7°, about 23.3°, about 23.7°, about 25.4°, about 28.1°, or about 31.2°. In some embodiments, Form P has an XRPD pattern substantially as shown in FIG. 16 (peaks are listed in Table P).

Figure 32:
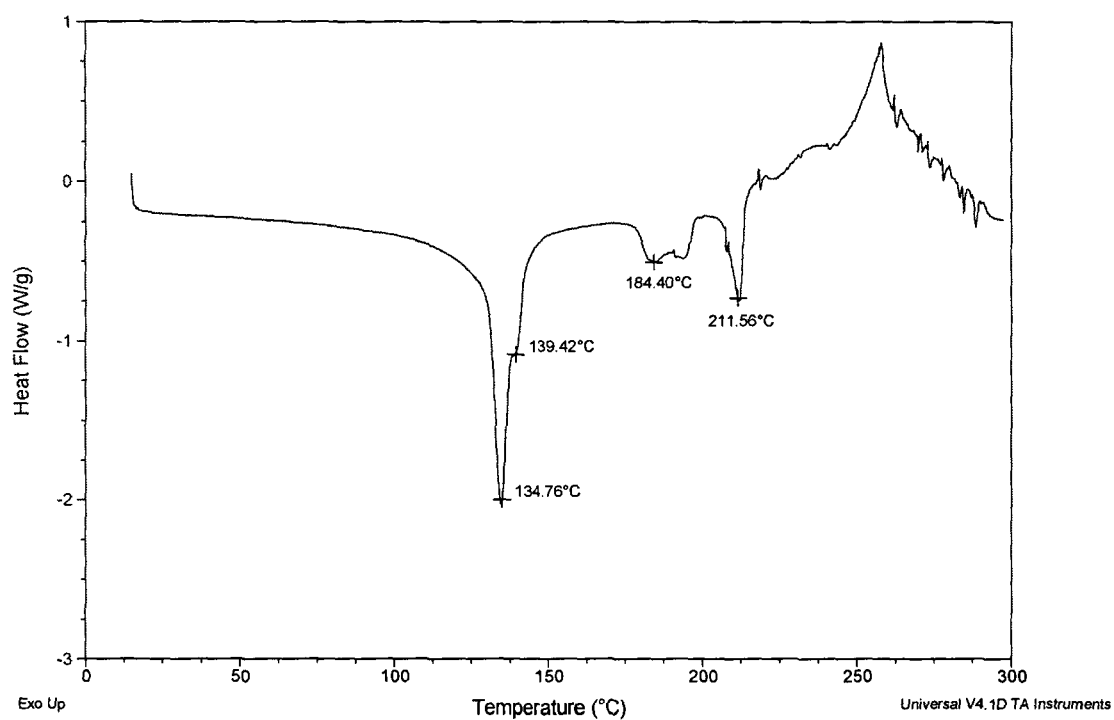
FIG. 32 depicts a DSC thermogram consistent with Form P.

In further embodiments, Form P is characterized by a DSC thermogram comprising an endotherm at about 212° C. In yet further embodiments, Form P exhibits a DSC thermogram substantially as shown in FIG. 32.

Figure 48:
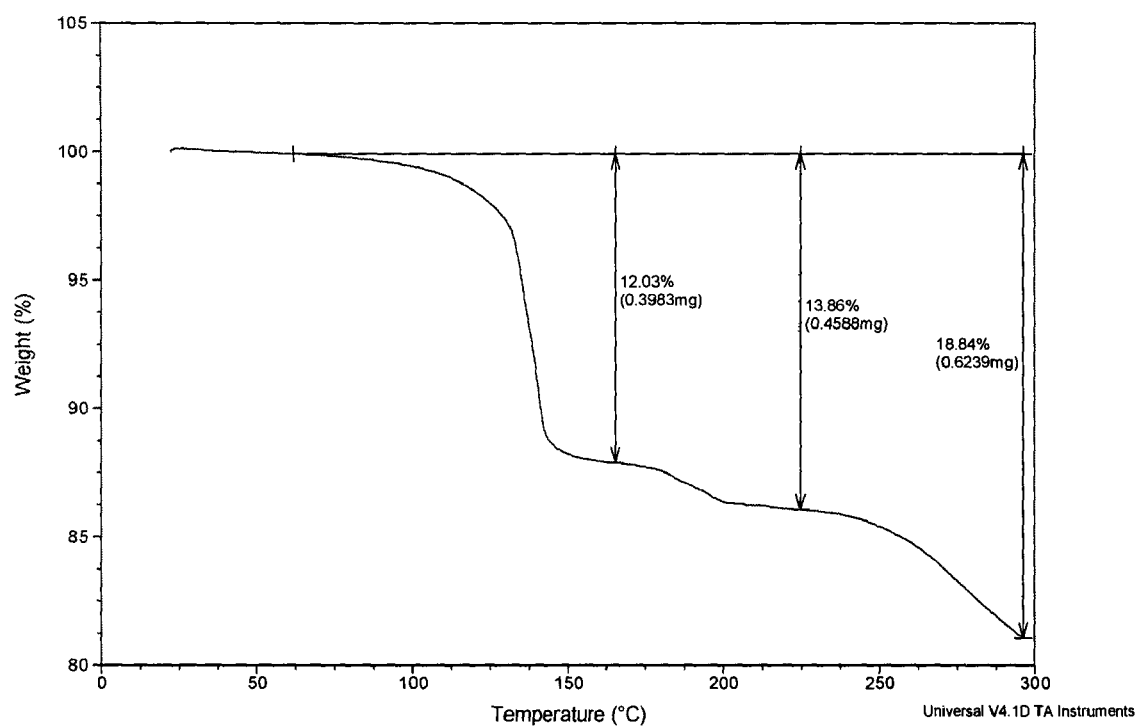
FIG. 48 depicts a TGA thermogram consistent with Form P.

Thermal analysis by TGA and DSC suggest that Form P is a hydrate or solvate. See FIG. 48 for TGA data characterizing Form P.

Form P can be prepared by precipitation of the solid from a solution comprising 1-methyl-5-(2-(5-trifluoromethyl)-1H-imidazol-2-yl)pyridin-4-yloxy)-N-(4-(trifluoromethyl)phenyl)-1H-benzo[d]imidazol-2-amine, trialkylamine, and an ether such as tetrahydrofuran.

Major peaks of respective XRPD patterns of the 16 solid forms of the invention are listed in Tables A-P as follows.

TABLE A (Form A)

| Peak No. | 2Theta (deg) | Intensity (Counts) |
|---|---|---|
| 1 | 9.0 | 130 |
| 2 | 10.8 | 55 |
| 3 | 12.1 | 98 |
| 4 | 12.6 | 56 |
| 5 | 13.3 | 53 |
| 6 | 13.8 | 28 |
| 7 | 14.1 | 86 |
| 8 | 16.7 | 46 |
| 9 | 17.1 | 883 |
| 10 | 17.4 | 32 |
| 11 | 18.4 | 326 |
| 12 | 18.7 | 264 |
| 13 | 19.5 | 135 |
| 14 | 20.4 | 36 |
| 15 | 20.8 | 318 |
| 16 | 21.0 | 334 |
| 17 | 21.7 | 69 |
| 18 | 22.7 | 280 |
| 19 | 23.6 | 69 |
| 20 | 24.4 | 97 |
| 21 | 25.0 | 269 |
| 22 | 25.3 | 351 |
| 23 | 25.9 | 74 |
| 24 | 26.5 | 108 |
| 25 | 27.0 | 198 |
| 26 | 28.0 | 254 |
| 27 | 28.5 | 44 |
| 28 | 28.8 | 102 |
| 29 | 30.4 | 130 |
| 30 | 30.5 | 75 |
| 31 | 31.2 | 26 |
| 32 | 32.8 | 39 |
| 33 | 33.0 | 78 |
| 34 | 34.1 | 39 |
| 35 | 36.4 | 51 |
| 36 | 39.1 | 34 |
| 37 | 39.6 | 26 |

TABLE B (Form B)

| Peak No. | 2Theta (deg) | Intensity (Counts) |
|---|---|---|
| 1 | 8.7 | 24 |
| 2 | 9.5 | 13 |
| 3 | 12.2 | 130 |
| 4 | 13.6 | 32 |
| 5 | 15.1 | 19 |
| 6 | 16.3 | 43 |
| 7 | 18.0 | 261 |
| 8 | 19.2 | 77 |
| 9 | 20.6 | 119 |
| 10 | 21.8 | 135 |
| 11 | 23.3 | 85 |
| 12 | 24.5 | 185 |
| 13 | 26.0 | 86 |
| 14 | 27.0 | 20 |
| 15 | 28.2 | 89 |
| 16 | 29.1 | 12 |
| 17 | 30.2 | 42 |
| 18 | 32.8 | 14 |
| 19 | 35.0 | 24 |
| 20 | 36.3 | 8 |
| 21 | 37.0 | 8 |

TABLE C (Form C)

| Peak No. | 2Theta (deg) | Intensity (Counts) |
|---|---|---|
| 1 | 6.2 | 11 |
| 2 | 6.7 | 59 |
| 3 | 7.6 | 63 |
| 4 | 9.2 | 107 |
| 5 | 9.6 | 188 |
| 6 | 11.9 | 49 |
| 7 | 12.8 | 22 |
| 8 | 14.6 | 48 |
| 9 | 15.3 | 181 |
| 10 | 15.8 | 14 |
| 11 | 17.6 | 235 |

TABLE C-continued (Form C)

| Peak No. | 2Theta (deg) | Intensity (Counts) |
|---|---|---|
| 12 | 18.0 | 112 |
| 13 | 18.8 | 231 |
| 14 | 19.4 | 109 |
| 15 | 20.2 | 111 |
| 16 | 20.8 | 113 |
| 17 | 21.7 | 55 |
| 18 | 22.8 | 28 |
| 19 | 23.5 | 210 |
| 20 | 24.0 | 169 |
| 21 | 24.9 | 104 |
| 22 | 26.1 | 86 |
| 23 | 27.5 | 67 |
| 24 | 27.9 | 29 |
| 25 | 28.4 | 15 |
| 26 | 29.1 | 37 |
| 27 | 29.5 | 13 |
| 28 | 30.5 | 45 |
| 29 | 31.1 | 15 |
| 30 | 32.5 | 38 |
| 31 | 33.3 | 17 |
| 32 | 34.5 | 7 |
| 33 | 35.9 | 12 |
| 34 | 36.7 | 10 |
| 35 | 37.1 | 7 |
| 36 | 38.2 | 8 |
| 37 | 38.6 | 7 |
| 38 | 39.2 | 10 |

TABLE D (Form D)

| Peak No. | 2Theta (deg) | Intensity (Counts) |
|---|---|---|
| 1 | 6.1 | 99 |
| 2 | 6.5 | 559 |
| 3 | 7.2 | 28 |
| 4 | 7.5 | 369 |
| 6 | 7.8 | 179 |
| 7 | 8.1 | 217 |
| 8 | 8.5 | 58 |
| 9 | 8.7 | 148 |
| 10 | 9.0 | 953 |
| 11 | 9.3 | 2900 |
| 12 | 9.6 | 209 |
| 13 | 11.3 | 306 |
| 14 | 11.6 | 1891 |
| 15 | 12.8 | 301 |
| 16 | 13.1 | 276 |
| 17 | 13.7 | 111 |
| 18 | 14.1 | 128 |
| 19 | 14.4 | 916 |
| 20 | 14.8 | 4159 |
| 22 | 15.5 | 908 |
| 23 | 15.9 | 93 |
| 24 | 16.3 | 76 |
| 25 | 16.9 | 123 |
| 26 | 17.2 | 2127 |
| 27 | 17.4 | 2976 |
| 28 | 18.0 | 1195 |
| 29 | 18.4 | 1102 |
| 30 | 18.8 | 4582 |
| 32 | 19.6 | 5691 |
| 34 | 20.3 | 3108 |
| 35 | 20.6 | 2268 |
| 36 | 21.1 | 322 |
| 37 | 21.5 | 396 |
| 38 | 21.7 | 198 |
| 39 | 22.3 | 635 |
| 40 | 22.9 | 436 |
| 41 | 23.3 | 859 |
| 42 | 23.5 | 4456 |
| 46 | 24.4 | 2028 |

TABLE D-continued (Form D)

| Peak No. | 2Theta (deg) | Intensity (Counts) |
|---|---|---|
| 47 | 24.8 | 621 |
| 48 | 25.0 | 1910 |
| 49 | 25.4 | 3628 |
| 50 | 26.0 | 3049 |
| 51 | 26.3 | 1302 |
| 52 | 26.6 | 527 |
| 53 | 27.4 | 1172 |
| 54 | 27.7 | 1657 |
| 56 | 28.1 | 1028 |
| 57 | 28.3 | 145 |
| 58 | 28.8 | 512 |
| 59 | 29.3 | 188 |
| 60 | 29.7 | 397 |
| 61 | 30.1 | 405 |
| 62 | 30.6 | 449 |
| 63 | 31.0 | 93 |
| 64 | 31.3 | 628 |
| 65 | 31.6 | 46 |
| 66 | 32.4 | 127 |
| 67 | 32.6 | 43 |
| 68 | 32.9 | 319 |
| 69 | 33.1 | 170 |
| 70 | 33.3 | 56 |
| 71 | 33.5 | 143 |
| 72 | 34.3 | 163 |
| 73 | 34.6 | 135 |
| 74 | 34.7 | 73 |
| 75 | 35.5 | 108 |
| 76 | 35.7 | 182 |
| 77 | 35.8 | 59 |
| 78 | 36.7 | 225 |
| 79 | 36.9 | 201 |
| 80 | 37.0 | 206 |
| 81 | 37.2 | 110 |
| 82 | 37.4 | 153 |
| 83 | 37.7 | 69 |
| 84 | 37.8 | 69 |
| 85 | 38.0 | 74 |
| 86 | 38.3 | 81 |
| 87 | 38.5 | 55 |
| 88 | 38.7 | 86 |
| 89 | 38.9 | 73 |
| 90 | 39.9 | 248 |

TABLE E (Form E)

| Peak No. | 2Theta (deg) | Intensity (Counts) |
|---|---|---|
| 3 | 6.8 | 40 |
| 4 | 7.5 | 71 |
| 5 | 8.0 | 13 |
| 6 | 9.0 | 23 |
| 7 | 9.4 | 27 |
| 8 | 9.8 | 74 |
| 9 | 10.6 | 63 |
| 10 | 11.1 | 25 |
| 11 | 11.6 | 17 |
| 12 | 12.3 | 12 |
| 13 | 12.8 | 21 |
| 14 | 13.8 | 26 |
| 15 | 14.7 | 34 |
| 16 | 15.1 | 40 |
| 17 | 15.6 | 71 |
| 18 | 16.0 | 188 |
| 19 | 17.4 | 114 |
| 20 | 17.9 | 62 |
| 21 | 18.6 | 157 |
| 22 | 19.3 | 82 |
| 23 | 19.8 | 53 |
| 24 | 20.3 | 63 |
| 25 | 20.7 | 40 |

TABLE E-continued (Form E)

| Peak No. | 2Theta (deg) | Intensity (Counts) |
|---|---|---|
| 26 | 21.3 | 39 |
| 27 | 21.7 | 30 |
| 28 | 22.5 | 92 |
| 29 | 23.5 | 148 |
| 30 | 24.3 | 74 |
| 31 | 24.8 | 80 |
| 32 | 25.8 | 69 |
| 33 | 26.2 | 36 |
| 34 | 27.0 | 29 |
| 35 | 27.3 | 37 |
| 36 | 28.0 | 14 |
| 37 | 28.5 | 17 |
| 38 | 29.1 | 20 |
| 39 | 29.6 | 9 |
| 40 | 30.3 | 21 |
| 41 | 31.1 | 17 |
| 42 | 31.7 | 14 |
| 43 | 32.0 | 25 |
| 44 | 32.4 | 14 |
| 45 | 33.0 | 9 |
| 46 | 33.4 | 15 |
| 47 | 34.8 | 7 |
| 48 | 35.6 | 6 |
| 49 | 36.2 | 6 |
| 50 | 36.6 | 9 |
| 51 | 37.0 | 7 |
| 52 | 37.7 | 9 |
| 53 | 38.7 | 7 |
| 54 | 39.0 | 8 |
| 55 | 39.6 | 9 |

TABLE F (Form F)

| Peak No. | 2Theta (deg) | Intensity (Counts) |
|---|---|---|
| 1 | 5.8 | 44 |
| 2 | 7.9 | 12 |
| 3 | 8.1 | 21 |
| 4 | 8.5 | 23 |
| 5 | 9.1 | 15 |
| 6 | 9.6 | 22 |
| 7 | 10.1 | 14 |
| 8 | 10.8 | 26 |
| 9 | 11.9 | 30 |
| 10 | 12.9 | 34 |
| 11 | 13.9 | 26 |
| 12 | 14.5 | 20 |
| 13 | 14.7 | 24 |
| 14 | 15.5 | 37 |
| 15 | 15.8 | 86 |
| 16 | 16.2 | 37 |
| 17 | 16.8 | 116 |
| 18 | 17.1 | 79 |
| 19 | 17.5 | 89 |
| 20 | 17.9 | 56 |
| 21 | 18.2 | 106 |
| 22 | 18.8 | 240 |
| 23 | 19.3 | 46 |
| 24 | 19.6 | 364 |
| 25 | 19.9 | 52 |
| 26 | 20.3 | 72 |
| 27 | 20.9 | 12 |
| 28 | 21.4 | 68 |
| 29 | 21.7 | 105 |
| 30 | 22.2 | 38 |
| 31 | 22.7 | 89 |
| 32 | 23.0 | 107 |
| 33 | 23.9 | 78 |
| 34 | 24.3 | 91 |
| 35 | 24.7 | 20 |
| 36 | 25.0 | 60 |

TABLE F-continued (Form F)

| Peak No. | 2Theta (deg) | Intensity (Counts) |
|---|---|---|
| 37 | 25.7 | 219 |
| 38 | 26.3 | 31 |
| 39 | 27.0 | 26 |
| 40 | 27.1 | 42 |
| 41 | 27.3 | 54 |
| 42 | 27.9 | 77 |
| 43 | 29.0 | 25 |
| 44 | 29.5 | 122 |
| 45 | 30.3 | 25 |
| 46 | 30.5 | 45 |
| 47 | 31.0 | 13 |
| 48 | 32.5 | 13 |
| 49 | 33.3 | 13 |
| 50 | 33.6 | 11 |
| 51 | 34.9 | 21 |
| 52 | 36.7 | 11 |
| 53 | 37.5 | 11 |
| 54 | 39.4 | 11 |

TABLE G (Form G)

| Peak No. | 2Theta (deg) | Intensity (Counts) |
|---|---|---|
| 1 | 6.3 | 8 |
| 2 | 9.0 | 7 |
| 3 | 10.3 | 3 |
| 4 | 11.1 | 3 |
| 5 | 12.2 | 14 |
| 6 | 13.0 | 5 |
| 7 | 14.8 | 17 |
| 8 | 16.1 | 15 |
| 9 | 17.4 | 79 |
| 10 | 18.5 | 80 |
| 11 | 20.5 | 50 |
| 12 | 21.4 | 53 |
| 13 | 23.0 | 52 |
| 14 | 24.5 | 35 |
| 15 | 25.8 | 27 |
| 16 | 26.4 | 17 |
| 17 | 29.2 | 2 |
| 18 | 30.4 | 6 |
| 19 | 32.1 | 3 |
| 20 | 32.8 | 3 |
| 21 | 34.9 | 3 |
| 22 | 35.7 | 6 |
| 23 | 36.5 | 2 |
| 24 | 38.1 | 5 |
| 25 | 39.1 | 4 |

TABLE H (Form H)

| Peak No. | 2Theta (deg) | Intensity (Counts) |
|---|---|---|
| 1 | 9.4 | 42 |
| 2 | 9.6 | 167 |
| 3 | 11.5 | 60 |
| 4 | 11.8 | 113 |
| 5 | 12.2 | 162 |
| 6 | 13.5 | 46 |
| 7 | 13.8 | 252 |
| 8 | 14.1 | 26 |
| 9 | 15.3 | 52 |
| 10 | 15.8 | 188 |
| 11 | 16.7 | 168 |
| 12 | 17.7 | 45 |
| 13 | 19.2 | 868 |
| 14 | 19.6 | 81 |

TABLE H-continued (Form H)

| Peak No. | 2Theta (deg) | Intensity (Counts) |
| --- | --- | --- |
| 15 | 20.7 | 138 |
| 16 | 21.3 | 41 |
| 17 | 21.8 | 280 |
| 18 | 22.2 | 734 |
| 19 | 22.6 | 187 |
| 20 | 22.9 | 49 |
| 21 | 23.5 | 138 |
| 22 | 23.8 | 107 |
| 23 | 24.3 | 196 |
| 24 | 24.9 | 486 |
| 25 | 25.6 | 196 |
| 26 | 26.0 | 30 |
| 27 | 26.3 | 75 |
| 28 | 27.4 | 66 |
| 29 | 28.0 | 155 |
| 30 | 28.9 | 48 |
| 31 | 29.4 | 46 |
| 32 | 29.9 | 171 |
| 33 | 30.72 | 70 |
| 34 | 30.9 | 40 |
| 35 | 32.9 | 94 |
| 36 | 33.5 | 31 |
| 37 | 34.2 | 36 |
| 38 | 35.1 | 112 |
| 39 | 36.0 | 35 |
| 40 | 38.0 | 42 |
| 41 | 39.1 | 34 |

TABLE I (Form I)

| Peak No. | 2Theta (deg) | Intensity (Counts) |
| --- | --- | --- |
| 1 | 8.3 | 26 |
| 2 | 8.8 | 36 |
| 3 | 9.8 | 34 |
| 4 | 10.7 | 72 |
| 5 | 11.1 | 629 |
| 6 | 12.1 | 101 |
| 7 | 15.3 | 138 |
| 8 | 16.1 | 34 |
| 9 | 16.6 | 95 |
| 10 | 17.0 | 121 |
| 11 | 17.1 | 175 |
| 12 | 18.9 | 122 |
| 13 | 19.5 | 106 |
| 14 | 20.5 | 466 |
| 15 | 21.0 | 102 |
| 16 | 21.2 | 173 |
| 17 | 21.6 | 149 |
| 18 | 21.9 | 284 |
| 19 | 22.1 | 173 |
| 20 | 24.3 | 166 |
| 21 | 26.0 | 86 |
| 22 | 26.3 | 204 |
| 23 | 26.8 | 23 |
| 24 | 26.9 | 31 |
| 25 | 27.7 | 20 |
| 26 | 27.9 | 75 |
| 27 | 28.1 | 36 |
| 28 | 28.6 | 27 |
| 29 | 29.5 | 47 |
| 30 | 29.9 | 64 |
| 31 | 31.3 | 43 |
| 32 | 31.5 | 50 |
| 33 | 32.1 | 44 |
| 34 | 32.4 | 298 |
| 35 | 32.5 | 76 |
| 36 | 32.7 | 20 |
| 37 | 34.0 | 51 |
| 38 | 34.4 | 19 |
| 39 | 34.6 | 26 |

TABLE I-continued (Form I)

| Peak No. | 2Theta (deg) | Intensity (Counts) |
| --- | --- | --- |
| 40 | 34.9 | 25 |
| 41 | 36.9 | 22 |
| 42 | 37.1 | 22 |

TABLE J (Form J)

| Peak No. | 2Theta (deg) | Intensity (Counts) |
| --- | --- | --- |
| 1 | 7.1 | 111 |
| 2 | 10.5 | 56 |
| 3 | 12.9 | 91 |
| 4 | 14.2 | 646 |
| 5 | 16.6 | 61 |
| 6 | 16.9 | 67 |
| 7 | 17.8 | 364 |
| 8 | 18.7 | 393 |
| 9 | 20.0 | 200 |
| 10 | 20.9 | 459 |
| 11 | 21.4 | 53 |
| 12 | 23.4 | 263 |
| 13 | 23.9 | 836 |
| 14 | 25.2 | 1559 |
| 15 | 26.0 | 296 |
| 16 | 26.3 | 595 |
| 17 | 26.7 | 60 |
| 18 | 27.1 | 90 |
| 19 | 29.3 | 49 |
| 20 | 29.5 | 185 |
| 21 | 29.8 | 73 |
| 22 | 30.2 | 58 |
| 23 | 31.7 | 82 |
| 24 | 33.3 | 65 |
| 25 | 36.0 | 87 |

TABLE K (Form K)

| Peak No. | 2Theta (deg) | Intensity (Counts) |
| --- | --- | --- |
| 1 | 6.4 | 39 |
| 2 | 9.5 | 17 |
| 3 | 10.6 | 122 |
| 4 | 12.7 | 53 |
| 5 | 14.5 | 94 |
| 6 | 15.2 | 80 |
| 7 | 17.4 | 429 |
| 8 | 19.0 | 68 |
| 9 | 19.7 | 285 |
| 10 | 20.5 | 61 |
| 11 | 21.3 | 208 |
| 12 | 22.3 | 86 |
| 13 | 23.3 | 62 |
| 14 | 24.0 | 55 |
| 15 | 24.7 | 279 |
| 16 | 25.9 | 38 |
| 17 | 26.5 | 26 |
| 18 | 28.1 | 36 |
| 19 | 28.6 | 74 |
| 20 | 29.6 | 139 |
| 21 | 30.8 | 39 |
| 22 | 32.3 | 19 |
| 23 | 33.8 | 21 |
| 24 | 34.6 | 30 |
| 25 | 35.5 | 24 |
| 26 | 39.6 | 30 |

TABLE L (Form L)

| Peak No. | 2Theta (deg) | Intensity (Counts) |
|---|---|---|
| 1 | 8.7 | 21 |
| 2 | 9.1 | 175 |
| 3 | 9.7 | 14 |
| 4 | 10.1 | 152 |
| 5 | 10.7 | 10 |
| 6 | 11.1 | 67 |
| 7 | 11.5 | 44 |
| 8 | 12.0 | 152 |
| 9 | 12.6 | 11 |
| 10 | 12.9 | 114 |
| 11 | 13.9 | 52 |
| 12 | 14.4 | 94 |
| 13 | 14.9 | 279 |
| 14 | 16.1 | 148 |
| 15 | 16.9 | 52 |
| 16 | 17.2 | 214 |
| 17 | 17.6 | 20 |
| 18 | 18.3 | 102 |
| 19 | 19.0 | 327 |
| 20 | 19.5 | 43 |
| 21 | 20.0 | 50 |
| 22 | 20.3 | 134 |
| 23 | 21.2 | 348 |
| 24 | 21.7 | 12 |
| 25 | 22.2 | 78 |
| 26 | 22.7 | 41 |
| 27 | 23.3 | 170 |
| 28 | 24.0 | 289 |
| 29 | 25.4 | 43 |
| 30 | 25.8 | 107 |
| 31 | 26.3 | 17 |
| 32 | 27.2 | 44 |
| 33 | 27.5 | 119 |
| 34 | 28.1 | 121 |
| 35 | 28.8 | 30 |
| 36 | 29.7 | 12 |
| 37 | 30.2 | 95 |
| 38 | 30.7 | 34 |
| 39 | 30.9 | 26 |
| 40 | 32.0 | 14 |
| 41 | 32.3 | 32 |
| 42 | 32.8 | 20 |
| 43 | 34.2 | 30 |
| 44 | 34.9 | 42 |
| 45 | 35.9 | 14 |
| 46 | 37.1 | 10 |
| 47 | 37.9 | 12 |
| 48 | 38.1 | 12 |
| 49 | 38.5 | 14 |
| 50 | 38.9 | 15 |

TABLE M (Form M)

| Peak No. | 2Theta (deg) | Intensity (Counts) |
|---|---|---|
| 1 | 8.6 | 26 |
| 2 | 10.2 | 101 |
| 3 | 10.4 | 127 |
| 4 | 11.9 | 19 |
| 5 | 12.2 | 72 |
| 6 | 14.3 | 27 |
| 7 | 14.7 | 509 |
| 8 | 15.0 | 53 |
| 9 | 16.0 | 27 |
| 10 | 16.4 | 269 |
| 11 | 16.8 | 89 |
| 12 | 17.2 | 135 |
| 13 | 17.5 | 56 |
| 14 | 18.1 | 75 |
| 15 | 18.5 | 22 |
| 16 | 18.8 | 78 |
| 17 | 19.1 | 228 |
| 18 | 19.4 | 291 |
| 19 | 19.9 | 190 |
| 20 | 20.8 | 70 |
| 21 | 21.3 | 600 |
| 22 | 21.6 | 43 |
| 23 | 21.9 | 42 |
| 24 | 22.3 | 29 |
| 25 | 22.8 | 108 |
| 26 | 23.7 | 30 |
| 27 | 23.8 | 74 |
| 28 | 24.2 | 381 |
| 29 | 24.7 | 131 |
| 30 | 25.2 | 32 |
| 31 | 25.4 | 154 |
| 32 | 25.6 | 547 |
| 33 | 26.0 | 97 |
| 34 | 26.9 | 124 |
| 35 | 27.3 | 52 |
| 36 | 27.5 | 33 |
| 37 | 27.8 | 45 |
| 38 | 28.0 | 81 |
| 39 | 28.6 | 47 |
| 40 | 28.9 | 43 |
| 41 | 29.6 | 19 |
| 42 | 30.6 | 29 |
| 43 | 30.8 | 40 |
| 44 | 30.9 | 31 |
| 45 | 31.5 | 60 |
| 46 | 32.4 | 31 |
| 47 | 32.6 | 29 |
| 48 | 33.2 | 28 |
| 49 | 33.8 | 21 |
| 50 | 33.9 | 41 |
| 51 | 34.7 | 20 |
| 52 | 35.9 | 18 |
| 53 | 36.2 | 22 |
| 54 | 36.4 | 27 |
| 55 | 37.2 | 36 |
| 56 | 37.4 | 28 |
| 57 | 38.5 | 44 |
| 58 | 38.7 | 22 |

TABLE N (Form N)

| Peak No. | 2Theta (deg) | Intensity (Counts) |
|---|---|---|
| 1 | 7.7 | 23 |
| 2 | 9.1 | 27 |
| 3 | 9.6 | 12 |
| 4 | 10.0 | 82 |
| 5 | 11.5 | 26 |
| 6 | 12.2 | 40 |
| 7 | 12.6 | 34 |
| 8 | 14.5 | 50 |
| 9 | 15.0 | 11 |
| 10 | 15.3 | 61 |
| 11 | 16.1 | 106 |
| 12 | 16.7 | 84 |
| 13 | 17.7 | 46 |
| 14 | 18.0 | 175 |
| 15 | 18.6 | 126 |
| 16 | 18.9 | 236 |
| 17 | 19.1 | 369 |
| 18 | 20.1 | 252 |
| 19 | 20.7 | 167 |
| 20 | 21.1 | 160 |
| 21 | 21.6 | 46 |
| 22 | 22.3 | 36 |
| 23 | 22.9 | 55 |
| 24 | 23.4 | 278 |

TABLE N-continued (Form N)

| Peak No. | 2Theta (deg) | Intensity (Counts) |
|---|---|---|
| 25 | 24.5 | 282 |
| 26 | 25.4 | 77 |
| 27 | 25.8 | 25 |
| 28 | 26.6 | 56 |
| 29 | 27.0 | 165 |
| 30 | 27.3 | 46 |
| 31 | 28.3 | 62 |
| 32 | 28.7 | 47 |
| 33 | 29.4 | 12 |
| 34 | 29.8 | 64 |
| 35 | 30.5 | 18 |
| 36 | 31.5 | 15 |
| 37 | 32.1 | 16 |
| 38 | 32.4 | 28 |
| 39 | 32.9 | 12 |
| 40 | 33.7 | 31 |
| 41 | 34.0 | 22 |
| 42 | 34.9 | 23 |
| 43 | 35.4 | 13 |
| 44 | 35.8 | 29 |
| 45 | 36.9 | 27 |
| 46 | 38.3 | 11 |
| 47 | 39.4 | 15 |
| 48 | 39.9 | 12 |

TABLE O (Form O)

| Peak No. | 2Theta (deg) | Intensity (Counts) |
|---|---|---|
| 1 | 12.6 | 175 |
| 2 | 17.0 | 583 |
| 3 | 17.2 | 2631 |
| 4 | 17.4 | 159 |
| 5 | 17.8 | 162 |
| 6 | 18.5 | 425 |
| 7 | 19.5 | 81 |
| 8 | 19.7 | 103 |
| 9 | 20.7 | 85 |
| 10 | 20.9 | 275 |
| 11 | 22.7 | 187 |
| 12 | 22.8 | 103 |
| 13 | 24.7 | 115 |
| 14 | 25.0 | 311 |
| 15 | 25.3 | 1698 |
| 16 | 25.4 | 355 |
| 17 | 25.5 | 101 |
| 18 | 28.0 | 148 |
| 19 | 30.3 | 148 |
| 20 | 33.1 | 207 |
| 21 | 34.7 | 102 |

TABLE P (Form P)

| Peak No. | 2Theta (deg) | Intensity (Counts) |
|---|---|---|
| 1 | 7.2 | 46 |
| 2 | 8.5 | 80 |
| 3 | 9.0 | 31 |
| 4 | 9.8 | 26 |
| 5 | 10.2 | 211 |
| 6 | 10.8 | 34 |
| 7 | 12.1 | 42 |
| 8 | 12.6 | 43 |
| 9 | 13.3 | 22 |
| 10 | 13.7 | 108 |
| 11 | 14.1 | 29 |
| 12 | 15.4 | 34 |

TABLE P-continued (Form P)

| Peak No. | 2Theta (deg) | Intensity (Counts) |
|---|---|---|
| 13 | 16.4 | 39 |
| 14 | 17.0 | 587 |
| 15 | 17.9 | 87 |
| 16 | 18.4 | 73 |
| 17 | 18.7 | 89 |
| 18 | 19.6 | 183 |
| 19 | 20.1 | 27 |
| 20 | 20.9 | 125 |
| 21 | 21.4 | 227 |
| 22 | 21.7 | 67 |
| 23 | 22.7 | 273 |
| 24 | 23.3 | 127 |
| 25 | 23.7 | 140 |
| 26 | 24.2 | 48 |
| 27 | 24.7 | 55 |
| 28 | 25.4 | 265 |
| 29 | 26.1 | 69 |
| 30 | 27.0 | 65 |
| 31 | 28.1 | 175 |
| 32 | 28.9 | 38 |
| 33 | 30.2 | 32 |
| 34 | 30.7 | 21 |
| 35 | 31.2 | 60 |
| 36 | 32.5 | 22 |
| 37 | 33.5 | 25 |
| 38 | 34.0 | 30 |
| 39 | 34.6 | 34 |
| 40 | 36.4 | 27 |
| 41 | 37.9 | 21 |
| 42 | 39.6 | 31 |

The present invention provides methods for inhibiting the enzyme Raf kinase. Since the enzyme is a downstream effector of $p21^{ras}$, the instant solid forms are useful alone or in pharmaceutical compositions for human or veterinary use where inhibition of the raf kinase pathway is indicated, e.g., in the treatment of tumors and/or cancerous cell growth mediated by Raf kinase. In particular, the solid forms are useful in the treatment of human or animal (e.g., murine) cancer, since the progression of these cancers can often be dependent upon the Ras protein signal transduction cascade and therefore is susceptible to treatment by interruption of the cascade by inhibiting Raf kinase activity. Accordingly, the solid forms of the invention are useful in treating a variety of cancers, including solid cancers such as for example, carcinomas (e.g., of the lungs, pancreas, thyroid, bladder or colon), myeloid disorders (e.g., myeloid leukemia, multiple myeloma, and erythroleukemia), adenomas (e.g., villous colon adenoma), sarcomas (e.g., osteosarcoma), and the like.

As used throughout, the term "cancer" refers to cancer diseases that can be beneficially treated by the inhibition of a kinase, particularly Raf kinase, including, for example, solid cancers, such as those described above including carcinomas (e.g., of the lungs, pancreas, thyroid, ovarian, bladder, breast, prostate, or colon), melanomas, myeloid disorders (e.g., myeloid leukemia, multiple myeloma, and erythroleukemia), adenomas (e.g., villous colon adenoma), and sarcomas (e.g., osteosarcoma). In some embodiments, the cancer is melanoma. In some embodiments, the cancer is breast cancer. In some embodiments, the cancer is prostate cancer.

"Raf inhibitor" is used herein to refer to a compound that exhibits an $IC_{50}$ with respect to Raf Kinase activity of no more than about 100 μM and more typically not more than about 50 μM, as measured in the Raf/Mek Filtration Assay described generally hereinbelow in the Examples. Preferred isoforms of Raf kinase in which the solid forms of the present invention can inhibit, include A-Raf, B-Raf, and C-Raf (Raf-1). "$IC_{50}$"

is that concentration of inhibitor which reduces the activity of an enzyme (e.g., Raf kinase) to half-maximal level.

Methods of treating the diseases listed herein are understood to involve administering to a human or animal in need of such treatment an effective amount of the solid form of the invention, or composition containing the same. As used herein, the term "treating" in reference to a disease is meant to refer to preventing, inhibiting and/or ameliorating the disease. As used herein, the phrase "effective amount" refers to the amount of active compound or pharmaceutical agent that elicits the biological or medicinal response in a tissue, system, animal or human that is being sought by a researcher, veterinarian, medical doctor or other clinician. In some embodiments, the effective amounts of the solid forms of the invention generally include any amount sufficient to detectably inhibit Raf activity by any of the assays described herein, by other Raf kinase activity assays known to or readily ascertained by those having ordinary skill in the art or by detecting an inhibition or alleviation of symptoms of cancer.

In another aspect, the present invention relates to methods of inhibiting at least one serine/threonine kinase in the MAPK signaling pathway in a subject, or treating a biological condition mediated by a serine/threonine kinase in the MAPK signaling pathway in a subject, comprising administering a solid form of the invention in an amount effective to inhibit the activity of the at least one serine/threonine kinase in the MAPK signaling pathway in the subject.

As used herein, the phrase "MAPK signal transduction pathway" is an abbreviation that stands for Mitogen activated protein kinase signal transduction pathway in a module that is formed of the Ras-Raf-MEK1-ERK signaling molecules.

The therapeutic compositions in accordance with this aspect of the invention are useful for treating patients with a need for such inhibitors (e.g., those suffering from cancer mediated by abnormal MAPK signaling). Cancer types mediated by abnormal MAPK signaling include, for example, melanoma, papillary thyroid cancer, thyroid cancer, ovarian cancer, colon cancer, pancreatic cancer, lung cancer (e.g., non-small cell lung cancer (NSCLC)), leukemia (acute lymphoblastic leukemia (ALL) and acute myeloid leukemia) and the like. Abnormal MAPK signaling may be inhibited by administering a compound that inhibits wild-type or mutant forms of Ras, Raf, MEK or ERK.

In one embodiment, the invention provides a method of inhibiting Ras (wild-type or mutant Ras). The method includes administering an effective amount of any of the solid forms described herein to a subject in need thereof.

In one embodiment, the invention provides a method of inhibiting Raf (wild-type, or mutant B-Raf). The method includes administering an effective amount of any of the solid forms described herein to a subject in need thereof.

In one embodiment, the invention provides a method of inhibiting MEK. The method includes administering an effective amount of any of the solid forms described herein to a subject in need thereof.

In one embodiment, the invention provides a method of inhibiting ERK. The method includes administering an effective amount of any of the solid forms described herein to a subject in need thereof.

In another aspect, the present invention relates to methods of inhibiting at least one tyrosine kinase receptor selected from the group consisting of VEGFR-2, PDGFR-β, pERK, bFGF, FGFR1, FGFR2, FGFR3, c-Kit and CSF-1R in a subject, or treating a biological condition mediated by at least one of VEGFR-2, PDGFR-β, pERK, bFGF, FGFR1, FGFR2, FGFR3, c-Kit and CSF-1R, comprising administering a therapeutic composition comprising at least one solid form of the invention in an amount effective to inhibit the tyrosine kinase receptor in the subject.

The therapeutic solid forms in accordance with this aspect of the invention are useful for treating patients with a need for such inhibitors (e.g., those suffering from cancer mediated by abnormal tyrosine kinase receptor signaling). Cancers mediated by abnormal tyrosine kinase receptor signaling include, for example, melanoma, breast cancer, bladder cancer, lung cancer, thyroid cancer, prostate cancer, ovarian cancer, mast cell leukemia, germ cell tumors, small-cell lung carcinoma, gastrointestinal stromal tumors, acute myelogenous leukemia (AML), neuroblastoma, and pancreatic cancer. Further cancers mediated by abnormal tyrosine kinase receptor include leukemia, erythroleukemia, germ cell tumors, small-cell lung carcinoma, gastrointestinal stromal tumors, acute myelogenous leukemia, neuroblastoma, melanoma, multiple myeloma, ovarian carcinoma, and breast carcinoma.

In one embodiment, the invention provides a method of inhibiting VEGFR-2. The method includes administering an effective amount of a solid form of the invention to a subject in need thereof. The method may be useful to treat a solid tumor by inhibiting angiogenesis.

In one embodiment, the invention provides a method of inhibiting PDGFR-β. The method includes administering an effective amount of a solid form of the invention to a subject in need thereof.

In one embodiment, the invention provides a method of inhibiting c-Kit. The method includes administering an effective amount of a solid form of the invention to a subject in need thereof.

In one embodiment, the invention provides a method of inhibiting CSF-1R. The method includes administering an effective amount of a solid form of the invention to a subject in need thereof.

As described herein, the solid forms of the invention are useful in vitro or in vivo in inhibiting the growth of cancer cells. The compounds may be used alone or in compositions together with one or more pharmaceutically acceptable carriers or excipients. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

The solid forms of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The solid forms of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq. (1976).

While the solid forms of the invention can be administered as the sole active pharmaceutical agent, they can also be used in combination with one or more other agents used in the treatment of cancer. The compounds of the present invention are also useful in combination with known therapeutic agents and anti-cancer agents, and combinations of the presently disclosed compounds with other anti-cancer or chemotherapeutic agents are within the scope of the invention. Examples of such agents can be found in *Cancer Principles and Practice of Oncology*, V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents, and agents that interfere with cell cycle checkpoints. The solid forms of the invention are also useful when co-administered with radiation therapy.

Therefore, in one embodiment of the invention, the compounds of the invention are also used in combination with known anticancer agents including, for example, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

Estrogen receptor modulators are compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2, 2-dimethylpropanoate, 4,4'-dihydroxybenzophenone-2,4-dinitrophenyl-hydrazone, and SH646.

Androgen receptor modulators are compounds which interfere with or inhibit the binding of androgens to an androgen receptor. Representative examples of androgen receptor modulators include finasteride and other 5α-reductase inhibitors, nilutamide, flutamide, bicalutamide, liarozole, and abiraterone acetate. Retinoid receptor modulators are compounds which interfere or inhibit the binding of retinoids to a retinoid receptor. Examples of retinoid receptor modulators include bexarotene, tretinoin, 13-cis-retinoic acid, 9-cis-retinoic acid, α-difluoromethylornithine, LX23-7553, trans-N-(4'-hydroxyphenyl) retinamide, and N4-carboxyphenyl retinamide.

Cytotoxic and/or cytostatic agents are compounds which cause cell death or inhibit cell proliferation primarily by interfering directly with the cell's functioning or inhibit or interfere with cell mytosis, including alkylating agents, tumor necrosis factors, intercalators, hypoxia activatable compounds; microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors, and ubiquitin ligase inhibitors. Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine (chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032). A representative example of a hypoxia activatable compound is tirapazamine. Proteasome inhibitors include, but are not limited to, lactacystin and bortezomib. Examples of microtubule inhibitors/microtubule-stabilizing agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. Representative examples of topoisomerase inhibitors include topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13 (9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroOxy-3,5-dimethoxyphenyl]-5,5a,6,8,8a,9-hexahydrofuro(3',4':6,7)naphtho(2,3-d)-1,3-dioxol-6-one, 2,3-(methylenedioxy)-5-methyl-7-hydroxy-8-methoxybenzo [c]-phenanthridinium, 6,9-bis[(2-aminoethyl)amino]benzo[g]isoquinoline-5,10-dione, 5-(3-aminopropylamino)-7,10-dihydroxy-2-(2-hydroxyethyl-aminomethyl)-6H-pyrazolo [4,5,1'-de]acridin-6-one, N-[1-[2 (diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna. Examples of inhibitors of mitotic kinesins, such as the human mitotic kinesin KSP, are described in PCT Publications WO 01/30768 and WO 01/98278, WO 03/050,064 (Jun. 19, 2003), WO 03/050,122 (Jun. 19, 2003), WO 03/049,527 (Jun. 19, 2003), WO 03/049,679 (Jun. 19, 2003), WO 03/049,678 (Jun. 19, 2003) and WO 03/39460 (May 15, 2003) and pending PCT Appl. Nos. US03/06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1, and inhibitors of Rab6-KIFL.

Inhibitors of kinases involved in mitotic progression include, but are not limited to, inhibitors of aurora kinase, inhibitors of Polo-like kinases (PLK) (e.g., inhibitors of PLK-1), inhibitors of bub-1 and inhibitors of bub-R1. Antiproliferative agents include antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl] adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1-diazatetracyclo (7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. Examples of monoclonal antibody targeted therapeutic agents include those therapeutic agents which have cytotoxic agents or radioisotopes attached to a cancer cell specific or target cell specific monoclonal antibody. Examples include, for example, Bexxar. HMG-CoA reductase inhibitors are inhibitors of 3-hydroxy-3-methylglutaryl-CoA reductase. Compounds which have inhibitory activity for HMG-CoA reductase can be readily identified by using assays well-known in the art such as those described or cited in U.S. Pat. No. 4,231,938 and WO 84/02131. Examples of HMG-CoA reductase inhibitors that may be used include, but are not limited to, lovastatin (MEVACOR®; see U.S. Pat. Nos. 4,231,938, 4,294,926, and 4,319,039), simvastatin (ZOCOR®; see U.S. Pat. Nos. 4,444,784, 4,820,850, and 4,916, 239), pravastatin (PRAVACHOL®; see U.S. Pat. Nos. 4,346, 227, 4,537,859, 4,410,629, 5,030,447, and 5,180,589), fluvastatin (LESCOL®; see U.S. Pat. Nos. 5,354,772, 4,911, 165, 4,929,437, 5,189,164, 5,118,853, 5,290,946, and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. In an embodiment, the HMG-CoA reductase inhibitor is selected from lovastatin and simvastatin.

Prenyl-protein transferase inhibitors are compounds which inhibit any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)quinolinone, (−)-6-[amino(4-chlorophenyl)(1-methyl-1H-imidazol-5-yl) methyl]-4-(3-chlorophenyl)-1-methyl-2(1H)-quinolinone, (+)-6-[amino(4-chlorophenyl)(1-methyl-1H-imidazol-5-yl) methyl]-4-(3-chlorophenyl)-1-methyl-2(1H)-quinolinone, 5(S)-n-butyl-1-(2,3-dimethylphenyl)-4-[1-(4-cyanobenzyl)-5-imidazolylmethyl-2-piperazinone, (S)-1-(3-chlorophenyl)-4-[1-(4-cyanobenzyl)-5-imidazolylmethyl]-5-[2-(ethanesulfonyl)methyl)-2-piperazinone, 5(S)-n-butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{-[4-hydroxymethyl-4-(4-chloropyridin-2-ylmethyl)-piperidine-1-ylmethyl]-2-methylimidazol-1-ylmethyl}benzonitrile, 4-{-5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2'] bipyridin-5'-ylmethyl]-3H-imidazol-4-ylmethyl}benzonitrile, 4-{3-[4-(2-oxo-2H-[1,2]bipyridin-5'-ylmethyl]-3H-imidazol-4-ylmethyl}benzonitrile, 4-[3-(2- oxo-1-phenyl-1,2-dihydropyridin-4-ylmethyl)-3H-midazol-4-ylmethyl}benzonitrile, 18,19-dihydro-19-oxo-5H,17H-6,10:12,16-dimetheno-1H-imidazo[4,3-c][1,11,4]dioxaazacyclo-nonadecine-9-carbonitrile, (±)-19,20-dihydro-19-oxo-5H-18,21-ethano-12,14-etheno-6,10-metheno-22H-benzo[d]imidazo[4,3-k]-[1,6,9,12]oxatriaza-cyclooctadecine-9-carbonitrile, 19,20-dihydro-19-oxo-5H,17H-18,21-ethano-6,10:12,16-dimetheno-22H-imidazo[3,4-h][1,8,11,14]oxatriazacycloeicosine-9-carbonitrile, and (+−)-19,20-dihydro-3-methyl-19-oxo-5H-18,21-ethano-12,14-etheno-6,10-metheno-22H-benzo[d]imidazo[4,3-k][1,6,9,12]oxatriazacyclooctadecine-9-carbonitrile. Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer* 35(9):1394-1401 (1999).

Angiogenesis inhibitors refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-.alpha., interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS 89:7384 (1992); *JNCI* 69:475 (1982); *Arch. Opthalmol.* 108:573 (1990); *Anat. Rec.*, (238):68 (1994); *FEBS Letters* 372:83 (1995); *Clin, Orthop.* 313:76 (1995); *J. Mol. Endocrinol.* 16:107 (1996); *Jpn. J. Pharmacol.* 75:105 (1997); *Cancer Res.* 57:1625 (1997); *Cell* 93:705 (1998); *Intl. J. Mol. Med.* 2:715 (1998); *J. Biol. Chem.* 274:9116 (1999)), steroidal anti-inflammatories (such as corticosteroids, mineralocorticoids, dexamethasone, prednisone, prednisolone, methylpred, betamethasone), carboxyamidotriazole, combretastatin A4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology,* 17:963-968 (October 1999); Kim et al., *Nature*, 362:841-844 (1993); WO 00/44777; and WO 00/61186). Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002). The invention also encompasses combinations of the compounds of the invention with NSAIDs which are selective COX-2 inhibitors (generally defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays). Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference. Representative inhibitors of COX-2 that are useful in the methods of the present invention include 3-phenyl-4-(4-(methylsulfonyl) phenyl)-2-(5H)-furanone; and 5-chloro-3-(4-methylsulfonyl)phenyl-2-(2-methyl-5-pyridinyl)pyridine. Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nova 14, 1995, U.S. Pat. No. 5,633,272, issued May 27, 1997, U.S. Pat. No. 5,932,598, issued Aug. 3, 1999, U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998. Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]carbonylimino]-bis-(1,3-naphthalene disulfonate), and 3-[(2,4-dimethylpyrrol-5-yl)methylene]-2-indolinone (SU5416).

Agents that interfere with cell cycle checkpoints are compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

Inhibitors of cell proliferation and survival signaling pathway are pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in WO 02/083064, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779). Such agents include small molecule inhibitor compounds and antibody antagonists.

Apoptosis inducing agents include activators of TNF receptor family members (including the TRAIL receptors).

In some embodiments of the invention, representative agents useful in combination with the solid forms of the invention for the treatment of cancer include, for example, irinotecan, topotecan, gemcitabine, 5-fluorouracil, leucovorin carboplatin, cisplatin, taxanes, tezacitabine, cyclophosphamide, vinca alkaloids, imatinib (Gleevec), anthracyclines, rituximab, trastuzumab, as well as other cancer chemotherapeutic agents.

The above compounds to be employed in combination with the solid forms of the invention will be used in therapeutic amounts as indicated in the *Physicians' Desk Reference* (PDR) 47th Edition (1993), which is incorporated herein by reference, or such therapeutically useful amounts as would be known to one of ordinary skill in the art.

The solid forms of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

Antiestrogens, such as tamoxifen, inhibit breast cancer growth through induction of cell cycle arrest, that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to antiestrogen resistance (Donovan et al., *J. Biol. Chem.* 276:40888, 2001). As reported by Donovan et al., inhibition of MAPK signaling through treatment with MEK inhibitor changed the phosphorylation status of p27 in hormone refactory breast cancer cell lines and in so doing restored hormone sensitivity. Accordingly, in one aspect, any of the solid forms described herein may be used in the treatment of hormone dependent cancers, such as breast and prostate cancers, to reverse hormone resistance commonly seen in these cancers with conventional anticancer agents.

In hematological cancers, such as chronic myelogenous leukemia (CML), chromosomal translocation is responsible for the constitutively activated BCR-AB1 tyrosine kinase. The afflicted patients are responsive to Gleevec, a small molecule tyrosine kinase inhibitor, as a result of inhibition of Ab1 kinase activity. However, many patients with advanced stage disease respond to Gleevec initially, but then relapse later due to resistance-conferring mutations in the Ab1 kinase domain. In vitro studies have demonstrated that BCR-Av1 employs the Raf kinase pathway to elicit its effects. In addition, inhibiting more than one kinase in the same pathway provides additional protection against resistance-conferring mutations. Accordingly, in another aspect of the invention, any of the solid forms described herein can be used in combination with at least one additional agent, such as Gleevec, in the treatment of hematological cancers, such as chronic myelogenous leukemia (CML), to reverse or prevent resistance to the at least one additional agent.

In order that the invention disclosed herein may be more efficiently understood, examples are provided below. It should be understood that these examples are for illustrative purposes only and are not to be construed as limiting the invention in any manner.

EXAMPLES

Example 1

Preparation of Form A

Method 1

Figure 33:
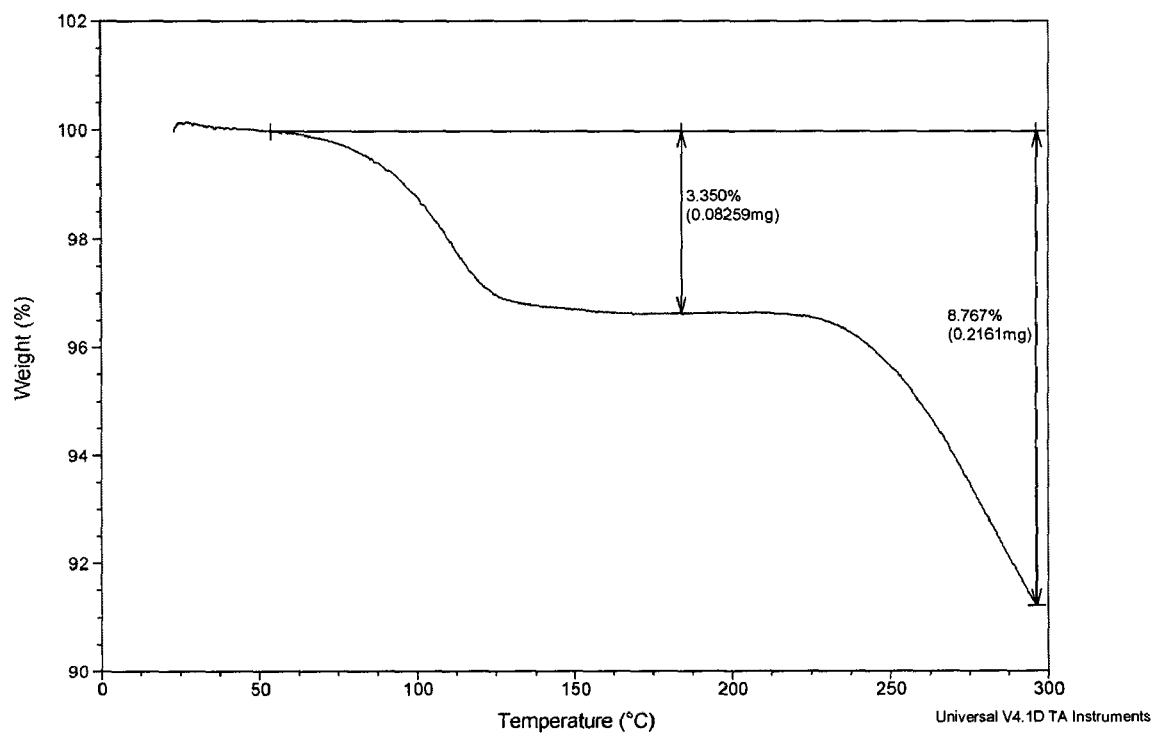
FIG. 33 depicts a TGA thermogram consistent with Form A.

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (753 mg) was suspended in 17 mL of a mixture of 46% acetic acid and 54% water. The resulting mixture was cooled from 85 to 24° C. over 24 h, then kept at 4° C. for 24 h. The solids were filtered, washed with water, and air-dried for at least 2 days. The crystalline product was analyzed by XRPD, DSC, and TGA (See FIGS. 1, 17, and 33).

Method 2

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (649 mg) was dissolved in 10 mL of acetonitrile. The resulting mixture was cooled from 85 to 24° C. over 24 h, then kept at 4° C. for 24 h. The solids were filtered and air-dried for 2 days. The crystalline product was analyzed by XRPD, DSC, and TGA and found to be consistent with Form A.

Method 3

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (200 mg) was suspended in 2 mL of ethyl acetate and stirred at 25° C. for 7 days. The solids were filtered, washed with methylene chloride, and air-dried for 24 h. The crystalline product was analyzed by XRPD, DSC, and TGA and was found to be consistent with Form A.

Method 4

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (200 mg) was suspended in 2 mL of a mixture of 75% ethyl acetate and 25% methylene chloride and stirred at 25° C. for 7 days. The solids were filtered, washed with water, and air-dried for 24 h. The crystalline product was analyzed by XRPD, DSC, and TGA and was found to be consistent with Form A.

Example 2

Preparation of Form B

Method 1

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (1 g) was dissolved in 10 mL of ethyl acetate by heating. The resulting mixture was cooled from 65 to 4° C. over 24 h, then kept at 4° C. for 24 h. The solids were filtered, washed with water, and air-dried for at least 2 days. The crystalline product was analyzed by XRPD, DSC, and TGA (See FIGS. 2, 18, and 34).

Method 2

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (652 mg) was dissolved in 4.5 mL of acetone. The resulting mixture was cooled from 65 to 4° C., then kept at 4° C. for 24 h. The solids were filtered, washed with water, and air-dried for 2 days. The crystalline product was analyzed by XRPD, DSC, and TGA and was found to be consistent with Form B.

Method 3

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (652 mg) was dissolved in 4.5 mL of acetone. The resulting mixture was cooled from 24 to 4° C., then kept at 4° C. for 24 h. The solids were filtered, washed with water, and air-dried for 24 h. The crystalline product was analyzed by XRPD, DSC, and TGA and was found to be consistent with Form B.

Method 4

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (499 mg) was dissolved in 5 mL of ethyl acetate by heating. The resulting mixture was cooled from 24 to 4° C. over 24 h, then kept at 4° C. for 24 h. The solids were filtered, washed with water, and air-dried for 24 h. The crystalline product was analyzed by XRPD, DSC, and TGA and was found to be consistent with Form B.

Method 5

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (904 mg) was dissolved in 6 mL of 2-butanone by heating. The resulting mixture was cooled from 30 to 0° C. over 24 h, then kept at 0° C. for 60 h. The solids were filtered and air-dried for 2 days. The crystalline product was analyzed by XRPD, DSC, and TGA and was found to be consistent with Form B.

Example 3

Preparation of Form C

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (177 mg) was dissolved in 18 mL of hexane. The resulting mixture was cooled from 65 to 4° C., then kept at 4° C. for 24 h. The solids were filtered, washed with water, and air-dried for 2 days. The crystalline product was analyzed by XRPD, DSC, and TGA (See FIGS. 3, 19, and 35).

Example 4

Preparation of Form D

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (182 mg) was suspended in 15 mL of toluene. The resulting mixture was cooled from 85 to 4° C., then kept at 4° C. for 24 h. The solids were filtered, washed with water, and air-dried for 2 days. The crystalline product was analyzed by XRPD, DSC, and TGA (See FIGS. 4, 20, and 36).

Example 5

Preparation of Form E

See Example 17.

Figure 37:
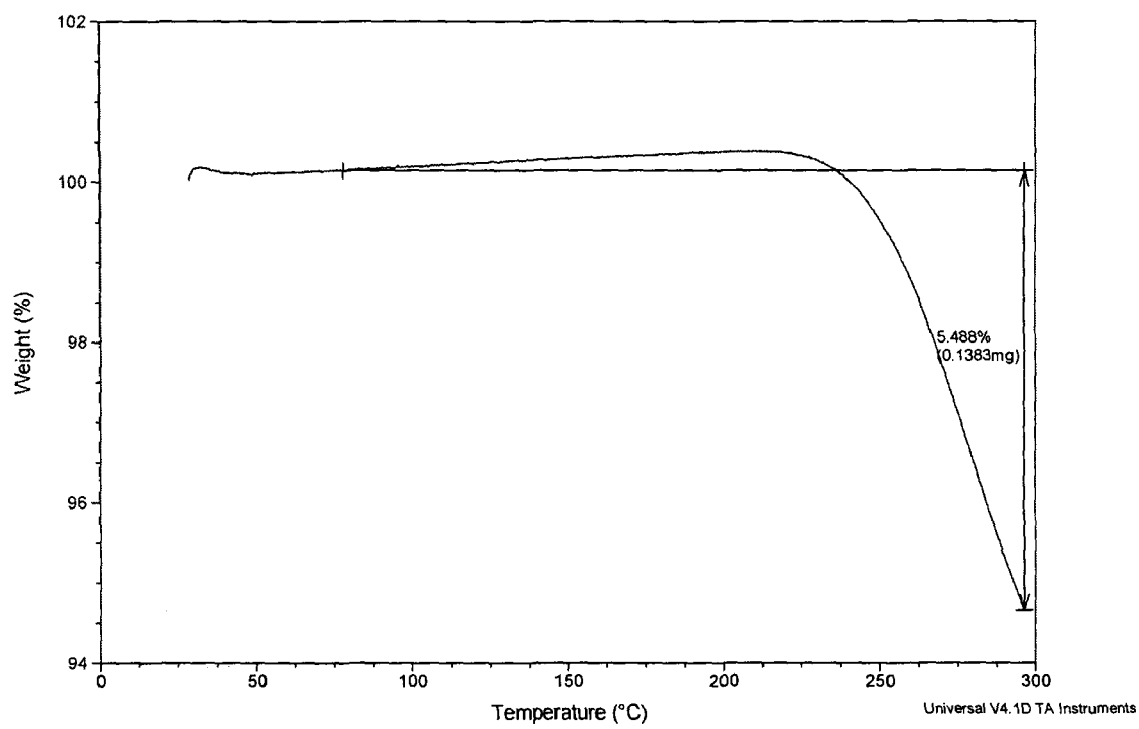
FIG. 37 depicts a TGA thermogram consistent with Form E.

The crystalline product was analyzed by XRPD, DSC, and TGA (See FIGS. 5, 21, and 37).

Example 6

Preparation of Form F

Method 1

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (300 mg) was heated at the maximum heating rate of the oven in a round bottom flask to 215° C. which was held for 15 min. The sample was then cooled gradually at the maximum cooling rate of the oven (Lindberg/Blue M +260° C. Mechanical Convection Oven). The crystalline product was analyzed by XRPD, DSC, and TGA (See FIGS. 6, 22, and 38).

Method 2

Product from Method 1 was added to 1 mL of ethyl acetate to form suspension at 30° C. The mixture was placed in a refrigerator (4° C.) overnight. Then the supernatant was aspirated and the crystalline product dried in a vacuum oven at 50° C. for 40 min. The crystalline product was analyzed by XRPD, DSC, and TGA and was found to be consistent with Form F.

Example 7

Preparation of Form G

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (930 mg) was dissolved in 4 mL of tetrahydrofuran (THF) by heating. The resulting mixture was cooled from 30 to 0° C. over 24 h, then kept at 0° C. for 60 h. The solids were filtered and air-dried for 2 days. The crystalline product was analyzed by XRPD, DSC, and TGA (See FIGS. 7, 23, and 39).

Example 8

Preparation of Form H

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (853.28 mg) was dissolved in 12 mL of ethanol by heating. The resulting mixture was cooled from 85 to 4° C. over 24 h, then kept at 4° C. for 24 h. The solids were filtered and air-dried for 2 days. The crystalline product was analyzed by XRPD, DSC, and TGA (See FIGS. 8, 24, and 40).

Example 9

Preparation of Form I

1-Methyl-5-(2-(5-(trifluoromethyl)-1H-imidazol-2-yl)pyridin-4-yloxy)-N-(4-(trifluoromethyl)phenyl)-1H-benzo[d]

imidazol-2-amine (506 mg) was dissolved in 15 mL of dioxane by heating. The resulting mixture was cooled from 30 to 0° C. over 24 h, then kept at 0° C. for 60 h. The solids were filtered and air-dried for 2 days. The crystalline product was analyzed by XRPD, DSC, and TGA and found to be consisted with Form I.

The filtrate from above was allowed to air-dry for 4 days. The crystalline product was analyzed by XRPD, DSC, and TGA (See FIGS. 9, 25, and 41) and was found consistent with Form I.

Example 10

Preparation of Form J

Method 1
1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (840 mg) was dissolved in 2.5 mL of dimethylacetamide. The resulting mixture was cooled from 85 to 4° C. over 24 h, then kept at 4° C. for 24 h. The solids were filtered and dried in an oven at 50° C. for 24 h. The crystalline product was analyzed by XRPD, DSC, and TGA (See FIGS. 10, 26, and 42).

The filtrate was allowed to air dry for 4 days. The resulting solid was found to be consisted with Form J.
Method 2
1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (929 mg) was dissolved in 3 mL of N-methylpyrrolidinone. The resulting mixture was cooled from 30 to 0° C. over 24 h, then kept at 0° C. for 60 h. The solids were filtered and air-dried for 2 days. The crystalline product was analyzed by XRPD, DSC, and TGA and was found consistent with Form J.

Example 11

Preparation of Form K

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (758 mg) was dissolved in 6 mL of methanol. The resulting mixture was cooled from 65 to 4° C., then kept at 4° C. for 24 h. The solids were filtered, washed with water, and air-dried for 2 days. The crystalline product was analyzed by XRPD, DSC, and TGA (See FIGS. 11, 27, and 43).

Example 12

Preparation of Form L

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (830 mg) was dissolved in 2.95 mL of 20% triethylamine in THF. The material crashed out of solution shortly after going in. The sample was equilibrated at 40° C. for 2 h, then cooled to 0° C. in 400 min, and cycled between 0 and 20° C. for 7 days; 120 min at 0° C., 10 min up to 20° C., 120 at 20° C., 200 min down to 0° C. The solids were filtered and air-dried. The crystalline product was analyzed by XRPD, DSC, and TGA (See FIGS. 12, 28, and 44).

Example 13

Preparation of Form M

1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine (705 mg) was suspended in 9 mL of 20% triethylamine in ethyl acetate. The sample was equilibrated at 40° C. for 2 h, then cooled to 0° C. in 400 min, and cycled between 0 and 20° C. for 7 days; 120 min at 0° C., 10 min up to 20° C., 120 at 20° C., 200 min down to 0° C. The solids were filtered and air-dried. The crystalline product was analyzed by XRPD, DSC, and TGA (See FIGS. 13, 29, and 45).

Example 14

Preparation of Form N

Excess 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine was equilibrated in propylene glycol. The sample was agitated at room temperature for 3 days, then allowed to stand at RT without agitation for an additional day. The sample was then centrifuged, the supernatant was aspirated, and the pellets washed with about 50 mL of water. The resulting solid was allowed to air dry for one day. The product was analyzed by XRPD, DSC, and TGA (See FIGS. 14, 30, and 46).

Example 15

Preparation of Form O

The filtrate from Example 11 was allowed to air-dry for 4 days. The product was analyzed by XRPD, DSC, and TGA (See FIGS. 15, 31, and 47).

Example 16

Preparation of Form P

The filtrate from Example 12 was allowed to air-dry for 4 days. The product was analyzed by XRPD, DSC, and TGA (See FIGS. 16, 32, and 48).

Example 17

Preparation of 1-Methyl-5-(2-(5-(trifluoromethyl)-1H-imidazol-2-yl)pyridin-4-yloxy)-N-(4-(trifluoromethyl)phenyl)-1H-benzo[d]imidazol-2-amine Method A
Step 1

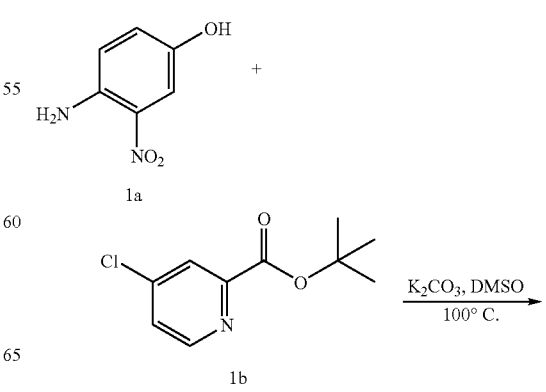

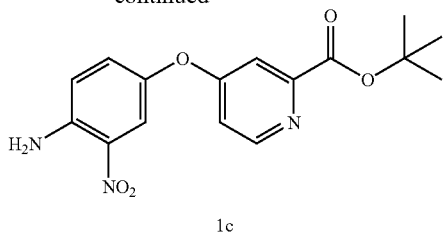

1c

A 500 mL three-neck flask was fitted with a mechanical stirrer and charged with K$_2$CO$_3$ (4.15 g, 30 mmol). The vessel was sealed, evacuated, and flame dried. The apparatus was allowed to cool to rt and purged with argon. To the reaction flask was added 4-amino-3-nitrophenol 1a (3.08 g, 20 mmol), tert-butyl 4-chloropyridine-2-carboxylate 1b (5.2 g, 24 mmol) and dry dimethylsulfoxide (DMSO) (30 mL). The resulting mixture was stirred vigorously and heated to 100° C. for ~14 h. The reaction was poured over iced phosphate buffer (pH=7) and the reaction flask was rinsed well with methyl t-butyl ether (MTBE) and water. The combined biphasic mixture was filtered through Celite (>2 cm pad). The layers were partitioned and separated and the aqueous phase was extracted with MTBE (3×100 mL). The combined organic layers were washed with water (5×100 mL), dried (MgSO$_4$), and evaporated. The crude residue was adsorbed onto SiO$_2$, and purified by flash chromatography (4:1, 2:1, 1:1 hexanes/EtOAc) to furnish 4.92 g (14.9 mmol, 74% yield) of 1c as a yellow brown solid. $^1$H NMR (300 MHz, CDCl$_3$) δ 8.58 (d, J=5.8 Hz, 1 H), 7.90 (d, J=2.8 Hz, 1 H), 7.56 (d, J=2.5 Hz, 1 H), 7.17 (dd, J=2.8, 8.8 Hz, 1 H), 6.94 (dd, J=2.8, 5.8, Hz, 1 H), 6.91 (d, J=9.1 Hz, 1 H), 6.15 (br s, 2H), 1.62 (s, 9H); $^{13}$C NMR (75 MHz, CDCl$_3$) δ 165.8, 164.0, 151.8, 151.5, 143.4, 143.2, 131.5, 129.8, 121.0, 118.0, 114.2, 113.1, 83.0, 28.4; mp 163-166° C.

Step 2

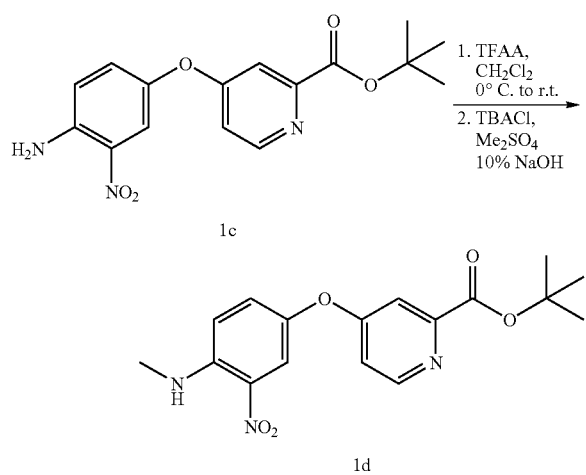

To a solution of 1c (5.62 g, 17 mmol) in CH$_2$Cl$_2$ (85 mL) at 0° C. was added TFAA (2.4 mL, 3.6 g, 17 mmol). The cooling bath was then removed and the reaction maintained at rt for 2 h. The reaction was cooled to 0° C. and TBACl (2.5 g, 8.5 mmol), Me$_2$SO$_4$ (3.2 mL, 4.3 g 34 mmol), and 10% NaOH (34 mL) were added. The resulting mixture was stirred vigorously for 4 h at rt. The reaction was diluted with water and the resulting layers were partitioned and separated. The aqueous phase was extracted with CH$_2$Cl$_2$ (3×100 mL), and the combined organic layers were washed with brine (2×100 mL), dried (MgSO$_4$), and evaporated. The crude residue was adsorbed onto silica gel and purified by flash chromatography (4:1, 2:1, 1:1, 1:2 hexanes/EtOAc) to give 4.5 g (13.0 mmol, 76%) of 1d as a yellow-orange solid. $^1$H NMR (300 MHz, CDCl$_3$) δ 8.54 (d, J=5.5 Hz, 1H), 8.04 (br d, J=4.7 Hz, 1 H), 7.93 (d, J=2.8 Hz, 1 H), 7.53 (d, J=2.5 Hz, 1 H), 7.25 (app dd, J=2.8, 9.1 Hz, 1 H), 6.91 (m, 2 H), 3.04 (d, J=4.9 Hz, 3 H), 1.59 (s, 9 H); $^{13}$C NMR (75 MHz, CDCl$_3$) δ 165.9, 164.1, 151.5, 144.7, 142.1, 130.4, 118.8, 115.5, 114.1, 112.9, 82.9, 30.4, 28.5; mp 187-189° C.

Step 3

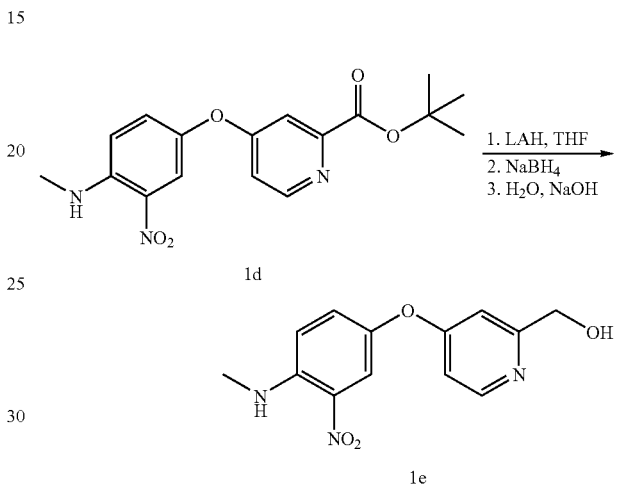

A flame dried 500 mL three necked round bottom flask purged with N$_2$ was charged with LAH (3.0 g, 75 mmol) and dry THF (240 mL). The resulting suspension was cooled to 0° C. and 1d (20.7 g, 60 mmol) was slowly added while keeping the internal reaction temperature under 5° C. The reaction mixture was stirred at 0° C. for 2 h followed by stirring at rt overnight. NaBH$_4$ (2.27 g, 60 mmol) was added and the reaction mixture was stirred for an additional hour at rt. After the reaction was judged complete, the reaction mixture was treated with successive dropwise addition of water (3 mL), 15% NaOH (3 mL), and water (9 mL). The resulting mixture was filtered through Celite, and the remaining solids were washed with EtOAc and MeOH. The combined organic portions were evaporated and the resulting crude residue was adsorbed onto SiO$_2$ and purified by flash chromatography (97:3 CH$_2$Cl$_2$/MeOH) to afford 7.63 g (27.7 mmol, 46%) of a red-orange solid as 1e. $^1$H NMR (300 MHz, CDCl$_3$) δ 8.40 (d, J=5.5 Hz, 1 H), 8.05 (br s, 1H), 7.96 (d, J=2.75 Hz, 1 H), 7.29 (d, J=2.75 Hz, 1 H), 6.92 (d, J=9.35 Hz, 1 H), 6.75 (m, 2 H), 4.68 (s, 2 H), 3.07 (d, J=5.23 Hz, 3 H).

Step 4

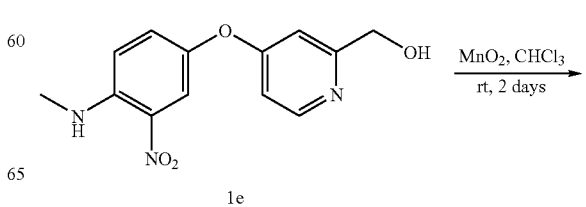

-continued

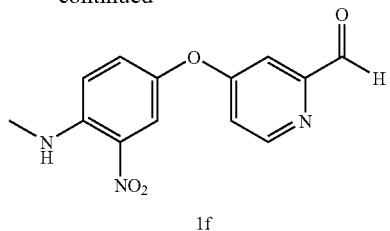

1f

Step 6

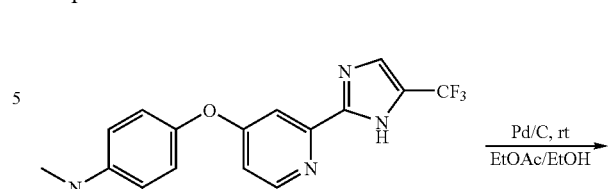

A 100 mL round bottom flask was charged with 1e (1.38 g, 5.0 mmol), MnO$_2$ (6.52 g, 75 mmol) and CHCl$_3$ (20 mL). The resulting suspension stirred at rt for 2 d. The reaction mixture was filtered through Celite, and the remaining solids were washed successively with CHCl$_3$ and EtOH. The combined organic portions were evaporated, absorbed onto silica gel, and purified by flash chromatography (98:2 CH$_2$Cl$_2$/MeOH) to give 790 mg (2.89 mmol, 58%) of an orange solid as 1f. $^1$H NMR (300 MHz, CDCl$_3$) δ 10.01 (s, 1 H), 8.64 (d, J=5.5 Hz, 1 H), 8.09 (br s, 1 H), 7.96 (d, J=2.75 Hz, 1 H), 7.37 (d, J=2.48 Hz, 1 H), 7.29 (d, J=2.75 Hz, 1 H), 7.08 (dd, J=2.47, 5.5 Hz, 1 H), 6.94 (d, J=9.35 Hz, 1 H), 3.08 (d, J=5.23 Hz, 3 H).

Step 5

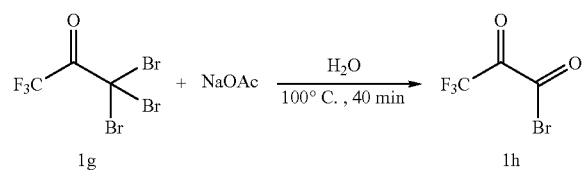

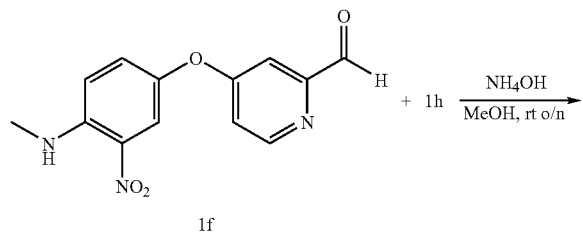

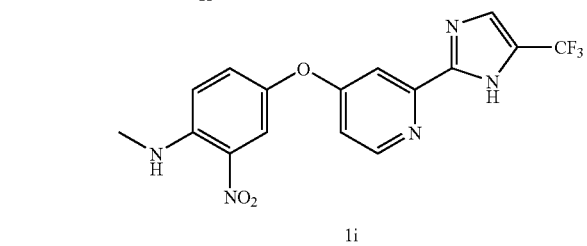

Ketone 1g (Lancaster, 25.75 mL, 136.5 mmol) was added to a solution of sodium acetate (NaOAc) (22.4 g, 273 mmol) in H$_2$O (60 mL) and the resulting solution heated to 100° C. for 10 min. After cooling to rt, the solution of 1h was added to a suspension of 1f (25 g, 91 mmol) in NH$_4$OH (150 mL) and MeOH (450 mL). The resulting mixture was stirred at rt overnight. TLC (95:5 CH$_2$Cl$_2$/MeOH) showed complete consumption of 1f. The crude product was concentrated into an aqueous slurry, and partitioned with saturated Na$_2$CO$_3$ and CH$_2$Cl$_2$. The aqueous phase was extracted three times with CH$_2$Cl$_2$, and the combined organics washed with brine, dried with MgSO$_4$, and concentrated to give 31.6 g of 1i (83 mmol) as an orange solid (91% yield). No further purification was required.

A slurry of 1i (45.76 g, 120 mmol) in MeOH (220 mL) and EtOAc (200 mL) was sparged with N$_2$ for 20 min, and then charged with a suspension of 10% Pd/C (12.77 g, 120 mmol) in MeOH (60 mL). The reaction was purged with H$_2$ and maintained under a H$_2$ atmosphere for 2 days. The reaction was filtered through a pad of Celite and the collected solids were washed successively with MeOH and EtOAc. The combined organic filtrates were evaporated, and the resulting solid was azeotroped with CH$_2$Cl$_2$ and dried overnight, under vacuum, to give 40.17 g (115 mmol) of 1j as a tan powder (96% yield). LCMS m/z 336.1 (MH$^+$), t$_R$=1.81 min.

Step 7

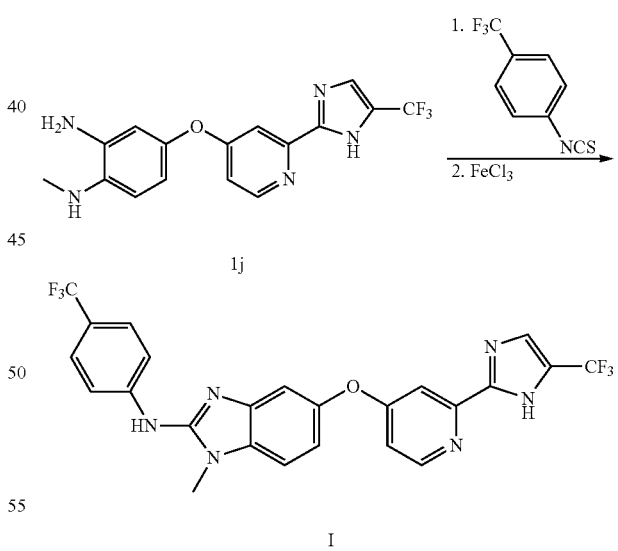

4-(Trifluoromethyl)phenyl isothiocyanate (23.37 g, 115 mmol) was added to a stirring solution of 1j (40.17 g, 115 mmol) in MeOH (460 mL) at rt. The reaction was maintained at rt for 16 h. After the reaction was judged complete, a solution of FeCl$_3$ (20.52 g, 126.5 mmol) in MeOH (50 mL) was added to the reaction and the resulting mixture was stirred at rt overnight. The crude reaction mixture was added to a 3 L separatory funnel containing EtOAc (750 mL) and water (750 mL). The layers were separated, and the aqueous phase was extracted with EtOAc (aqueous phase saved). The organic layers were combined, washed with saturated aqueous $Na_2CO_3$ solution, water, and brine, then dried ($MgSO_4$), and concentrated. The saved aqueous phase was made basic (pH=10) by addition of saturated aqueous $Na_2CO_3$ solution and the resulting slurry was added to a 3 L separatory funnel containing EtOAc (500 mL). The mixture was agitated and the resulting emulsion was filtered through filter paper, and the layers were then separated and the aqueous phase was extracted with EtOAc (2×500 mL). The organic layers were combined, washed with brine, then dried ($MgSO_4$), added to previously extracted material and concentrated. The combined product was triturated with $CH_2Cl_2$ (500 mL), adsorbed onto $SiO_2$ and purified by flash chromatography. A final trituration of material with $CH_2Cl_2$ produced the compound of Formula I as a pure, white solid. LCMS m/z 519.1 ($MH^+$); $^1H$ NMR (300 MHz, $CDCl_3$) δ 8.44 (d, J=5.5 Hz, 1 H), 7.75 (d, J=8.8 Hz, 2H), 7.61 (dd, J=2.2, 8.5 Hz, 1 H), 7.59 (d, J=8.8 Hz, 2 H), 7.56 (d, J=2.5 Hz, 1 H), 7.38 (app d, J=8.5 Hz, 1 H), 7.23 (d, J=1.9 Hz, 1 H), 6.96 (dd, J=2.2, 8.5 Hz, 1 H), 6.93 (dd, J=2.5, 5.5 Hz, 1 H), 3.76 (s, 3 H); LCMS m/z=519.0, $t_R$=2.57 min ($MH^+$); Anal. calc'd for $C_{24}H_{16}F_6N_6O$: C, 55.6; H, 3.11; N, 16.21; Found: C, 55.81; H, 3.43; N, 16.42. mp: 217-220° C. (dec.).

Method B 1,1-Dibromo-3,3,3-trifluoroacetone was added to an aqueous sodium acetate solution. The mixture was heated until it was complete by GC. The reaction mixture, containing was then cooled and added to an ethanol/ethyl acetate solution of 4-(4-methylamino-3-nitrophenol)pyridine-2-carbaldehyde. After the addition was complete, ammonium hydroxide was added and the reaction mixture heated until the reaction was complete by HPLC. The reaction mixture was cooled and the product filtered and washed with water. The yellow solid (3) was then dried under vacuum until a constant weight is obtained.

An aqueous solution of sodium dithionite ($Na_2S_2O_4$) and sodium carbonate ($Na_2CO_3$) was added, portion-wise, to a stirred suspension of 3 in ethanol. After the addition of $Na_2S_2O_4$ and $Na_2CO_3$ was complete, the reaction mixture was stirred until deemed complete by HPLC. Water was then added to the reaction mixture and cooled. The product was filtered and washed with water. The yellow solid (4) was then dried under vacuum until a constant weight was obtained.

4-Trifluoromethylphenyl isothiocyanate (5) was added to a stirred suspension of 4 in acetonitrile. The reaction mixture was stirred until deemed complete by HPLC and then filtered. The filtrate was treated with N,N-diisopropylethylamine and 2-chloro-1,3-dimethylimidazolinium chloride (DMC) until addition of N,N-diisopropylethylamine and DMC was complete. The reaction mixture was heated until deemed complete by HPLC and filtered through a 0.2 μm filter. Water was added to the reaction mixture and then cooled. The title compound was filtered and washed with an acetonitrile/water solution and dried under vacuum until a constant weight was obtained. The product was dissolved in a sufficient amount of refluxing ethanol to achieve a homogeneous solution. The title compound was crystallized out of solution by removal of ethanol by distillation. After distillation of ethanol, the resultant slurry was treated with water and the solution cooled. The solid product was was filtered, washed with ethanol/water and dried under vacuum until constant weight to give the product title compound as an off-white to yellow/brown solid.

Example 18

X-Ray Powder Diffraction Data Collection

The XRPD analyses were performed using a Shimadzu XRD-6000 X-ray powder diffractometer using Cu Kα radiation. The instrument was equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A θ-2θ continuous scan at 3°/min (0.4 sec/0.02° step) from 2.5 to 40° 2θ was used. A silicon standard was analyzed to check the instrument alignment. Data were collected and analyzed using XRD-6000 v. 4.1.

Example 19

Thermal Data Collection

Thermal analyses for differential scanning calorimetry (DSC) (TQ1000, TA Instruments) and thermogravimetric analysis (TGA) (TQ500, TA Instruments) were both conducted at a heating rate of 10° C./min under an inert flow of nitrogen gas at 40 mL/min.

Example 20

Raf/Mek Filtration Assay

Buffers
Assay buffer: 50 mM Tris, pH 7.5, 15 mM $MgCl_2$, 0.1 mM EDTA, 1 mM DTT
Wash buffer: 25 mM Hepes, pH 7.4, 50 mM sodium pyrophosphate, 500 mM NaCl
Stop reagent: 30 mM EDTA
Materials
Raf, active: Upstate Biotech #14-352
Mek, inactive: Upstate Biotech #14-205
$^{33}$P-ATP: NEN Perkin Elmer #NEG 602 h
96 well assay plates: Falcon U-bottom polypropylene plates #35-1190
Filter apparatus: Millipore #MAVM 0960R
96 well filtration plates: Millipore Immobilon 1 #MAIP NOB
Scintillation fluid: Wallac OptiPhase "SuperMix" #1200-439
Assay Conditions
Raf approximately 120 pM
Mek approximately 60 nM
$^{33}$P-ATP 100 nM
Reaction time 45-60 minutes at room temperature
Assay Protocol Raf and Mek are combined at 2× final concentrations in assay buffer (50 mM Tris, pH 7.5, 15 mM $MgCl_2$. 0.1 mM EDTA and 1 mM DTT) and dispensed 15 μL per well in polypropylene assay plates (Falcon U-bottom polypropylene 96 well assay plates #35-1190. Background levels are determined in wells containing Mek and DMSO without Raf.

To the Raf/Mek containing wells are added 3 μL of 10× of a raf kinase inhibitor test compound diluted in 100% DMSO. The raf kinase activity reaction is started by the addition of 12 μL per well of 2.5× $^{33}$P-ATP diluted in assay buffer. After 45-60 minutes, the reactions are stopped with the addition of 70 μL of stop reagent (30 mM EDTA). Filtration plates are pre-wetted for 5 min with 70% ethanol, and then rinsed by filtration with wash buffer. Samples (90 μL) from the reaction wells are then transferred to the filtration plates. The filtration plates are washed 6× with wash buffer using Millipore filtration apparatus.

The plates are dried and 100 μL per well of scintillation fluid (Wallac OptiPhase "SuperMix" #1200-439) is added. The CPM is then determined using a Wallac Microbeta 1450 reader.

Various modifications of the invention, in addition to those described herein, will be apparent to those skilled in the art from the foregoing description. Such modifications are also intended to fall within the scope of the appended claims. Each reference, including all patents, patent applications, and journal literature, cited in the present application is incorporated herein by reference in its entirety.

What is claimed is:

1. A solid form of a hydrate of 1-methyl-5-(2-(5-(trifluoromethyl)-1H-imidazol-2-yl)pyridin-4-yloxy)-N-(4-(trifluoromethyl)phenyl)-1H-benzo[d]imidazol-2-amine having an X-ray powder diffraction pattern comprising characteristic peaks, in terms of 2θ, at about 9.0°, about 17.0°, about 18.4°, and about 25.3°, wherein said pattern comprises no substantial peak at 2θ values below said peak at about 9.0°.

2. The solid form of claim 1 wherein said pattern further comprises no substantial peak at 2θ values from about 14.5° to about 16.0°.

3. The solid form of claim 1 wherein said pattern further comprises at least one characteristic peak, in terms of 2θ, at about 12.1°, about 14.1°, or about 18.7°.

4. The solid form of claim 1 wherein said pattern further comprises at least one characteristic peak, in terms of 2θ, at about 19.5°, about 21.8°, about 21.0°, about 22.7°, about 27.0°, or about 28.0°.

5. The solid form of claim 1 having an X-ray powder diffraction pattern substantially as shown in FIG. 1.

6. The solid form of claim 1 having a DSC thermogram comprising endotherms at about 130 and about 170° C.

7. The solid form of claim 1 having a DSC thermogram substantially as shown in FIG. 17.

8. The solid form of claim 1 which is a monohydrate.

9. A process for preparing the solid form of claim 1 comprising precipitating said solid form from a solution comprising 1-methyl-5-(2-(5-(trifluoromethyl)-1H-imidazol-2-yl)pyridin-4-yloxy) -N-(4-(trifluoromethyl)phenyl)-1H-benzo[d]imidazol-2-amine and a solvent selected from the group consisting of acetonitrile, ethyl acetate, a mixture of acetic acid and water, and a mixture of ethyl acetate and methylene chloride.

* * * * *